US011638613B2

(12) United States Patent
Murphy

(10) Patent No.: US 11,638,613 B2
(45) Date of Patent: May 2, 2023

(54) SYSTEMS AND METHODS FOR AUGMENTED REALITY BASED SURGICAL NAVIGATION

(71) Applicant: Stephen B. Murphy, Winchester, MA (US)

(72) Inventor: Stephen B. Murphy, Winchester, MA (US)

(*) Notice: Subject to any disclaimer, the term of this patent is extended or adjusted under 35 U.S.C. 154(b) by 255 days.

(21) Appl. No.: 16/888,048

(22) Filed: May 29, 2020

(65) Prior Publication Data

US 2020/0375666 A1    Dec. 3, 2020

Related U.S. Application Data

(60) Provisional application No. 62/853,991, filed on May 29, 2019, provisional application No. 62/913,451, (Continued)

(51) Int. Cl.
*A61B 34/20* (2016.01)
*A61B 34/10* (2016.01)
(Continued)

(52) U.S. Cl.
CPC .............. *A61B 34/20* (2016.02); *A61B 34/10* (2016.02); *A61B 90/90* (2016.02); *G02B 27/017* (2013.01);
(Continued)

(58) Field of Classification Search
CPC ......... A61B 34/20; A61B 34/10; A61B 90/90; A61B 1/00193; A61B 2034/102;
(Continued)

(56) References Cited

U.S. PATENT DOCUMENTS 8,267,938 B2   9/2012  Murphy
8,986,309 B1   3/2015  Murphy
(Continued)

FOREIGN PATENT DOCUMENTS

FR       3088005 A1      5/2020
WO   WO-2018/165767 A1   9/2018
(Continued)

OTHER PUBLICATIONS

An, Yong, et al., "A Novel Registration Method for Image-Guided Neurosurgery System Base on Stereo Vision," Bio-Medical Materials and Engineering, IOS Press, vol. 26, Sep. 2015, pp. S967-S973.
(Continued)

*Primary Examiner* — Maurice L. McDowell, Jr.
(74) *Attorney, Agent, or Firm* — Cesari and McKenna, LLP; Michael R. Reinemann

(57) ABSTRACT

The present disclosure involves object recognition as a method of registration, using a stereoscopic camera on Augmented Reality (AR) glasses or an endoscope as the image capture technology. Exemplary objects include surgical tools, anatomical components or features, such as bone or cartilage, etc. By detecting just a portion of the object in the image data of the surgical scene, the present disclosure may register and track a portion of the patient's anatomy, such as the pelvis, the knee, etc. The present disclosure also optionally displays information on the AR glasses themselves, such as the entire pelvis, the femur, the tibia, etc. The present disclosure may include combinations of the foregoing features, and may eliminate the need for electromagnetic, inertial, or infrared stereoscopic tracking as the tracking technology.

19 Claims, 55 Drawing Sheets

Related U.S. Application Data filed on Oct. 10, 2019, provisional application No. 63/000,690, filed on Mar. 27, 2020.

(51) Int. Cl.
| | |
|---|---|
| *A61B 90/90* | (2016.01) |
| *G02B 27/01* | (2006.01) |
| *G06T 19/00* | (2011.01) |
| *A61B 1/00* | (2006.01) |

(52) U.S. Cl.
CPC .......... *G06T 19/003* (2013.01); *G06T 19/006* (2013.01); *A61B 1/00193* (2013.01); *A61B 2034/102* (2016.02); *A61B 2034/105* (2016.02); *A61B 2034/107* (2016.02); *A61B 2034/2051* (2016.02); *A61B 2034/2055* (2016.02); *A61B 2034/2068* (2016.02); *G02B 2027/0174* (2013.01); *G02B 2027/0178* (2013.01); *G06T 2210/41* (2013.01); *G06T 2219/008* (2013.01)

(58) Field of Classification Search
CPC ........ A61B 2034/105; A61B 2034/107; A61B 2034/2051; A61B 2034/2055; A61B 2034/2068; A61B 17/155; A61B 17/1746; A61B 2034/2057; A61B 2034/254; A61B 90/16; A61B 2017/568; A61B 2034/2048; A61B 2034/256; A61B 2090/371; A61B 2090/372; A61B 34/25; A61B 2090/502; A61B 90/36; A61B 90/96; A61B 2017/00203; A61B 2017/00207; A61B 2017/00216; A61B 2017/00221; A61B 2034/108; A61B 2034/2065; A61B 2090/0807; A61B 2090/364; A61B 2090/365; A61B 2090/368; A61B 2090/3937; A61B 2090/3941; A61B 2090/3983; G02B 27/017; G02B 2027/0174; G02B 2027/0178; G02B 23/2484; G02B 2027/0138; G02B 2027/0187; G06T 19/003; G06T 19/006; G06T 2210/41; G06T 2219/008; A61C 1/084; A61M 2205/507

See application file for complete search history.

(56) References Cited

U.S. PATENT DOCUMENTS

| | | | |
|---|---|---|---|
| 10,368,947 | B2 | 8/2019 | Lang |
| 10,405,927 | B1 | 9/2019 | Lang |
| 10,475,244 | B2 | 11/2019 | Cvetko et al. |
| 10,535,151 | B2 | 1/2020 | Bleyer et al. |
| 10,546,423 | B2 | 1/2020 | Jones et al. |
| 10,603,113 | B2 | 3/2020 | Lang |
| 2004/0152970 | A1* | 8/2004 | Hunter .................. A61F 2/4425 600/424 |
| 2009/0306679 | A1 | 12/2009 | Murphy |
| 2011/0069867 | A1* | 3/2011 | Buehner ................ A61B 90/39 382/294 |
| 2013/0310963 | A1* | 11/2013 | Davison ................... A61B 6/14 700/98 |
| 2014/0081659 | A1 | 3/2014 | Nawana et al. |
| 2014/0282008 | A1* | 9/2014 | Verard ................. G03H 1/0005 715/728 |
| 2014/0358151 | A1 | 12/2014 | Murphy et al. |
| 2015/0248793 | A1 | 9/2015 | Abovitz et al. |
| 2015/0250450 | A1* | 9/2015 | Thomas ................. A61B 8/085 600/407 |
| 2016/0143699 | A1 | 5/2016 | Tanji |
| 2016/0191887 | A1 | 6/2016 | Casas |
| 2016/0228193 | A1 | 8/2016 | Moctezuma de la Barrera et al. |
| 2017/0196521 | A1* | 7/2017 | Huang .................. A61C 9/0046 |
| 2018/0168740 | A1 | 6/2018 | Ryan et al. |
| 2018/0185100 | A1 | 7/2018 | Weinstein et al. |
| 2018/0256256 | A1 | 9/2018 | May et al. |
| 2018/0303558 | A1 | 10/2018 | Thomas |
| 2018/0325618 | A1* | 11/2018 | Justin ..................... A61B 34/20 |
| 2019/0005724 | A1 | 1/2019 | Pahud et al. |
| 2019/0025587 | A1 | 1/2019 | Osterhout et al. |
| 2019/0167352 | A1* | 6/2019 | Mahfouz ............... A61F 2/4603 |
| 2019/0170510 | A1 | 6/2019 | Robinson |
| 2019/0285897 | A1 | 9/2019 | Topliss et al. |
| 2020/0097119 | A1 | 3/2020 | Pahud et al. |
| 2020/0110361 | A1 | 4/2020 | Georgiou et al. |
| 2020/0111232 | A1 | 4/2020 | Bleyer et al. |
| 2021/0192759 | A1* | 6/2021 | Lang ..................... A61B 34/25 |

FOREIGN PATENT DOCUMENTS

| | | |
|---|---|---|
| WO | WO-2018/195529 A1 | 10/2018 |
| WO | WO-2018/203304 A1 | 11/2018 |
| WO | WO-2020/099268 A1 | 5/2020 |

OTHER PUBLICATIONS

Bamji, Cyrus S., et al., "5.8 1Mpixel 65nm BSI 320MHz Demodulated TOF Image Sensor with 3.5μm Global Shutter Pixels and Analog Binning," IEEE, IEEE International Solid-state Circuits Conference, ISSCC2018, Session 5, Image Sensors, 5.8, Feb. 12, 2018, pp. 94-96.

Birkfellner, Wolfgang, et al. "Stereoscopic Visualization in the Varioscope AR: A See-Through Head-Mounted Display for Surgical Navigation," Proceedings of SPIE, Medical Imaging 2002: Visualization, Image-Guided Procedures, and Display, San Diego, California, USA, vol. 4681, May 17, 2002, pp. 425-435.

Chen, Long, et al., "Optimization of Virtual and Real Registration Technology Based on Augmented Reality in a Surgical Navigation System," Research, BMC, BioMedical Engineering OnLine, vol. 19, No. 1, Jan. 8, 2020, pp. 1-28.

"Coordinate Systems," Microsoft, Jun. 11, 2019, pp. 1-6.

Frantz, Taylor, et al., "Augmenting Microsoft's HoloLens with Vuforia Tracking for Neuronavigation," Healthcare Technology Letters, vol. 5, Issue. 5, Oct. 4, 2018, pp. 221-225.

Liebmann, Florentin, et al., "Pedicle Screw Navigation using Surface Digitization on the Microsoft HoloLens," original Article, CARS, Springer, International Journal of Computer Assisted Radiology and Surgery, vol. 14, Apr. 15, 2019, pp. 1157-1165.

Linte, Cristian A., et al., "On Mixed Reality Environments for Minimally Invasive Therapy Guidance: Systems Architecture, Success and Challenges in Their Implementation from Laboratory to Clinic," Elsevier Ltd, National Institute of Health, NIH Public Access, Mar. 2013, pp. 83-97.

Liu, He, et al., "Augmented Reality Based Navigation for Computer Assisted Hip Resurfacing: A Proof of Concept Study," Medical Robotics, Biomedical Engineering Society, BMES, Annals of Biomedical Engineering, vol. 46, No. 10, May 23, 2018, pp. 1595-1605.

"Locatable Camera," Locatable camera—Mixed Reality, Microsoft Docs, Microsoft, <https://docs.microsoft.com/en-us/windows/mixed-reality/locatable-camera>, Jun. 12, 2019, pp. 1-6.

Lovo, Eduardo, M.D., et al., "A Novel, Inexpensive Method of Image Coregistration for Applications in Image-Guided Surgery Using Augmented Reality," Methodology Improvements, Neurosurgery, Operative Neurosurgery 2, vol. 60, pp. ONS366-ONS372, Apr. 2007.

Mahvash, Mehran, et al., "A Novel Augmented Reality System of Image Projection for Image-Guided Neurosurgery," Technical Note-Brain Tumors, Springer-Verlag Wien, Acta Neurochir, vol. 155, Mar. 15, 2013, pp. 943-947.

Mirota, Daniel J., et al., "Vision-Based Navigation in Image-Guided Interventions," Annual Reviews, The Annual Review of Biomedical Engineering, vol. 13, May 10, 2011, pp. 297-319.

"Notification of Transmittal of the International Search Report and the Written Opinion of the International Searching Authority, or the

(56) References Cited

OTHER PUBLICATIONS

Declaration," International Filing Date: May 29, 2020, International Application No. PCT/US2020/035204, dated Sep. 14, 2020, pp. 1-18.
"QR Code Tracking," Microsoft, Jun. 11, 2019, pp. 1-7.
Schönberger, Johannes, "HoloLens as a Tool for Computer Vision Research," ECCV 2018, Microsoft, Sep. 2018, pp. 1-31.
"Spatial Anchors," Microsoft, May 16, 2019, pp. 1-3.
"Spatial Mapping," Microsoft, Mar. 26, 2019, pp. 1-9.
Tabrizi Besharati, Leila, et al., Augmented Reality-Guided Neurosurgery: Accuracy and Intraoperative Application of an Image Projection Technique, Clinical Article, AANS, JNS, J Neurosurg, vol. 123, Jul. 2015, pp. 205-211.
Vavra, P., et al., "Recent Development of Augmented Reality in Surgery: A Review," Review Article, Hindawi, Journal of Healthcare Engineering, vol. 2017, Article ID 4574172, Aug. 21, 2017, pp. 1-10.
"Voice Input," Microsoft, Jun. 11, 2019, pp. 1-5.
Abe, Yuichiro, et al., "A Novel 3D Guidance System Using Augmented Reality for Percutaneous Vertebroplasty," American Association of Neurological Surgeons, AANS, Journal of Neurosurgery: Spine, vol. 19, Issue 4, Oct. 2013, pp. 492-501.
Bichlmeier, Christoph, et al., "Contextual Anatomic Mimesis: Hybrid In-Situ Visualization Method for Improving Multi-Sensory Depth Perception in Medical Augmented Reality," IEEE, 2007 6th IEEE and ACM International Symposium on Mixed and Augmented Reality, Nara, Japan, Nov. 13-16, 2007, pp. 1-10.
Chen, Xiaojun, et al., "Development of a Surgical Navigation System Based on Augmented Reality Using an Optical See-Through Head-Mounted Display," Elsevier Inc., Elsevier, ScienceDirect, Journal of Biomedical Informatics, vol. 55, Apr. 13, 2015, pp. 124-131.
Lin, Yen-Kun, et al., "A Novel Denal Implant Guided Surgery Based on Integration of Surgical Template and Augmented Reality," Wiley Periodicals, Inc., Clinical Implant Dentistry and Related Research, Accuracy of a Computer-Guided Surgery System, vol. 17, No. 3, Jul. 24, 2013, pp. 543-553.
Wang, Huixiang, et al., "Precision Insertion of Percutaneous Sacroiliac Screws using a Novel Augmented Reality-Based Navigation System: A Pilot Study," Springer, SICOT aisbl, International Orthopaedics (SICOT), vol. 40, Nov. 16, 2015, pp. 1941-1974.

\* cited by examiner

SYSTEMS AND METHODS FOR AUGMENTED REALITY BASED SURGICAL NAVIGATION

CROSS-REFERENCE TO RELATED APPLICATIONS

The present application claims the benefit of U.S. Provisional Patent Application Ser. No. 62/853,991 filed May 29, 2019, U.S. Provisional Patent Application Ser. No. 62/913,451 filed Oct. 10, 2019, and U.S. Provisional Patent Application Ser. No. 63/000,690 filed Mar. 27, 2020, which applications are hereby incorporated by reference in their entireties.

BACKGROUND

Background Information

Traditional surgical navigation can be broken down into the type of tracking technology used and the type of imaging used, if any. Currently, the most common tracking technologies used for surgical navigation are either infrared stereoscopic optical tracking or inertial tracking. Electromagnetic tracking can be used as well but much less frequently so now. Infrared stereoscopic optical tracking has the limitation that the camera needs its own line of site to the surgical field and it can only track specific objects that have reflective spheres that reflect infrared light or have active light emitting diodes (LEDs) that emit infrared light. Such tracking is incapable of seeing, recognizing, and spatially tracking objects.

With respect to imaging, the basic types of navigation are image-based and image-free. Image-based navigation typically involves using Computed Tomography (CT), Magnetic Resonance (MR) imaging, or 3D Ultrasound and may include the pre-operative or intra-operative development of three-dimensional (3D) models of a patient's anatomy. This computer model of the patient's anatomy is then matched to the actual patient's anatomy through a registration process during surgery after a tracker is affixed to the patient's anatomy. Similarly, navigation analogous to image-based navigation involves substituting 3D models from patient-specific imaging with predictive models of the patient, such as statistical shaped models. For example, a predicted 3D model may be generated for a patient—as opposed to an actual 3D model for the patient—based on 2D X-rays of the patient and information from a large data set of patient statistics and/or statistic shaped models.

For image-free registration, a tracker is similarly affixed to the patient's anatomy but the anatomy is not registered to a 3D model derived from imaging. For example, in the case of image-free navigation for hip arthroplasty, measuring prosthetic acetabular cup orientation and calculating leg length change using image-free navigation techniques involves affixing a tracker to the pelvis. Using one image-free method, the pelvis is then "squared-up", and that position is set to be the starting functional coordinate system for the pelvis. Other instruments are navigated relative to that.

With a second, more typical image-free prosthetic cup and leg length navigation, a skeletal reference frame (tracker) is affixed to the pelvis and a coordinate system such as the Anterior Pelvic (AP) Plane coordinate system is defined relative to the tracker. The AP Plane coordinate system is defined using a digitizer and entering the two superior spine points and the pubic symphysis to instruct the system as to where the tracker is located in space relative to the digitized coordinate system.

For image-based registration, after a pelvic tracker is affixed to the pelvis, a digitizer is used to digitize various points on the pelvic bone surface to achieve spatial registration between the computer model of the patient's pelvis and patient's actual pelvis.

Similarly, the HipXpert® tool from Surgical Planning Associates, Inc. of Medford, Mass. can be used as a registration and tracking device, after a pelvic tracker is affixed, by digitizing the three divots on the tool after the tool is predictably docked to the patient's pelvis. The HipXpert tool is described in U.S. Pat. No. 8,267,938 for a Method and Apparatus for Determining Acetabular Component Positioning, which is hereby incorporated by reference in its entirety.

SUMMARY

Briefly, the present disclosure relates to systems and method for utilizing augmented reality (AR) and/or mixed reality devices to perform registration and/or navigation during surgical procedures. In some embodiments, the AR device may include processors, memory, sensors, and one or more projection systems for displaying virtual images to the user of the AR device, among other elements. Exemplary sensors include photo/video cameras, depth cameras, light sensors, and microphones, among others. Exemplary images include holograms, e.g., objects made from light and sound.

As described, a patient-specific surgical plan may be developed in which the locations of surgical tools and/or implants are planned so as to achive one or more goals of the surgery. The planned locations may be determined relative to a coordinate system associated with a portion of the patient's anatomy, such as the patient's pelvis, femur, tibia, heart, lung, etc. The planned locations also may be translated to be relative to the coordinate system associated with a registration and tracking device that may be affixed to the patient or the planned locations may be originally determined relative to the coordinate system associated with the registration and tracking device. The systems and methods may generate virtual images, such as holograms, of the registration and tracking device, as custom configured for the patient, and of the surgical tools and/or implants at the planned locations. Virtual images of the patient's anatomy or portions thereof may also be generated. During surgery, with the patient in the operating room, patient registration is performed. In some embodiments, patient registration is performed using the registration and tracking device device. For example, the hologram of the registration and tracking device may be presented and co-located, e.g., aligned, with the physical registration and tracking device affixed to the patient in the planned manner, for example manually by the surgeon, automatically by the systems and methods, and/or a combination of manual and automatic techniques. In other embodiments, patient registration may be performed based on object recognition by the systems and methods of a portion of the patient's anatomy, such as recognition of the patient's femoral condyles, the tibial plateau or the acetabulum as exposed during surgery, among other anatomical structures. Holograms of the surgical tools and/or implants in the planned locations may then be presented, and the physical surgical tools and/or implants may be manipulated, e.g., by the surgeon, to co-locate with the holograms, thereby achieving the one or more goals of the surgery. In some embodiments, the surgeon may manually manipulate the hologram of the registration and tracking device and/or the physical registration and tracking device or the patient until the two are co-located. In other embodiments, the registration tracking device may include a recognizable image, for example one or more Quick Response (QR) or other codes. The systems and methods may detect that image, e.g., the one or more QR codes, and automatically co-locate and anchor the hologram of the registration and tracking device with the physical registration and tracking device. In some embodiments, the systems and methods may recognize the registration and tracking device as configured for the patient and docked to the patient's anatomy, some portion of the patient's anatomy, such as a bone surface visible through an incision, and/or some combination of QR codes, registration and tracking device, and patient anatomy. The systems and methods may continuously detect the spatial position and orientation of the image, the registration and tracking device, and/or the patient anatomy during surgery in order to keep the hologram co-located with the physical registration and tracking device.

As noted, in some embodiments, the systems and methods may recognize one or more objects during surgery. For example, the system and methods may recognize some portion of the patient's specific bony anatomy for patient registration and/or to anchor or co-locate one or more virtual images, e.g., holograms. In some embodiments, registration of the patient may be transferred from the registration and tracking device to another device, e.g., a tracking or anchoring device, allowing removal of the registration and tracking device. As noted, the registration and tracking device may be docked to the patient's anatomy. The tracking or anchoring device may be an implant following implantation, such as a prosthetic cup component implanted in the patient's acetabulum.

Shape data for one or more objects, such of which may be patient-specific objects may be generated pre-operatively. Exemplary objects include anatomical structures, such as the patient's pelvis, acetabulum, femur, tibia, etc., and surgical tools or devices some of which may be customized for the patient, such as tools or devices adjusted based on the patient's anatomy and templates fabricated to interfit with the patient's anatomy. The shape data may be in the form of one or more two-dimensional (2D), three-dimensional (3D), or 2D-3D models of the patient-specific object. In some embodiments, the models may be surface models while in other embodiments the models may be solid models. One or more coordinate systems may be defined pre-operatively, for example during a planning phase, based on the patient-specific object. Exemplary coordinate systems include a pelvic coordinate system, a femoral coordinate system, and/or a tibial coordinate system. The coordinate systems may be defined automatically, e.g., by a planning tool, manually by a planning surgeon or surgeon's trained associate, or through a combination of automated and manual steps. In addition, the location of one or more prosthetic components, such as a cup component and/or a femoral stem component, may be planned relative to the one or more coordinate systems. The term location may refer to six parameters determining the position and orientation of an object in space.

During a planning phase, three-dimensional (3D) models of anatomical structures, such as the pelvis, and devices and tools, such as the HipXpert hip registration and tracking device may be generated and used to plan the surgery for a patient. For example, specific prosthetic components may be selected and their locations within the patient's body determined, e.g., to meet one or more goals of the surgery. 3D models of surgical tools, such as reamers and cup impactors, may be generated and their locations for implanting the selected components at the desired locations planned. The desired locations may be final locations, e.g., of a particular tool, or a sequence of locations, e.g., a tool path, from a starting point of a tool to its final location. At least some of the 3D models may be exported into a form that may be used by the head-mounted AR device to generate respective virtual images. During the surgical procedure, the surgeon may wear the AR device, which may be an AR head-mounted device (HMD). The AR device may be configured to include or have access to a navigation system. The navigation system may cooperate with the AR device to generate one or more virtual images, which may be projected onto one or both of the lenses of the AR device, to assist in the surgical procedure. The one or more virtual images may be in the form of holograms of objects, and the holograms may appear from the surgeon's perspective to be in the surgical scene. A hologram is a 3D image formed of light. In some embodiments, the surgeon may operate user interface controls to manually resize and move the holograms so that they are co-located with corresponding physical objects in the surgical scene. Once co-located by the surgeon, the holograms may be anchored at those locations. The surgeon may then operate one or more physical tools until the physical tools are co-located with holograms of the respective tools. With the physical tools co-located with the holograms of the respective tools, anatomical structures may be prepared to receive the prosthetic components as planned, and the selected components may be implanted at the planned locations.

As noted, in some embodiments, a recognizable image, e.g., a QR code, may be affixed to the registration and tracking device in a predetermined location. The systems and methods may detect and recognize this image, e.g., the QR code. Based on the recognition of the QR code, the systems and methods may co-locate the hologram of the registration and tracking device to the physical registration and tracking device. Holograms of the surgical tools at the planned locations may then be presented. In some embodiments, the systems and methods may omit presenting a hologram of the registration and tracking device and instead, having recognized the QR code on the physical registration and tracking device, merely present the holograms of the surgical tools at the planned locations. In some embodiments, multiple QR codes may be used. For example, different QR codes may be placed on the faces of a cube mounted to the registration and tracking device. Each QR code may expose a spatial coordinate system aligned with the QR code, for example at the top left corner of the finder pattern. The AR device may detect the spatial coordinate system associated with one or more of these QR codes. The systems and methods may detect the QR code and/or the spatial coordinate system repeatedly during the surgery, e.g., at some frequency such as five times a second, and thus continuously keep the hologram co-located with the physical registration and tracking device. For example, the AR device may detect the spatial position and orientation of the image, e.g., QR code(s), the registration and tracking device, and/or the patient anatomy at least periodically over some duration of the surgery, such as five times a second or some other frequency, intermittently, continuously, and/or occasionally. The systems and methods may also use an inertial measurement unit (IMU) to keep the hologram co-located with the physical registration and tracking device, for example if line of sight to the registration and tracking device and/or the QR code is lost at any point during the surgery. In some embodiments, the systems or methods may issue one or more alerts and/or warnings if line of sight to the registration and tracking device and/or QR code has been lost for long enough to risk loss of accurate co-location so that re-anchoring is recommended, which may be a predetermined time. For example, presentation of the hologram of the registration and tracking device or any other objects or tools may be stopped or suspended until re-anchoring is performed.

At least a portion of the registration and tracking device including the one or more QR codes may be disposed outside of the patient's body. As a result, the registration and tracking device including the one or more QR codes may be readily detected by the AR device. Nonetheless, virtual images, e.g., holograms, anchored based on the detection of the registration and tracking device may be presented to appear as though they extend into or are entirely disposed inside the patient's body.

In some embodiments, data from the surgical scene as captured by one or more sensors of the AR device may be processed by the navigation system that utilizes the pre-operatively obtained and/or determined shape data for an object, such as a patient-specific object, to detect the object in the surgical scene. This may be referred to as an object recognition mode in which the systems and methods create shape data for an object, such as a patient-specific object, preoperatively and then use object recognition techniques to anchor a virtual image to the real object. It should be understood that only a portion of the actual object may be observable in the data captured by the AR device. Nonetheless, the navigation system may detect the object and determine its location. The navigation system may next register the object, e.g., relative to the one or more pre-operatively determined coordinate systems based on the detection of the object and its determined location. In addition to registering to a coordinate system, the system, once recognizing and co-locating an object, may display a virtual image of any other object or tool onto the surgical scene in the planned location relative to the recognized object. The navigation system may also track the object during the surgical procedure. In some embodiments, registration and tracking of the object may be transferred to a second object, such as a tracker placed on the patient.

The navigation system may generate one or more virtual images, e.g., holograms, which may be projected onto the lenses of the AR device, to assist in the surgical procedure. For example, while only a small portion of the patient's pelvis or knee may be visible through the incision, a hologram of the entire pelvis may be rendered by the AR device and the hologram may be co-located with the patient's physical pelvis. In other embodiments, holograms of the entire femur and/or tibia may be rendered and co-located with the patient's femur or tibia, as examples. Additionally or alternatively, holograms of the one or more coordinate systems and/or guides for implanting one or more prosthetic components at the planned locations may be rendered by the AR device and appear as though they are in the surgical field in order to assist the surgeon in placing the prosthetic components. In some embodiments, the locations of the prosthetic components may be changed during the surgical procedure, and the guides presented to the surgeon by the AR device may be updated to conform to these changes. This may be referred to as a live holography mode in which the systems and methods incrementally or continuously in real time update the holograms to reflect the work performed by the surgical tools, whether directed by the surgeon or by a robot.

The following outline presents one or more embodiments of the present disclosure. It should be understood that different combinations of these features may be implemented in different embodiments of the present disclosure.

1. Image or object recognition for registration and tracking of a registration and tracking device, such as the HipXpert tool, on a patient specific basis. This also registers the pelvis. Image or object recognition may include at least periodically detecting and/or recognizing an image or object over some duration of time during the surgical procedure, such as intermittently, continuously, and/or occasionally over the duration of time.
    1a. augmented reality display of a virtual pelvis superimposed on the patient's pelvis from the surgeon's real-time perspective.
    1b. transferring the pelvic registration to another recognizable tracking object so that the registration and tracking tool, e.g., the HipXpert tool, can be removed from the surgical field.
2. Automated registration of the pelvis based on a view of the acetabulum.
3. Combined registration using 1 and 2 to improve the accuracy of registration. An error in registration can appear visibly as double vision. Improving the accuracy may reduce or eliminate such double vision.
4. Prepare the acetabulum for total hip arthroplasty (THR), for example by lining up a physical cup impactor with a hologram of the cup impactor, perform periacetabular osteotomy, biopsy a lesion, and/or perform other surgical procedure.
    a. Track one or more tools used during the procedure and update the 3D models and/or holograms of the pelvis, femur, etc. based on what has happened so far in real time.
    b. Compare three structures during surgery: the original anatomical structure, the anatomical structure as modified, and the final goal of how the surgeon wants the anatomical structure to be modified.
5. Automated registration of the femur and tibia for total knee arthroplasty using object recognition by creating a virtual patient-specific object, detecting a portion of the real object within the surgical field, and co-locating and anchoring the virtual and real objects together both mathematically and holographically. Registration can be performed using patient-specific object recognition and either track doing the same continuously, or switching to another tracking object or image and tracking of the femur and tibia for total knee arthroplasty (TKA) or any other femur or tibia intervention that involves the knee, femur, or tibia. If coordinate systems are pre-planned, then the surgeon may look directly at the ends of the patient's bones to automatically register the femur and tibia and start navigating the rest of the surgery right away without taking the time to perform the traditional registration steps historically required for surgical navigation. For example, the systems and methods may determine and present to the surgeon where the center of the hip is, where the ankle is, and the coordinate systems of both bones instantly so that he or she may measure motion, ligament balance, bone resection details, etc. The surgeon may also navigate all subsequent tools and show progress of the procedure. The present disclosure may display augmented reality virtual images projected onto the patient from the surgeon's exact perspective using a mixed reality or Augmented Reality (AR) device, such as an AR head mounted device.

6. Embodiments of the present disclosure may transfer registration from tracking the shape of the end of a bone (patient-specific object recognition) to another object, such as a tracker, so that the surgeon can start to modify the bone surfaces without losing tracking ability.

7. Example of endoscopic applications. Using an endoscopic camera that has stereoscopic vision and/or a depth camera, e.g., Time of Flight (ToF) sensors, embodiments of the present disclosure can register an object using an automated object recognition as matched to a 3D model of the same object. Then, if the AR device worn by the surgeon or a stereoscopic tracking system separate from the AR device located in the operating room, such as an Infra Red (IR) tracking system, can see a part of the external portion of the endoscope, the relative location of the AR device to the endoscope's point of view would allow the present disclosure to project virtual 3D objects onto the actual objects from the surgeon's exact point of view. For example, this may be:

a. An endoscopic camera identifies the 3D location of a human body part using stereoscopy and or a combination of sensors to achieve automated 3D (object recognition) surface registration.

b. Then, the back end of the endoscopic camera which exits the person's body can be registered and tracked by the present disclosure including the AR device and/or the IR tracking system, among others.

c. The AR device may then present virtual images, e.g., holograms, of anatomical structures or objects. This allows the surgeon to "see" through the body and "see" the structures or objects virtually through the skin or any other opaque object in between the surgeon and the object. Optimal locations of ligament placement may be calculated and presented, e.g., by the AR device, as can optimal tunnel locations for accessing the calculated ligament placement locations.

In some embodiments, the present disclosure relates to computer-based systems and methods for creating a preoperative plan of a surgical procedure and creating one or more holograms that can be presented, for example during the surgical procedure. The systems and methods include one or more of a surgical planning system, an Augmented Reality Head-Mounted Display (AR-HMD) configured as a surgical guidance system, and one or more registration and tracking devices. The surgical planning system may be utilized to develop a patient-specific surgical plan in which the locations of one or more surgical tools, implants, cutting planes, drilling axes, etc. may be determined preoperatively so as to achieve one or more goals of the surgical procedure. Additionally or alternatively, the surgical plan may further include planned modifications to an anatomical structure, e.g., reshaping a bone surface. The surgical planning system may generate one or more computer-generated models of a portion of a patient's anatomy, such as surface models, based on shape data for the patient from an imaging study. The surgical planning system may establish one or more coordinate systems. The locations of the surgical tools, implants, cutting planes and/or drilling axes and the modifications to the anatomical structures may be planned relative to the one or more coordinate systems. In some embodiments, a location of the registration and tracking device(s) may also be determined relative to the portion of the patient's anatomy and to the one or more coordinate systems. In some embodiments, the locations of the surgical tools, implants, cutting planes and/or drilling axes and the modifications to the anatomical structures may be translated to a coordinate system for the registration and tracking device(s). The planning system may generate images of various combinations of one or more of the patient's anatomy, the registration and tracking device(s), the surgical tools, the implants, the cutting planes and/or the drilling axes at the planned locations, and the anatomical structures as modified. The planning system may convert the images into a format for presentation as holograms by the AR-HMD.

The AR-HMD may utilize image and/or object recognition to recognize the registration and tracking device(s), an image associated with the registration and tracking device(s), and/or a portion of the patient's anatomy to register the patient to the preoperatively generated holograms. For example, with the patient on an operating table in the operating room, the registration and tracking device(s) may be docked to the patient in the planned location (or affixed in a random location). The AR-HMD may detect and track the registration and tracking device(s) during at least a portion of the surgical procedure. The AR-HMD may present the holograms and anchor them to the patient based on the coordinate system for the registration and tracking device(s). The surgeon may utilize the holograms as visual guides during the surgical procedure. For example, the holograms may be called up and presented in a sequence that follows the steps of the surgical procedure. One or more holograms may present a surgical tool in a planned location. The surgeon may manually position the physical surgical tool to be aligned with the surgical tool of the hologram. One or more holograms may present an anatomical structure modified in a planned manner. The surgeon may modify the physical anatomical structure to match the holograms. By using the holograms as guides for operating surgical tools, modifying anatomical structures and/or inserting implants, the surgeon may achieve the one or more goals of the surgical procedure.

In some embodiments, the systems and methods do not perform intraoperative imaging of the patient and do not track surgical tools or implants during the surgical procedure. In other embodiments, the systems and methods may additionally track one or more surgical tools or implants during the surgical procedure.

BRIEF DESCRIPTION OF THE DRAWINGS

The description below refers to the accompanying drawings, of which.

DETAILED DESCRIPTION OF ILLUSTRATIVE EMBODIMENTS

Figure 1:
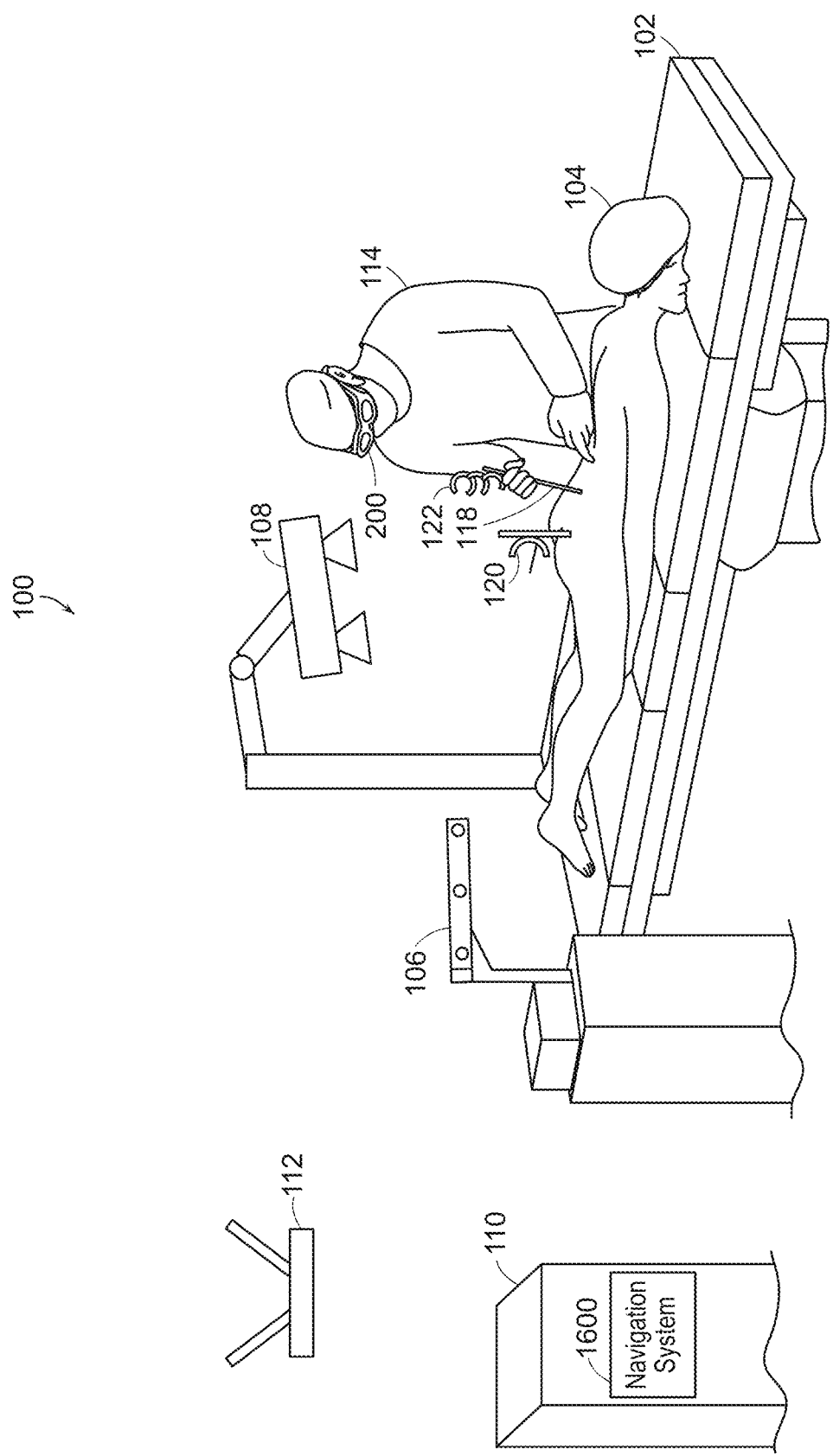
FIG. 1 is a schematic illustration of an operating room in accordance with one or more embodiments.

FIG. 1 is a schematic illustration of an operating room 100 in accordance with one or more embodiments. Disposed in the operating room 100 is an operating table 102 on which a patient 104 is positioned for a surgical procedure. Also disposed in the operating room 100 are a tracking system 106, a data processing device 110, and a network device, such as a wireless router 112. A surgeon 114 may be in the operating room. The surgeon 114 may be wearing an augmented reality (AR) device 200, such as a head mounted device (HMD). Optionally, a three-dimensional (3D) detection system 108 may be disposed in the operating room. Exemplary 3D detection systems include stereoscopic camera systems, Structured Light imaging systems, and Continuous-Wave (CW) Time of Flight (ToF) imaging systems, such as the Azure Kinect Developer Kit (DK) from Microsoft Corp. of Redmond, Wash., which includes an integrated depth camera, color photo/video camera, inertial measurement unit (IMU), and microphone array. The tracking system 106 may implement infrared, inertial, or other tracking techniques. The 3D detection system 108 may capture images or reflections from object in the visible or invisible light range. Images generated by the 3D detection system 108 may be used in embodiments when the AR device 200 includes only a single camera or no cameras. The surgeon 114 may manipulate one or more surgical tools, such as surgical tool 118. In some cases, one or more trackers, such as tracker 120, may be attached to anatomical points of the patient 104. Another tracker 122 may be attached to the surgical tool 118. In some embodiments, the data processing device 110 may host and run some or all of the components of a navigation system 1600. In some embodiments, some or all of the components of the navigation system 1600 may be run by the AR device 200. In some embodiments, other persons in the operating room 100 may be wearing AR devices and holograms presented on the AR device 200 may be presented on these other AR devices. In some embodiments, one or more display devices may be included in the operating room 100. Images captured by the AR device 200 as well as holograms presented by the AR device 200 may be presented on these display devices and watched by others in the operating room 100 and/or by others observing the surgery.

Figure 2:
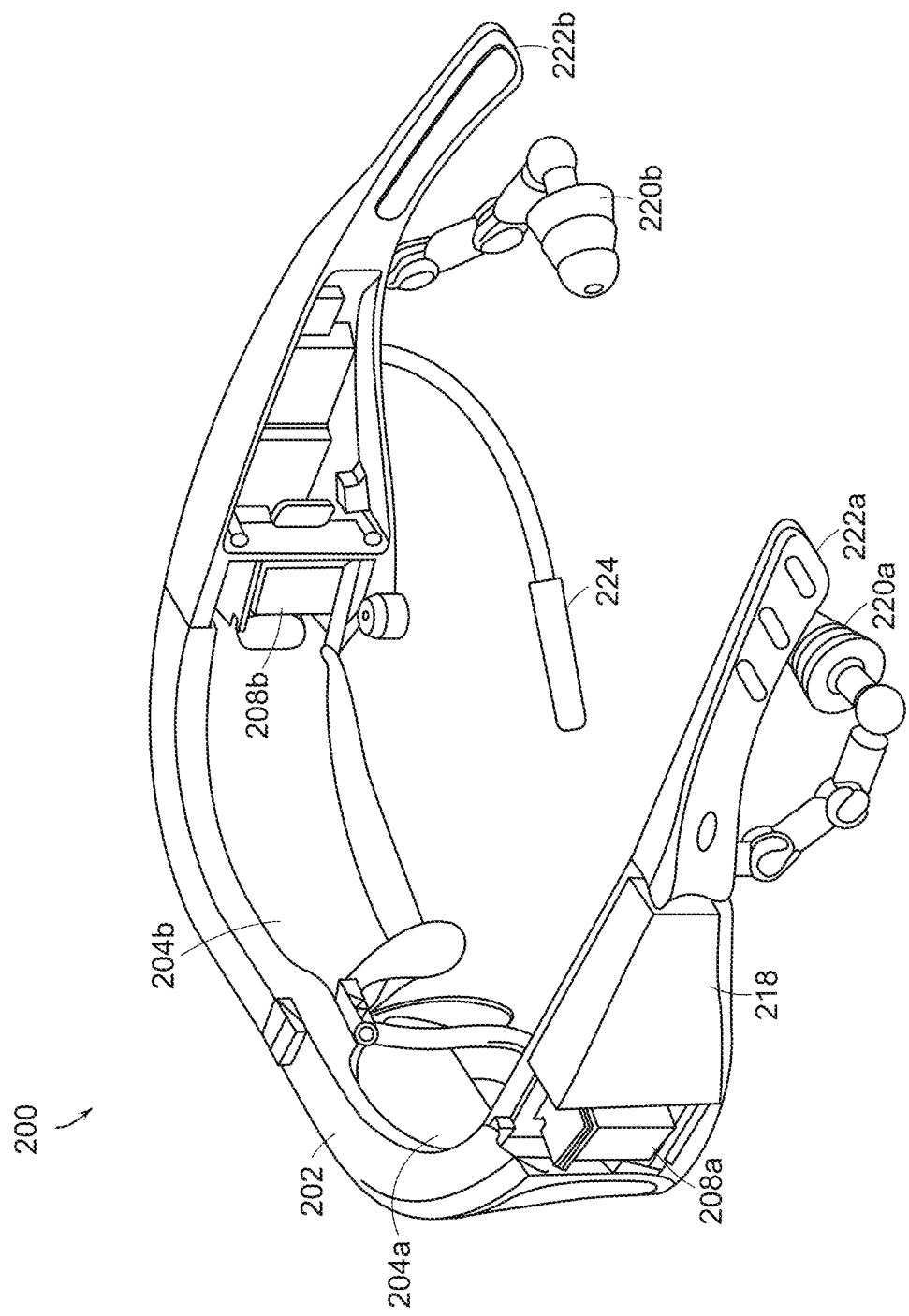
FIG. 2 is a schematic illustration of an Augmented Reality (AR) device in accordance with one or more embodiments.

FIG. 2 is a schematic illustration of an example AR device 200 in accordance with one or more embodiments. The AR device 200 may include projection optics suitable to project a virtual image onto a see-through or translucent lens, enabling the surgeon 114 to view the surrounding environment, such as a surgical field, as well as the displayed virtual image. The AR device 200 may include a frame 202 having two lenses 204a and 204b, two arms 222a and 222b, and projectors 208a and 208b, which may be disposed on the front of the AR device 200 or in the arms 222a and 222b, among other places. The projectors 208a and 208b may project virtual images, e.g., holograms, to the user, for example on the lenses 204a and 204b and/or on the user's eyes. The projectors 208a and 208b may be nanoprojectors, picoprojectors, microprojectors, femtoprojectors, LASER-based projectors, or holographic projectors, among others. As noted, the two lenses 204a and 204b are see-through or translucent, although in other embodiments only one lens, e.g., lens 204a may be translucent while the other lens 204b may be opaque or missing. In some embodiments, the AR device 200 may also include two articulating ear buds 220a and 220b, a radio transceiver 218, and a microphone 224. In some embodiments, the AR device 200 may present one or more sounds associated with holograms and may accept voice commands from the user.

Figure 3:
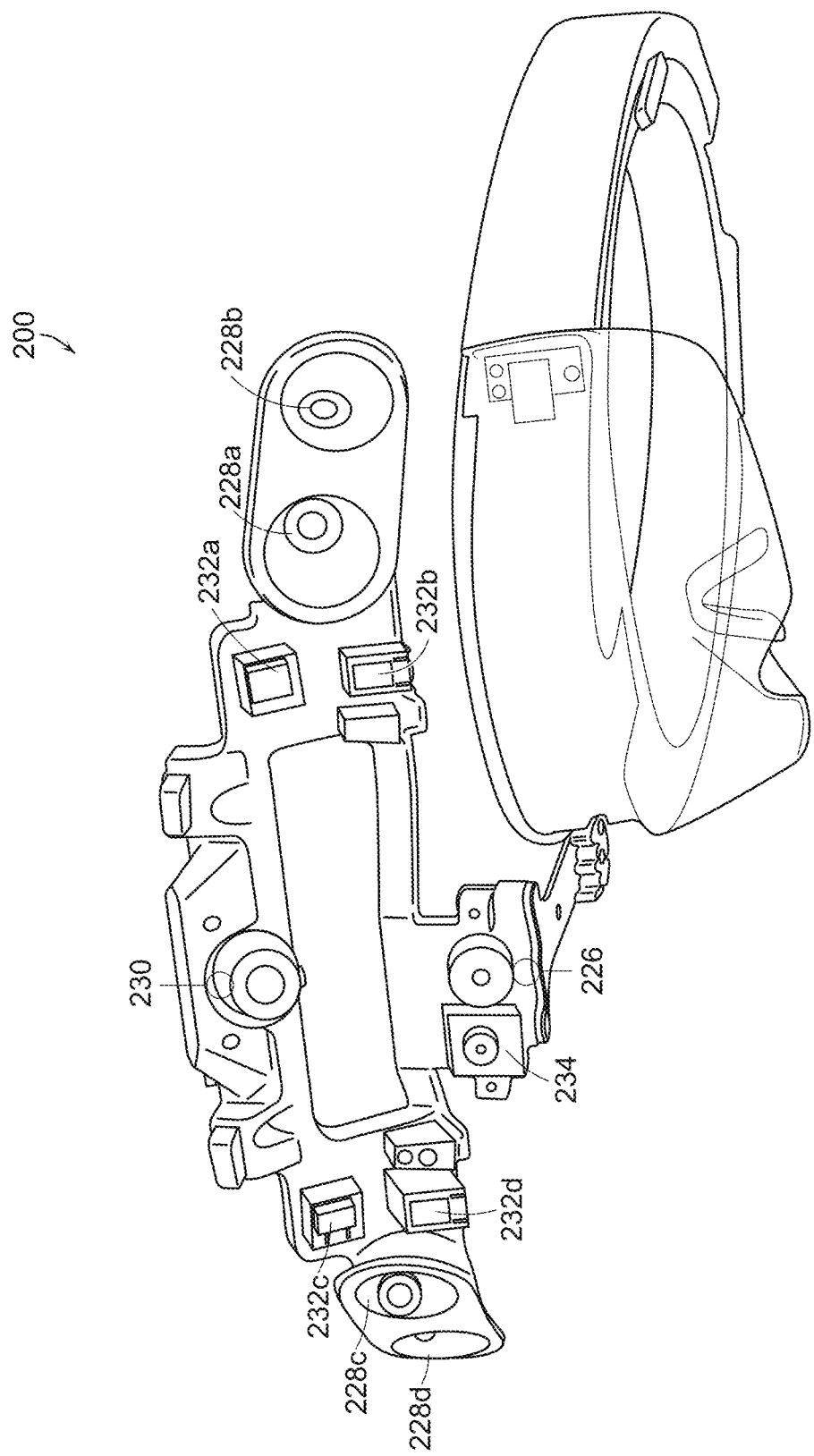
FIG. 3 is a pictorial, perspective, exploded view of an AR device in accordance with one or more embodiments.

FIG. 3 is a pictorial, perspective, exploded view of the AR device 200 in accordance with one or more embodiments. The AR device 200 may further include a plurality of cameras and/or sensors. For example, in some embodiments, the AR device 200 may include a color video camera 226, four gray-scale cameras 228a-d, and one or more depth cameras or sensors, such as a depth camera 230. The AR device 200 also may include one or more infrared (IR) emitters 232a-d that work together with the depth camera 230 as a Continuous-Wave (CW) Time of Flight (ToF) emitter/receiver. The AR device 200 also may include one or more sensors, such as a light sensor 234. It should be understood that the AR device 200 may include other sensors, such as accelerometers, gyroscopes, resistive sensors, current sensors, piezoelectric sensors, voltage sensors, capacitive sensors, global positioning satellite receivers, compasses, altimeters, rangefinders, thermometers, chemical sensors, eye tracking cameras or sensors, and/or moisture sensors. In some embodiments, one or more of the sensors may sense movement of the surgeon 114, such as when and by how much the surgeon 114 moves, tilts and/or swivels his or her head. For example, a set of sensors may be organized as an Inertial Measurement Unit (IMU).

In some embodiments, 3D information of the wearer's environment may be generated from data output by various combinations of the cameras 226, 228a-d, and 230. For example, various combinations of the cameras 226, 228a-d, and 230 may be configured as stereoscopic cameras, a Structured Light emitter/receiver, or the Continuous-Wave (CW) Time of Flight (ToF) emitter/receiver, among others. Various combinations of the cameras 226, 228a-d, and 230 may be referred to as a spatial detection system.

As described, data output by various combinations of the cameras 226, 228a-d, and 230 included on the AR device 200 may be used to perform registration and/or navigation during one or more surgical procedures. In other embodiments, the AR device 200 may include an infrared stereoscopic tracker. In this case, the AR device 200 may be used to perform infrared stereoscopic tracking of one or more trackers, such as the tracker 120 and/or tracker 122, among others. Additionally, an augmented reality viewpoint may be projected onto the AR device 200.

Suitable AR devices include the HoloLens series of mixed reality devices from Microsoft Corp., the Magic Leap One device from Magic Leap, Inc. of Plantation, Fla., and the Blade smart glasses from Vuzix Corp. of West Henrietta, N.Y., among others, and are described in U.S. Patent Publication No. 2019/0025587 for AR Glasses with Event and User Action Control of External Applications to Microsoft Corp. and U.S. Patent Publication No. 2019/0285897 for Display Device to Apple Inc., which are hereby incorporated by reference in their entireties.

Figure 16:
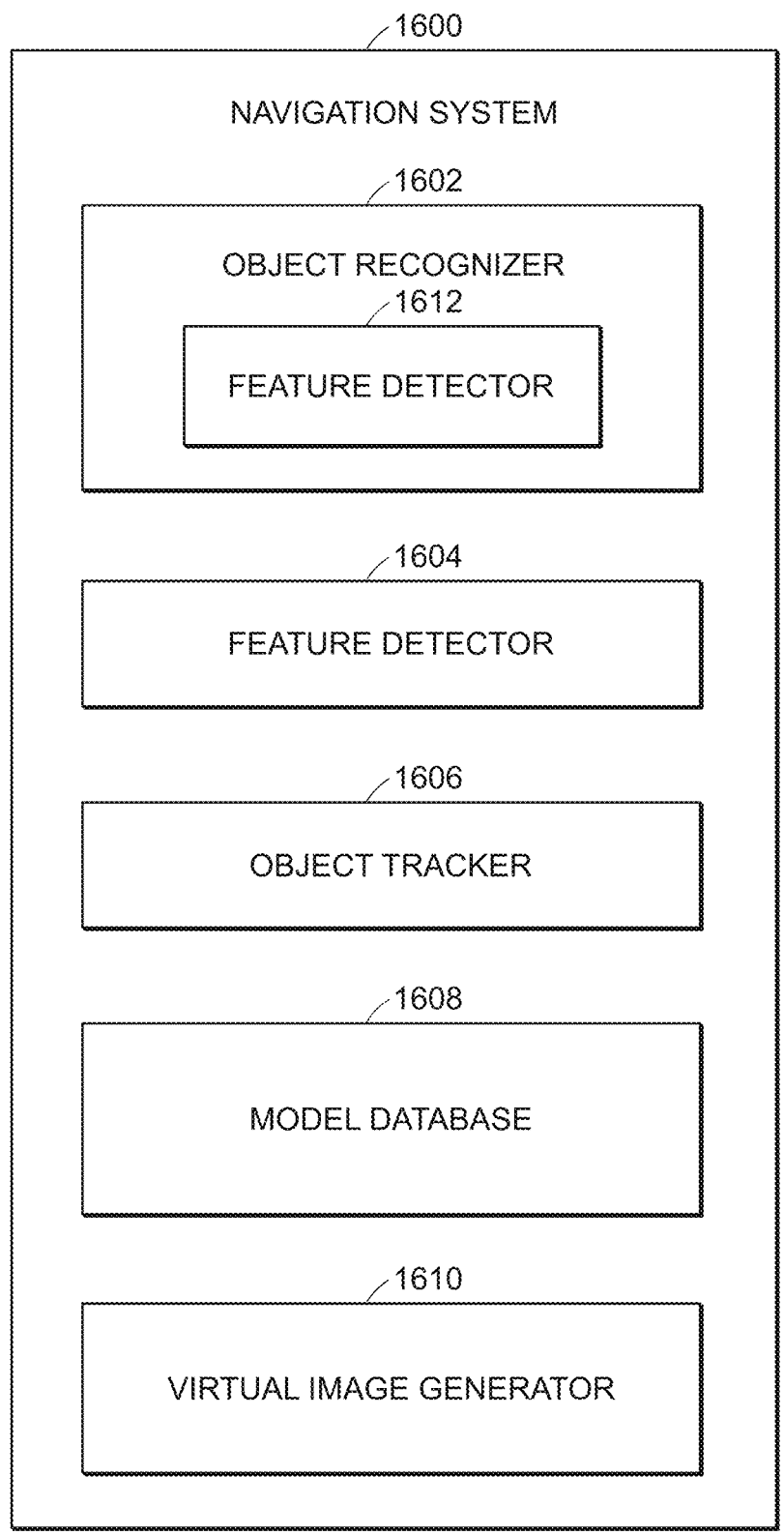
FIG. 16 is a schematic, functional illustration of an example navigation system in accordance with one or more embodiments.

FIG. 16 is a schematic, functional illustration of the navigation system 1600 in accordance with one or more embodiments. The navigation system 1600 may include an object recognizer 1602, an object pose detector 1604, an object tracker 1606, a model database 1608, and a virtual image generator 1610. The object recognizer 1602 may include a feature detector 1612.

It should be understood that the navigation system 1600 is for illustrative purposes only and that the navigation system 1600 may take other forms including additional and/or other components.

One or more of the components of the navigation system 1600 may be implemented using computer vision techniques. Alternatively or additionally, one or more of the components may be implemented using machine learning, such as artificial intelligence (AI), techniques.

In other embodiments, some or all of the components of the navigation system 1600 may be run on the AR device 200, which as noted may include one or more processors and memories. In other embodiments, some or all of the components of the navigation system 1600 may be implemented as a cloud-based service accessible by a client running on the data processing device 110 and/or on the AR device 200. It should be understood that the components of the navigation system 1600 may be implemented in other ways.

Automated Recognition and Registration of Tools and Anatomical Structures: Example: The HipXpert Tool A patient may be diagnosed with a medical condition that requires surgery. In preparation for the surgical procedure, one or more data gathering procedures may be performed. For example, one or more digital images, such as Computed Tomography (CT), Magnetic Resonance Imaging (MRI), conventional radiographs (X-rays), or ultrasonic images, may be taken of the patient. Specifically, images may be taken of that portion of the patient's anatomy on which the surgery is to be performed. It should be understood that any diagnostic test or measurement, particularly one that improves dimensional understanding about the specific portion of the patient's anatomy to be operated upon, may be performed and used for patient-specific planning.

For example, a patient may be diagnosed with hip joint failure, and may require total hip replacement (THR) surgery either on the left hip, the right hip, or both hips. In this case, one or more CT scans of the patient's hip may be taken. The one or more digital images (CT, radiographic, ultrasonic, magnetic, etc.) may be taken on the day of the patient's preoperative visit, at any time prior to surgery, or even during surgery. The one or more digital images may provide three-dimensional information regarding the surface and/or structure of the patient's hip and associated or adjacent structures.

A surgical planner, such as an experienced surgeon or other person, may utilize a 3D modeling tool of a planning tool to create one or more computer-generated, three-dimensional (3D) models of the patient's anatomy, such as the patient's hip, based on the one more digital images taken of the patient, e.g., CT, MR, or other digital images. Additionally or alternatively to generating a model based on CT, MR, or other digital images, a patient-specific model may be created using predictive modeling, e.g., based on patient-specific characteristics. That is, a statistical shaped model or other predictive model may be created on a patient-specific data input, such as a digital x-ray or a combination of minimum datasets.

The surgical planner may utilize the planning tool to create a surgical plan for the surgical procedure that is to be performed on the patient. For example, the surgical planner may create a plan for implanting one or more prosthetic or surgical components, such as an acetabular cup component, into the patient's hip during THR surgery, using one or more surgical tools. The surgical planner may utilize the planning tool to establish one or more coordinate systems, such as the anterior pelvic (AP) plane coordinate system, based on the 3D computer-generated model of the pelvis. Other patient-specific coordinate systems, for example, for use by the one or more surgical tools, may also be established, for example, by selecting three points on the 3D model of the patient's pelvis, such as an ipsilateral hemipelvic plane coordinate system. Further, "functional" coordinate systems may be established based on the position of a body part in a functional position. For example, a functional coordinate system of the pelvis may be established simply by knowing and accepting the position that the patient's pelvis was in while the imaging was acquired.

In some embodiments, the surgical planner may utilize the planning tool to calculate one or more inputs and/or adjustments to be made on the one or more surgical tools, such as the adjustable HipXpert® tool. The inputs and/or adjustments may be based, at least in part, on information, such as spatial information, derived from the 3D model of the pelvis that was created, on some or all of the patient-specific information, and/or on statistical information known to or accessible by the surgical planner. For example, the inputs and/or adjustments may be used to customize the HipXpert tool to fit, e.g., dock, to the patient's pelvis, such that the predicted docking location of the HipXpert tool would be known relative to any other coordinate system of the pelvis, e.g., the AP plane coordinate system. The surgical planner also may choose particular prosthetic hip components, and may plan their location within the 3D model of the pelvis in order to accomplish a particular goal for the surgery, such as optimizing the changes in leg length, offset, and/or AP position. In some cases, optimizing the changes may mean minimizing changes to leg length, offset, and/or AP position. In other cases, it may mean achieving intended changes to leg length, offset, and/or AP position.

The surgical planner may plan the locations of the selected prosthetic components achieve the goals. For example, the location of a selected acetabular cup component within the acetabulum may be determined. The location may include the depth of the cup component in the acetabulum and the planning phase may include determining how the acetabulum should be prepared, e.g., shaped, in order to receive the cup component at the planned location. For example, the plan may specify the depth and/or shape of the cup bed of the acetabulum. The location may include the orientation of an axis, e.g., a central axis, of the cup component relative to the AP plane coordinate system.

A version of the 3D model of the pelvis may be generated with the acetabulum prepared to receive the cup component. For example, a 3D model of the cup bed may be generated. Furthermore, in some embodiments, 3D models of the prosthetic components may be included in and/or available to the planning tool. The surgical planner may place a 3D model of the cup component at the planned location in the 3D model of the pelvis. Similarly, a 3D model of a selected femoral stem may be placed at the planned location in the 3D model of the hip.

In some embodiments, the HipXpert tool may include a guide, such as a rod. The surgical planner may determine one or more adjustments to the HipXpert tool so that, when it is docked to the patient's pelvis, the guide will point in the direction of acetabular cup orientation, as planned.

The surgical plan may thus include instructions for setting up and using one or more surgical tools during the procedure. In other embodiments, the surgical plan may be or may include machine instructions, such as executable code, for operating one or more tools or devices, such as a surgical tool or a machine, to assist during the surgical procedure. In some embodiments, the surgical plan may include machine instructions to be executed by a robotic surgical tool that will perform all or part of the procedure. In addition to controlling a surgical robot, the surgical plan may provide instructions for controlling a free-hand surgical device, such as a rotating tool, to turn on when it is in a location where cutting is to be performed and either turn off or disable cutting, e.g., through deployment of a protective sheath, when it is in a location where cutting should not take place.

Exemplary surgical robots include the surgeon-controlled robotic arms from Mako Surgical Corp. of Fort Lauderdale, Fla. Exemplary free-hand tools include the freehand sculptor from Blue Belt Technologies, Inc. of Pittsburgh, Pa.

Nonetheless, it should also be understood that in some embodiments the surgical plan may be developed and/or revised during the surgical procedure while in other embodiments no explicit surgical plan may be created. For example, with respect to ACL reconstruction of the knee, one or more statistical shaped models may be used as the patient-specific shape data and information may be acquired intraoperatively, such as by landmark digitization and range of motion/kinematic assessment, for developing a surgical plan intraoperatively.

Manual Registration of Holograms: Example: The HipXpert Tool

As described, during a planning stage, an AP Plane coordinate system may be defined for a 3D surface model of a patient's pelvis or portion thereof. In some embodiments, a first 3D surface model may include a portion of one or more of the patient's femurs including the femoral heads in the hip joints. A second 3D surface model may omit the patient's femurs and only include the pelvis or a portion thereof. In some embodiments, a femoral coordinate system and/or a tibial coordinate system may also be defined in addition to the AP Plane coordinate system.

Figure 17:
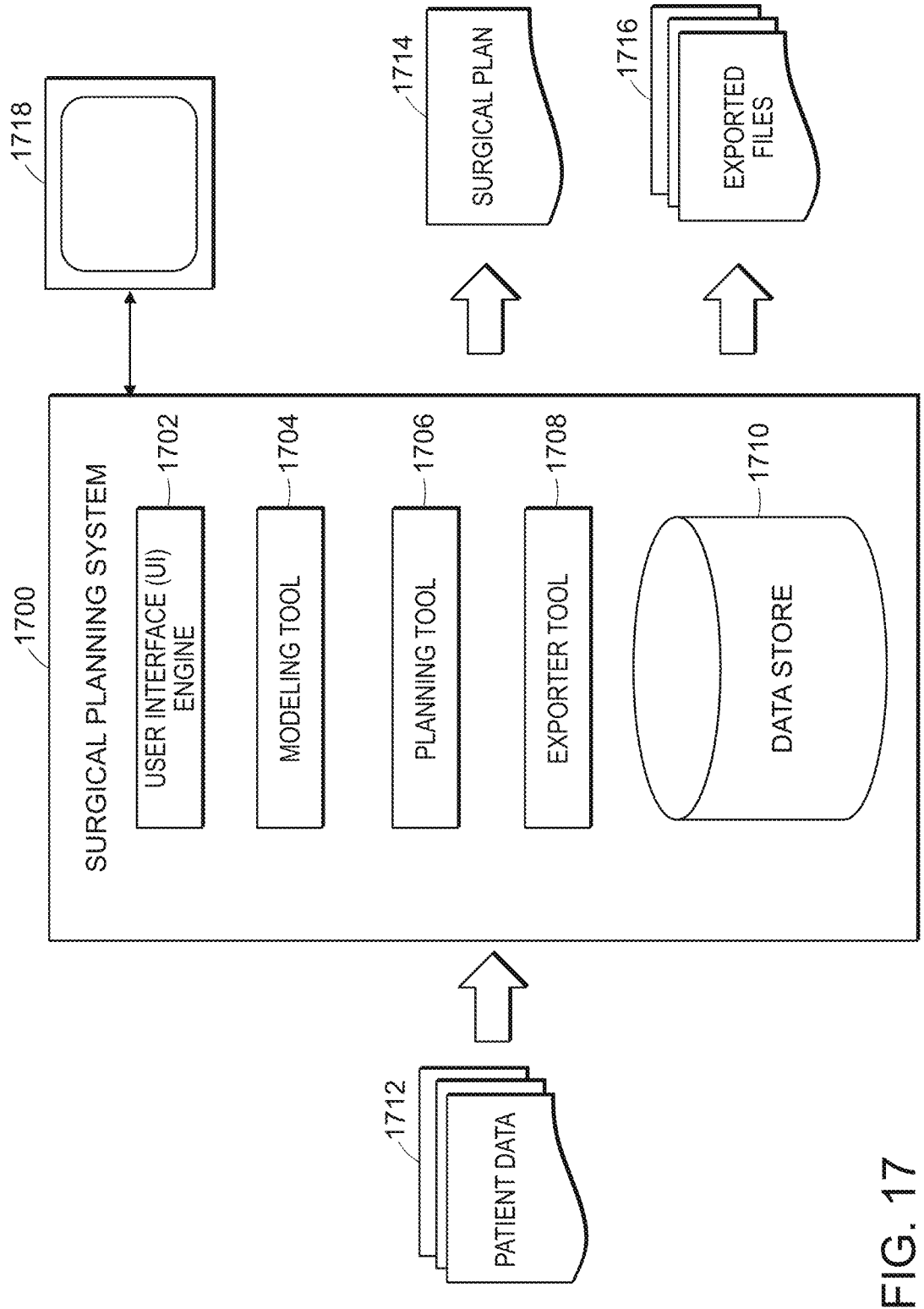
FIG. 17 is a schematic illustration of an example surgical planning system in accordance with one or more embodiments.

FIG. 17 is a schematic illustration of an example surgical planning system 1700 in accordance with one or more embodiments. The surgical planning system 1700 may include a user interface (UI) engine 1702, a modeling tool 1704, a planning tool 1706, an exporter tool 1708, and a data store 1710. The surgical planning system 1700 may receive patient data, as indicated at 1712, which may include volume or shape data in the form of magnetic resonance imaging (MRI) data, computed tomography (CT) data, simultaneous biplanar radiography data, conventional plain radiograph data, ultrasonic data, and/or other data of a patient's hip or other anatomical structure. The surgical planning system 1700 may create one or more electronic surgical plans, such as plan 1714, for the hip surgery, and may export one or more files, e.g., for generating holograms, as indicated at 1716. The surgical planning system 1700 may include or have access to a display 1718.

Suitable tools for generating 2D and/or 3D displays of anatomical structures from volume or shape data include the OsiriX image processing software from Pixmeo SARL of Bernex Switzerland, the TraumaCad pre-operative planning system, the MAKOplasty Total Hip Application pre-operative and intra-operative planning system, and the HipXpert Navigation System Application 1.4.0. Nonetheless, those skilled in the art will understand that other image processing software may be used.

One or more of the patient data 1712, the surgical plan 1714, and the exported files 1716 may be implemented through one or more data structures, such as files, objects, etc., stored in the electronic memory of a data processing device, such as the data store 1710.

As noted, the surgical planner may select one or more prosthetic components to be used in a surgical procedure, such as a prosthetic cup component and/or a femoral stem component, and plan their placement in the patient's body. The plan for the prosthetic cup component may include a planned location, including a depth and an orientation within the acetabulum. The plan may also include the shape of the cup bed to receive the cup component. For the femoral stem component, the plan may define the location of the femoral stem component within the femur and its orientation relative to the femoral coordinate system and/or tibial coordinate system.

In some embodiments, the plan may incorporate 3D models of one or more other tools, such as the HipXpert tool, acetabular reamers and cup impactors, among others.

Figure 18:
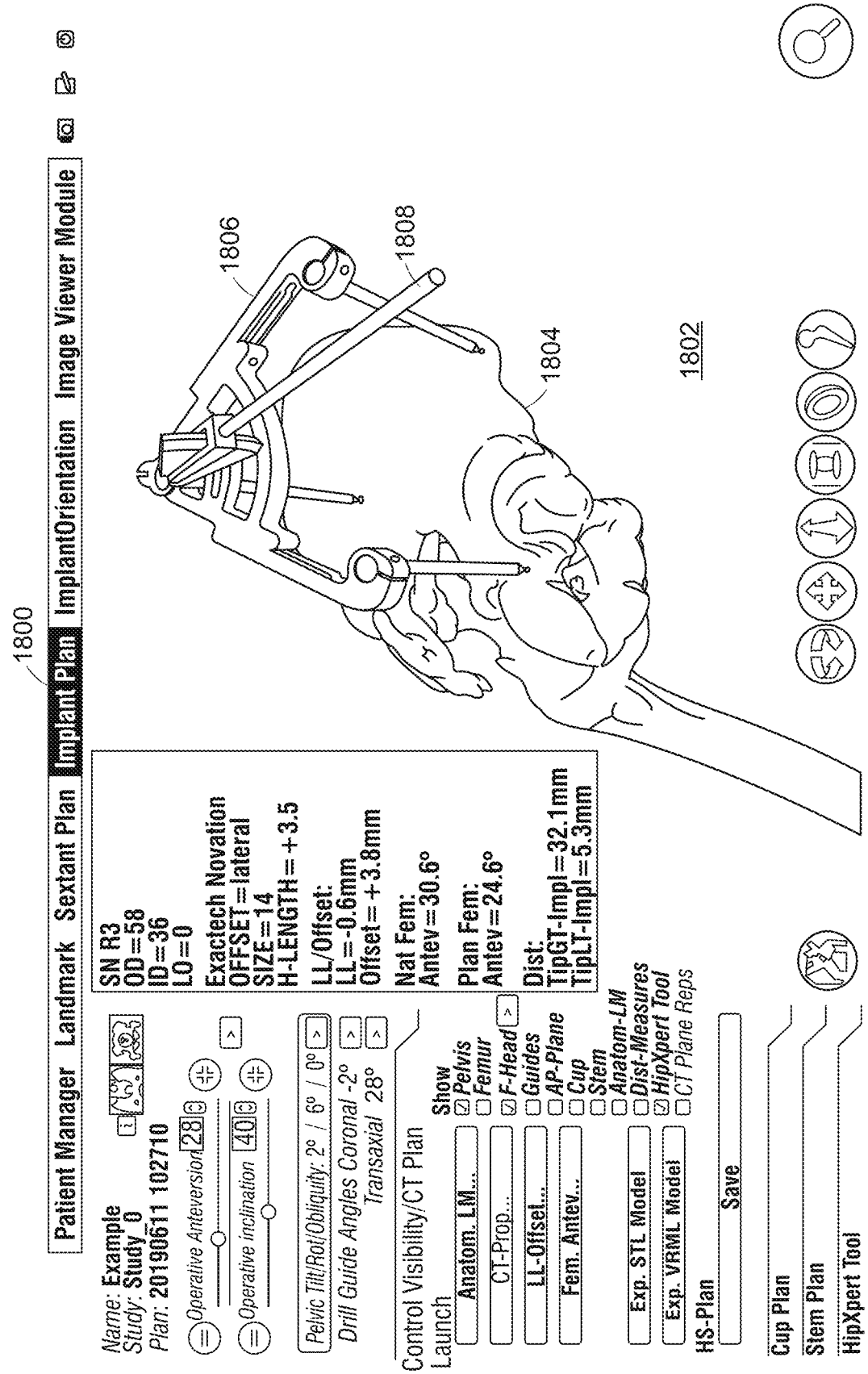
FIG. 18 is an illustration of a planning window in accordance with one or more embodiments.

FIG. 18 is an illustration of a planning window 1800 generated by the surgical planning system 1700 and presented on the display 1718 in accordance with one or more embodiments. The planning window 1800 includes a model pane 1802 presenting a 3D model of the patient's pelvis 1804. Docked to the model of the pelvis 1804 is a 3D model of the HipXpert tool 1806. As noted, the model of the HipXpert tool 1806 may include a guide, such as a rod 1808. If utilized, the planner may determine one or more adjustments to the HipXpert tool so that when it is docked to the patient's pelvis the rod 1808 points in the direction of acetabular cup orientation, as planned.

Figure 30:
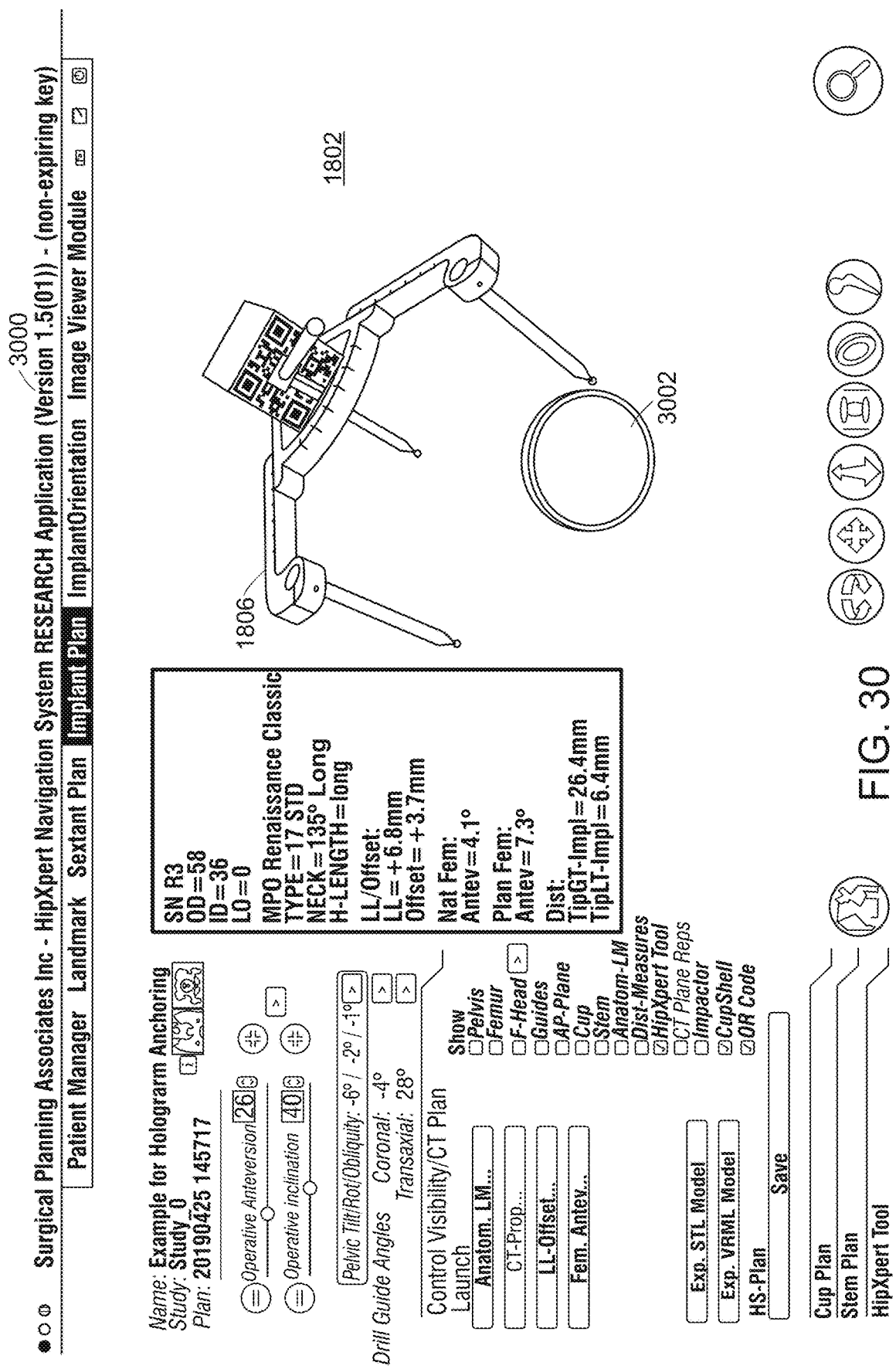
FIG. 30 is an illustration of an example planning window for a portion of a surgical plan in accordance with one or more embodiments.

The surgical planner may plan the position, shape and orientation of the cup bed to receive the prosthetic cup component. FIG. 30 is an illustration of an example planning window 3000 for a portion of a surgical plan in accordance with one or more embodiments. The planning window 3000 also includes the model pane 1802 presenting the 3D model of the HipXpert tool 1806. A 3D model of a cup bed 3002 as planned may also be presented in the model pane 1802. The 3D model of the patient's pelvis appearing in other planning windows may be omitted in the planning window 3000 for the cup bed 3002. The surgical planner may plan the position, shape and orientation of the cup bed 3002 to achieve the goals of the surgery. The cup bed refers to the ideal surgically created bone surface to receive the prosthetic cup component in the planned location.

In some embodiments, the surgical planner may determine the location of the acetabular reamer at the 3D model of the pelvis, e.g., relative to the AP Plane coordinate system, to prepare the cup bed as planned. For example, the acetabular reamer may have a handle defining a longitudinal axis. The surgical planner may position a 3D model of the acetabular reamer so that the cutting basket of the reamer is positioned in the acetabulum to prepare the cup bed as planned in position and orientation.

The surgical planner also may determine the location of the cup impactor at the 3D model of the pelvis, e.g., relative to the AP Plane coordinate system, to implant the cup component in the cup bed as planned. For example, the cup impactor may have a handle defining a longitudinal axis. The surgical planner may position a 3D model of the cup impactor so that the longitudinal axis defined by the handle positions the cup component at the end of the cup impactor in the cup bed as planned.

Figure 19:
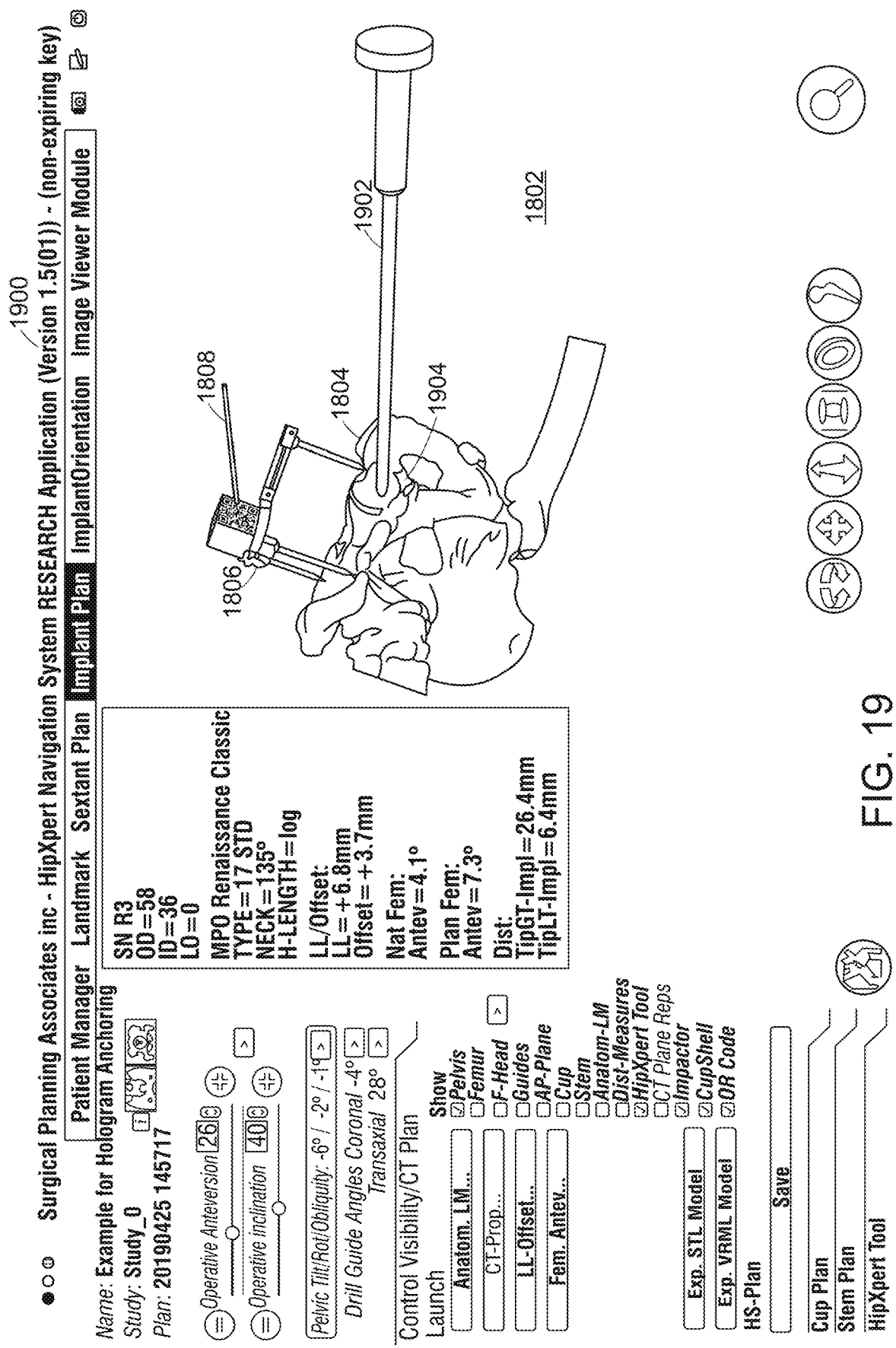
FIG. 19 is an illustration of a planning window in accordance with one or more embodiments

FIG. 19 is an illustration of an example planning window 1900 generated by the surgical planning system 1700 for a portion of a surgical plan and presented on the display 1718 in accordance with one or more embodiments. The planning window 1900 also includes the model pane 1802 presenting the 3D model of the patient's pelvis 1804 and the 3D model of the HipXpert tool 1806. A 3D model of a cup impactor

1902 and a 3D model of a prosthetic cup component 1904 may also be presented in the model pane 1802. The surgical planner may position the model of the cup component 1904 seated in the cup bed at the planned location and orientation. In addition, the surgical planner may position the model of the cup impactor 1902 at the location for implanting the cup component 1904 at the planned position and orientation.

Figure 23:
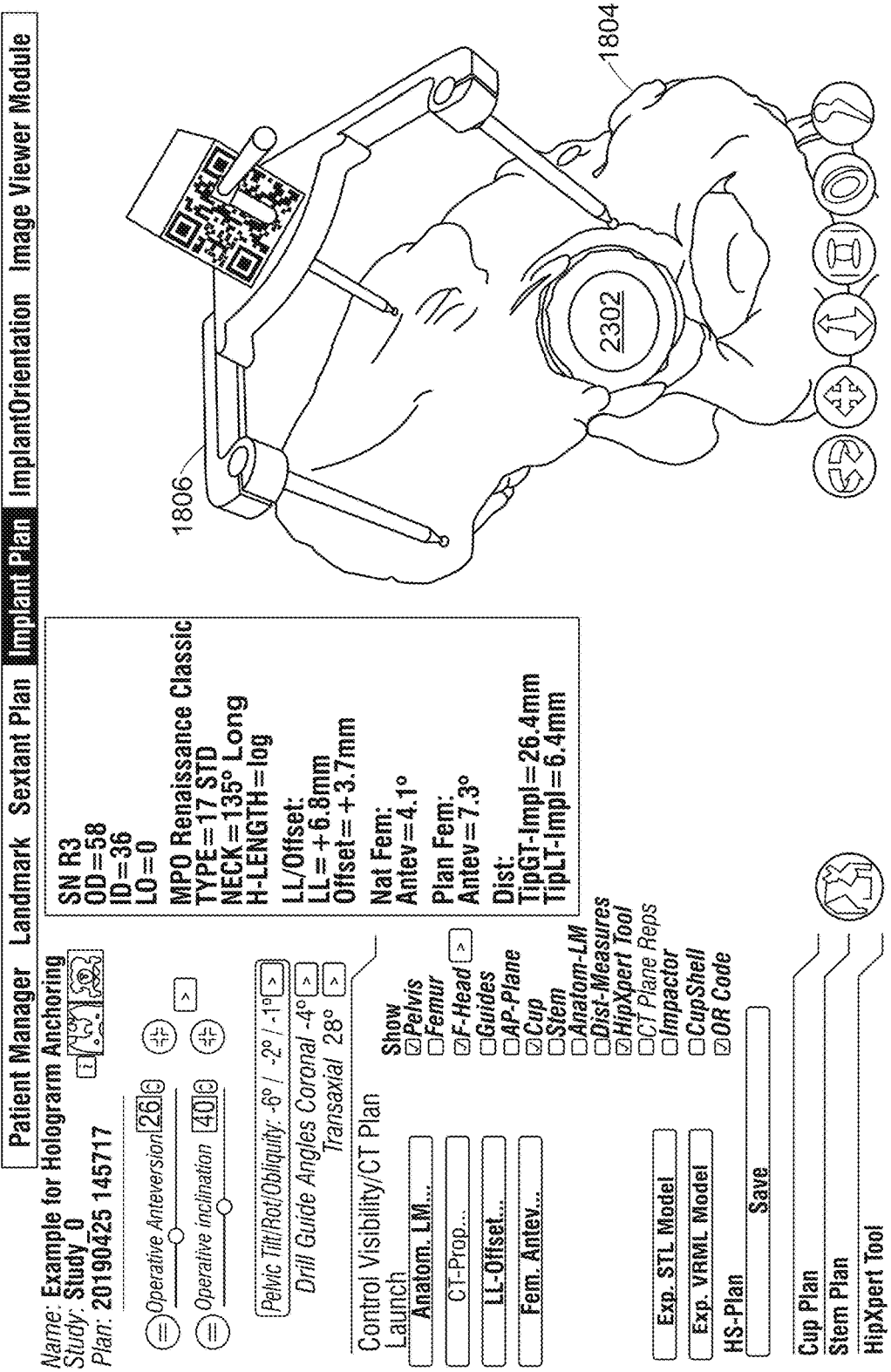
FIG. 23 is an illustration of a planning window in accordance with one or more embodiments.

FIG. 23 is an illustration of an example planning window 2300 for a portion of a surgical plan generated by the planning system 1700 in accordance with one or more embodiments. The planning window 2300 includes the 3D model of the patient's pelvis 1804 and the 3D model of the HipXpert tool 1806. The planning window 2300 further includes a 3D model of a cup component and liner 2302 as implanted in the acetabulum at a desired location, for example relative to the AP Plane coordinate system.

In some embodiments, the plan may also include one or more tracking devices attached to the patient's pelvis whose location is defined relative to the AP Plane coordinate system or another coordinate system. The one or more tracking devices may include a weathervane type device that may be planned to point in the orientation defined for the central axis of the prosthetic cup component.

In some embodiments, the plan may include files of 3D models of one or more of:

the patient's pelvis (or portion thereof);

the patient's femur(s) (both alone and as part of the pelvis);

the HipXpert tool as customized for the patient (both alone and as positioned on the patient's pelvis);

a reamer tool positioned at the planned depth of the acetabulum and in the planned orientation for the cup component relative to the AP Plane coordinate system (or a sequence of reamer tools with different size cup reamers leading to a final one);

a hemispherical surface representing the exact position of the ideally prepared bone surface for receipt of the acetabular component;

a cup impactor tool at the planned position and orientation relative to the AP Plane coordinate system for the cup component;

the selected prosthetic cup component at the planned orientation and depth in the acetabulum relative to the AP Plane coordinate system;

the selected prosthetic cup component and liner at the planned orientation and depth in the acetabulum relative to the AP Plane coordinate system;

the prosthetic stem at the planned orientation and depth relative to the femoral coordinate system, and/or the tibial coordinate system; and/or the one or more tracking devices, e.g., weathervane.

It should be understood that various combinations of the above-listed 3D models also may be created.

As described, by anchoring the holograms, the systems and methods do not have to track any of the surgical tools, e.g., the systems and methods may be free of tracking surgical tools. Instead, the surgeon can track the instruments using his or her eyes to bring the instruments in line with the corresponding anchored holograms. Nonetheless, in some embodiments, the systems and methods may track one or more of the surgical tools.

The planning tool 1706 may export at least some of these 3D model files into a format compatible with the AR device 200 so that the AR device 200 may project holograms corresponding to the exported 3D model files. For example, one or more of the files representing the 3D objects may be exported and loaded into the memory of the AR device 200. Alternatively, the files representing the 3D objects may be stored at a server and the AR device 200 may be configured as a client capable of accessing those files from the server.

For hip surgery, the following sequence of holograms may be generated:

1. A hologram of the HipXpert tool and the pelvis;
2. A hologram of the HipXpert tool, the pelvis, and the ideal acetabular cup bed;
3. A hologram of the HipXpert tool and the ideal cup bed without showing the pelvis;
4. A hologram of the HipXpert tool, the pelvis, the ideal cup bed or the cup component, and the acetabular cup component impaction handle situated in the ideal orientation for implanting the cup component;
5. A hologram of the HipXpert tool, the pelvis, and the metal acetabular cup component without the bearing insert in which the native pelvis has all osteophytes still in place, and
6. A hologram of the HipXpert tool, the pelvis, the metal acetabular component, and the bearing insert.

Nonetheless, it should be understood that other and/or addition holograms may be generated and included. Exemplary additional holograms include: holograms of the acetabular reamer handle and each sequential reamer basket in the ideal location. When the surgeon places the actual reamer handle with the final reamer basket in exact overlap with the hologram of the same, then the cup preparation bed is in the planned place. Such additional holograms may have some advantages over above-described holograms 2 and 3 since the surgeon may be unable to see where the reamer is in space when preparing the bony cup bed. Using those holograms, the surgeon may have to ream, take the reamer out, and look into the incision to compare the real prepared bony cup bed surface to the hologram. If instead or in addition there is a hologram of the exact reamer handle and basket, the surgeon will be able to tell if the cup bed is correct by looking at overlapping holograms and reality mostly outside of the patient's body. This may be more convenient, among other advantages. Also, during cup impaction, instead of the above-described hologram 4 with an idealized straight cup impactor (for alignment only), there may be a hologram of the same exact planned cup impactor to be used in surgery with the same exact planned cup component also to be used in surgery. Then, when impacting the cup, the surgeon can line up not only the orientation of the cup component to be correct, but can also tell if the cup component is fully seated and if it is in the correct place.

In some embodiments, computer-generated, three-dimensional (3D) models, such as other Computer Aided Design (CAD) models, of one or more surgical tools may be stored in the data store 1710. 3D surface models of the surgical tools may be generated from these models and also stored in the data store 1710. In some embodiments, only the 3D surface models may be included in the data store 1710. In some embodiments, 3D surface models of one, a handful or some other small number of standard surgical tools, such as a standard acetabular reamer with a standard cutting basket and a standard acetabular cup impactor may be included in the data store 1710. Holograms that include a reamer or cup impactor may be based on these surface models of a standard reamer or cup impactor.

However, in other embodiments, 3D surface models for actual reamers and/or cup impactors including entire product families from one or more manufacturers, e.g., Stryker Corp. of Kalamazoo, Mich., Greatbatch, Inc. (now Integer Holdings Corp.) of Plano, Tex., Ortho Solutions UK Ltd. of Essex, UK, Zimmer Biomet Holdings, Inc. of Warsaw, Ind., Depuy Synthes of Raynham, Mass., etc., may be included in the data store 1710. Furthermore, 3D surface models for different sizes of cutting baskets and different sizes of acetabular cups may be included in the data store 1710. During the surgical planning phase, 3D surface models corresponding to the particular reamer and the particular cup impactor that the surgeon will be using in the surgery may be selected from the data store 1710 and used in creating the surgical plan. 3D models for cup impactors and cup components may even include spatial assembly information for how each of the planned cup assembles onto the cup impactor, e.g., due to thread depth and shell thickness). In this way, holograms representing the particular surgical tools that the surgeon is using may be generated and presented. Furthermore, a sequence of holograms of a reamer with different basket sizes may be generated to indicate the bone cutting work performed by each reamer basket size before moving to a next reamer basket size. The sequence of holograms may illustrate being moved deeper into the acetabulum as further cutting is performed. That is, each hologram may indicate the exact amount of cutting to be performed by each reamer basket size. Additionally, a hologram of a cup impactor and cup that corresponds to the physical cup component being implanted may be generated.

Prior to the surgical procedure, the navigation system 1600 or one or more portions thereof may be loaded into the memory of the AR device 200 and/or made accessible to the AR headset 200. For example, the AR device 200 may be configured as a client of the navigation system 1600, which may be loaded on and run at a server, such as a laptop computer, that is in communicating relationship with the AR device 200. In some embodiments, the planning tool 1706 used to plan the surgery may be loaded and run on the AR device 200.

During the procedure, the surgeon may adjust a physical HipXpert tool as provided in the plan to customize the tool to fit to the patient's pelvis. The surgeon may then place the physical HipXpert tool on the patient's pelvis. The patient may be positioned on an operating room table. The surgeon may wear the AR device 200. The surgeon may control the AR device 200 to render a hologram of the HipXpert tool attached to a hologram of the patient's pelvis as planned. The surgeon may operate user interface elements provided by the AR device 200 to resize, move, and/or rotate the hologram of the HipXpert tool/pelvis so that the hologram is co-located with the physical HipXpert tool attached to the patient's pelvis, e.g., aligned together. More specifically, while the pelvis may not be visible to the surgeon because it is below the patient's skin, the HipXpert tool, which is docked to the patient's pelvis, is visible to the surgeon. Accordingly, the surgeon may resize, move, and/or rotate the hologram of the HipXpert tool/pelvis until it is co-located with the physical HipXpert tool docked to the patient's pelvis. The hologram of the patient's pelvis will also be co-located with patient's pelvis even though the patient's pelvis is not visible to the surgeon. Once the hologram of the HipXpert tool/pelvis is co-located with the physical HipXpert tool, the surgeon may peg or anchor the hologram of the HipXpert tool/pelvis at that location within the operating room. For example, the AR device 200 may include an anchoring feature for holograms rendered by the AR device 200. In addition, as described herein, in some embodiments, the navigation system 1600 may automatically co-locate one or more of the holograms with reality, for example using image recognition of an image, such as a QR code, or using object recognition of the HipXpert tool as adjusted specifically for the patient.

Figure 24:
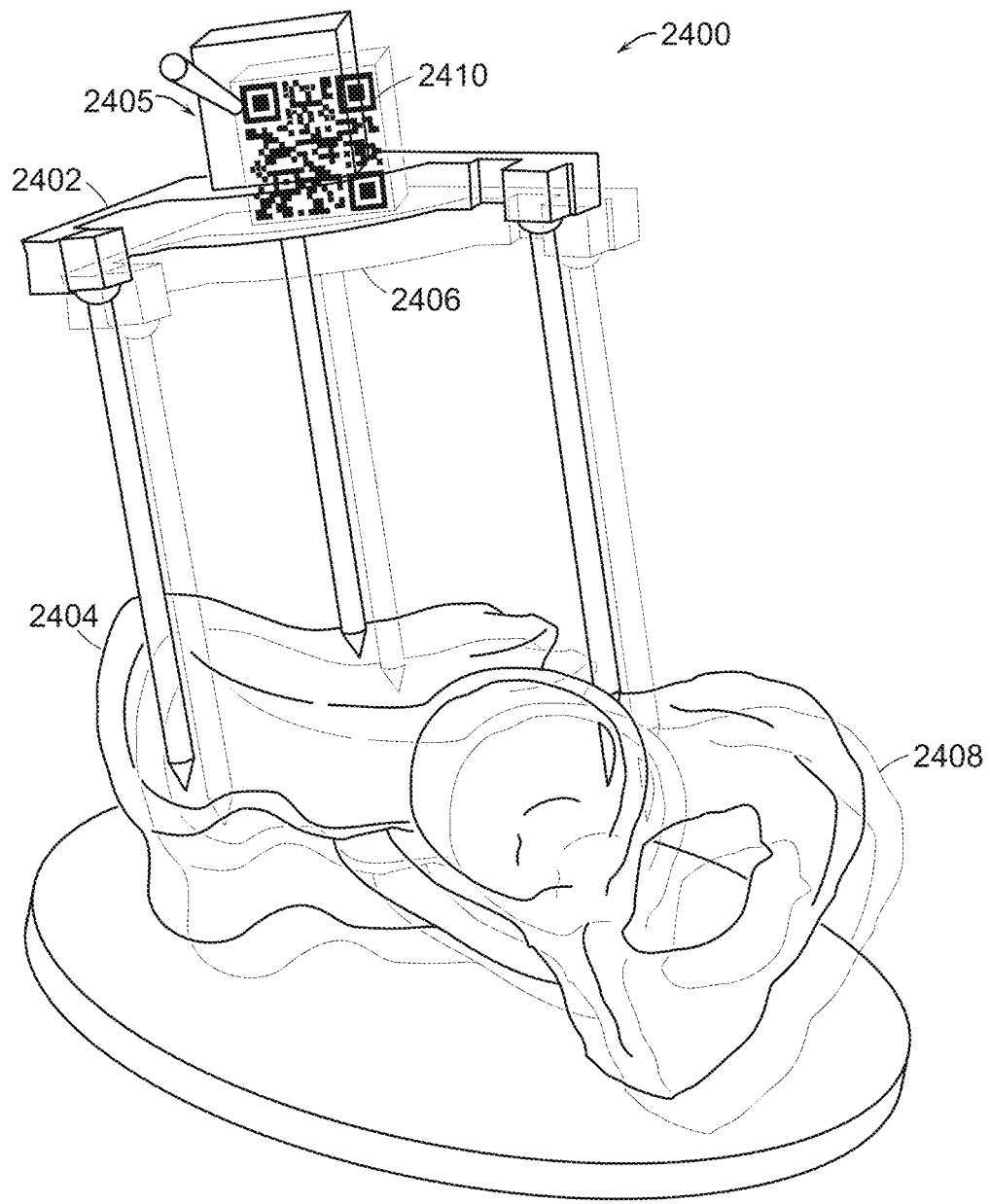
FIG. 24 is a pictorial representation of a hologram colocated with a physical object in accordance with one or more embodiments.

FIG. 24 is a pictorial representation indicated generally at 2400 of a hologram being co-located with a physical object in accordance with one or more embodiments. The representation 2400 includes a physical HipXpert tool 2406 docked to a physical hip model 2408 as planned. The representation 2400 further includes a hologram indicated generally at 2405 that includes a hologram of a HipXpert tool 2402 and a hologram of a hip model 2404 in which the HipXpert tool hologram 2402 is docked to the hologram of the hip model 2404 in the planned manner. The physical HipXpert tool 2406 includes a QR code 2410. The hologram 2405 may be repositioned in space either manually by the wearer of the AR device 200 and/or automatically by the AR device 200 until it is co-located with the physical HipXpert tool 2406. For purposes of explanation, the pictorial representation 2400 shows the physical hip model 2408. However, a patient's hip will not be visible to the surgeon as it is beneath the patient's skin. In some embodiments, the surgeon may manually reposition the hologram 2405 so that the HipXpert tool hologram 2402 is co-located with the physical HipXpert tool 2406, which is visible to the surgeon. While the patient's physical hip is not visible to the surgeon, the hip hologram (illustrated by the hip model hologram 2404) shows the surgeon where the patient's physical hip is. In other embodiments, the object recognizer 1602 may detect the QR code 2410 on the physical HipXpert tool 2406 and automatically co-locate the hologram 2405 to the physical HipXpert tool 2406. Not only may the object recognizer 1602 perform image recognition, such as with a QR code, it may also perform object recognition of the HipXpert tool 2406 itself or the HipXpert tool 2406 plus the actual bony acetabulum.

In some embodiments, the physical HipXpert tool may not include a guide rod. Nonetheless, the surgeon may utilize the guide rod of the hologram of the HipXpert tool to implant the prosthetic cup component in the patient's acetabulum at the planned orientation. That is, the surgeon may use the guide rod of the hologram of the HipXpert tool as a guide for implanting the cup at the planned orientation. Nevertheless, in addition to a hologram of the guide rod (or instead), the AR device 200 may present a hologram of the cup impactor tool, and the surgeon may line up the physical cup impactor tool to this hologram of the cup impactor tool. The surgeon may then manually line up the physical tool with the hologram. As described, in some embodiments, it is not necessary to track the physical tool. Instead, the system may detect one or more of the QR codes of the HipXpert device and anchor the holograms based on the spatial coordinate system exposed by and aligned with the one or more QR codes. The holograms then show the planned locations of the surgical tools, and the surgeon may align the physical tool with the hologram, e.g., the planned location for the tool.

In some embodiments, the surgeon may operate the AR device 200 to render a hologram of the reamer/HipXpert tool/pelvis. The hologram of the reamer may be disposed relative to the hologram of the pelvis such that the hologram of the reamer is at the final position and orientation for preparing the acetabulum to receive the prosthetic cup component relative to the AP Plane coordinate system. The surgeon may operate user interface elements provided by the AR device 200 to resize, move, and/or rotate the hologram of the reamer/HipXpert tool/pelvis so that the hologram is co-located with the physical HipXpert tool attached to the patient's pelvis, e.g., the hologram and the tool are spatially aligned together. The surgeon may operate the AR device 200 to peg or anchor the hologram of the reamer/HipXpert tool/pelvis at that location within the operating room. The surgeon may then operate a physical reamer tool to prepare the acetabulum until the physical reamer is co-located with the hologram of the reamer. For example, the surgeon may position the physical reamer to be co-located with the hologram of the reamer. As noted, the hologram may represent a standard reamer or, in a preferred embodiment, the hologram may represent the particular reamer being used by the surgeon in the surgery, which may make it even easier for the surgeon to line up the physical reamer with the hologram of the reamer. Additionally, a sequence of holograms of reamers, e.g., with different cutting basket sizes, may be presented, and the surgeon may change the physical cutting basket to match the cutting basked included in the hologram. The sequence of holograms also illustrates the depth of cutting to be performed with each cutting basket. When the physical reamer is lined up with the hologram of the reamer, the cutting by the respective cutting basket is complete. The surgeon may change cutting baskets and the next hologram in the sequence may be presented. This process may be repeated until the cup bed is prepared as planned. When the physical reamer (or the physical reamer with the last cutting basket in the case of a sequence of reamers) is co-located with the hologram of the reamer, the cup bed will be prepared for receiving cup component as planned. Suppose for example, the surgical plan call for a 56 mm cup component. The plan may call for a series of reamers, such as a first reamer with a 51 mm basket, a second reamer with a 53 mm basket, a third reamer with a 55 mm basket, and finally a fourth reamer with a 56 mm basket to do a final preparation of the cup bed before putting the cup component in.

The surgeon may operate the AR device 200 to render a hologram of the cup bed/HipXpert tool. The surgeon may operate user interface elements provided by the AR device 200 to resize, move, and/or rotate the hologram of the cup bed/HipXpert tool so that the hologram is co-located with the physical HipXpert tool attached to the patient's pelvis. The surgeon may operate the AR device 200 to peg or anchor the hologram of the cup bed/HipXpert tool at that location within the operation room. The surgeon may look through the incision in the patient and compare the physical acetabulum with the hologram of the cup bed. The surgeon may determine whether the appearance of the physical acetabulum following the reaming matches the hologram of the cup bed. If not, the surgeon may operate the physical reamer to further shape the acetabulum until it matches the hologram of the cup bed.

Figure 25:
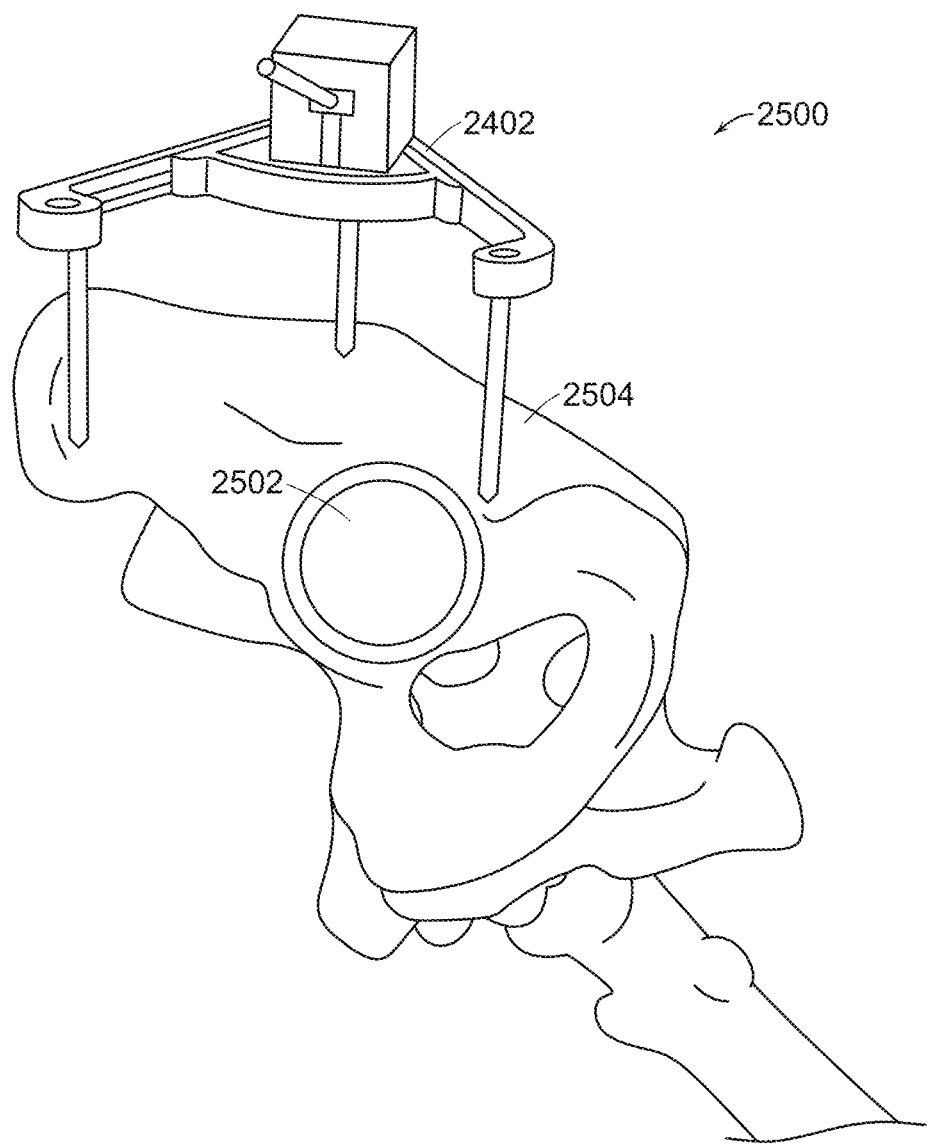
FIG. 25 is a pictorial representation of a hologram in accordance with one or more embodiments.

FIG. 25 is a pictorial representation of a hologram 2500 in accordance with one or more embodiments. The hologram 2500 may include the hologram 2402 of the HipXpert device, a hologram 2504 of the patient's pelvis, and a hologram 2502 of the cup bed as planned. During the surgical procedure, the hologram 2500 may be co-located to the corresponding physical objects either manually and/or automatically, for example by co-locating the hologram 2402 of the HipXpert device with the physical HipXpert device. The surgeon may then examine the physical cup bed as prepared, e.g., through the use of the reamer, and see if the shape of the physical cup bed, e.g., depth and center or orientation, matches the hologram 2502 of the cup bed as planned. If not, the surgeon may continue shaping, e.g., using a reamer, the physical cup bed until it matches the hologram 2502.

Figure 26:
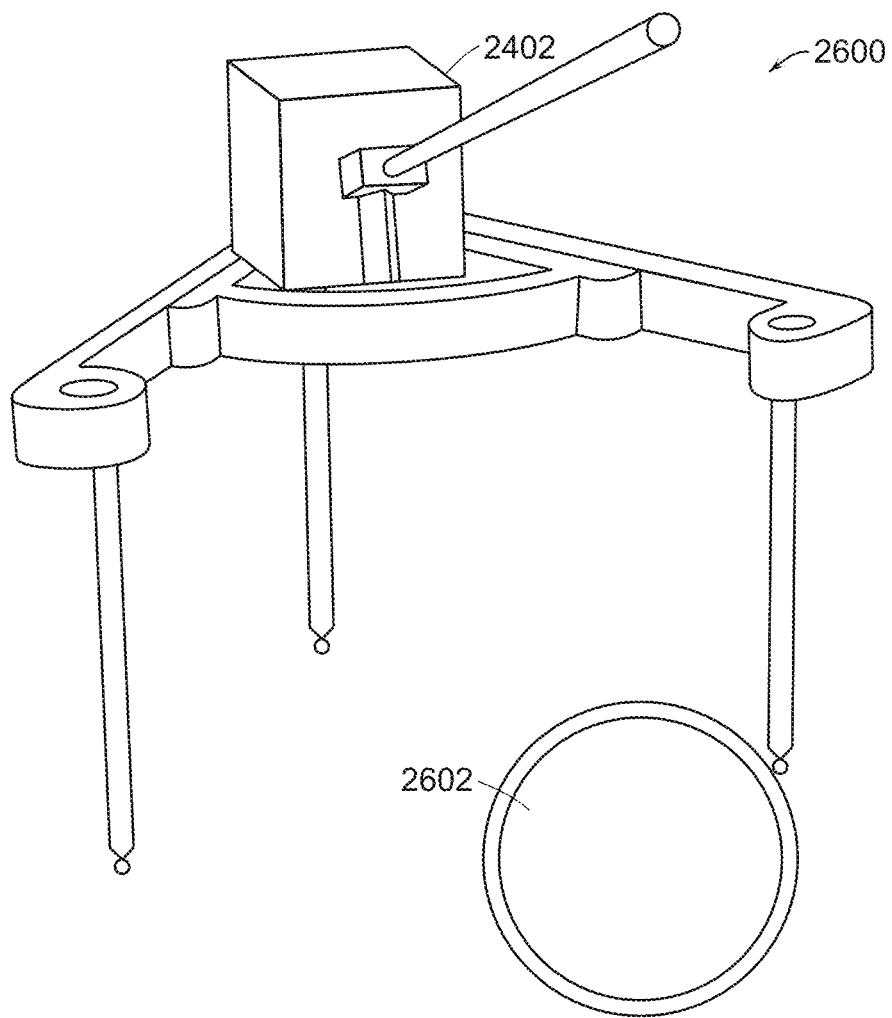
FIG. 26 is a pictorial representation of a hologram in accordance with one or more embodiments.

FIG. 26 is a pictorial representation of a hologram 2600 in accordance with one or more embodiments. The hologram 2600 may include the hologram 2402 of the HipXpert device and a hologram 2602 of the prepared cup bed as planned. However, unlike the hologram 2500 (FIG. 25), the hologram 2600 may not include a virtual representation of the patient's pelvis. During the surgical procedure, the hologram 2600 may be co-located to the corresponding physical objects either manually and/or automatically, for example by co-locating the hologram 2402 of the HipXpert device with the physical HipXpert device 2406 (FIG. 24). The surgeon may then examine the physical cup bed as prepared and see if the shape of the physical cup bed, e.g., depth and center or orientation, matches the hologram 2602 of the cup bed as planned. It may be easier for the surgeon to see and compare the physical cup bed with the hologram 2602 of the planned cup bed without a virtual representation of the pelvis as with the hologram 2500, which may interfere with the surgeon's view. Again, if the physical cup bed does not match the shape of the hologram 2602 of the planned cup bed, the surgeon may continue shaping the physical cup bed until it matches the hologram 2602.

Next, the surgeon may operate the AR device 200 to render a hologram of the cup impactor/HipXpert tool/pelvis with the cup impactor disposed at the final location for implanting the prosthetic cup component at the planned orientation and position, e.g., depth, relative to the AP Plane coordinate system. The surgeon may operate user interface elements provided by the AR device 200 to resize, move, and/or rotate the hologram of the cup impactor/HipXpert tool/pelvis so that the hologram is co-located with the physical HipXpert tool attached to the patient's pelvis. The surgeon may operate the AR device 200 to peg or anchor the hologram of the cup impactor/HipXpert tool/pelvis at that location within the operation room.

Figure 27:
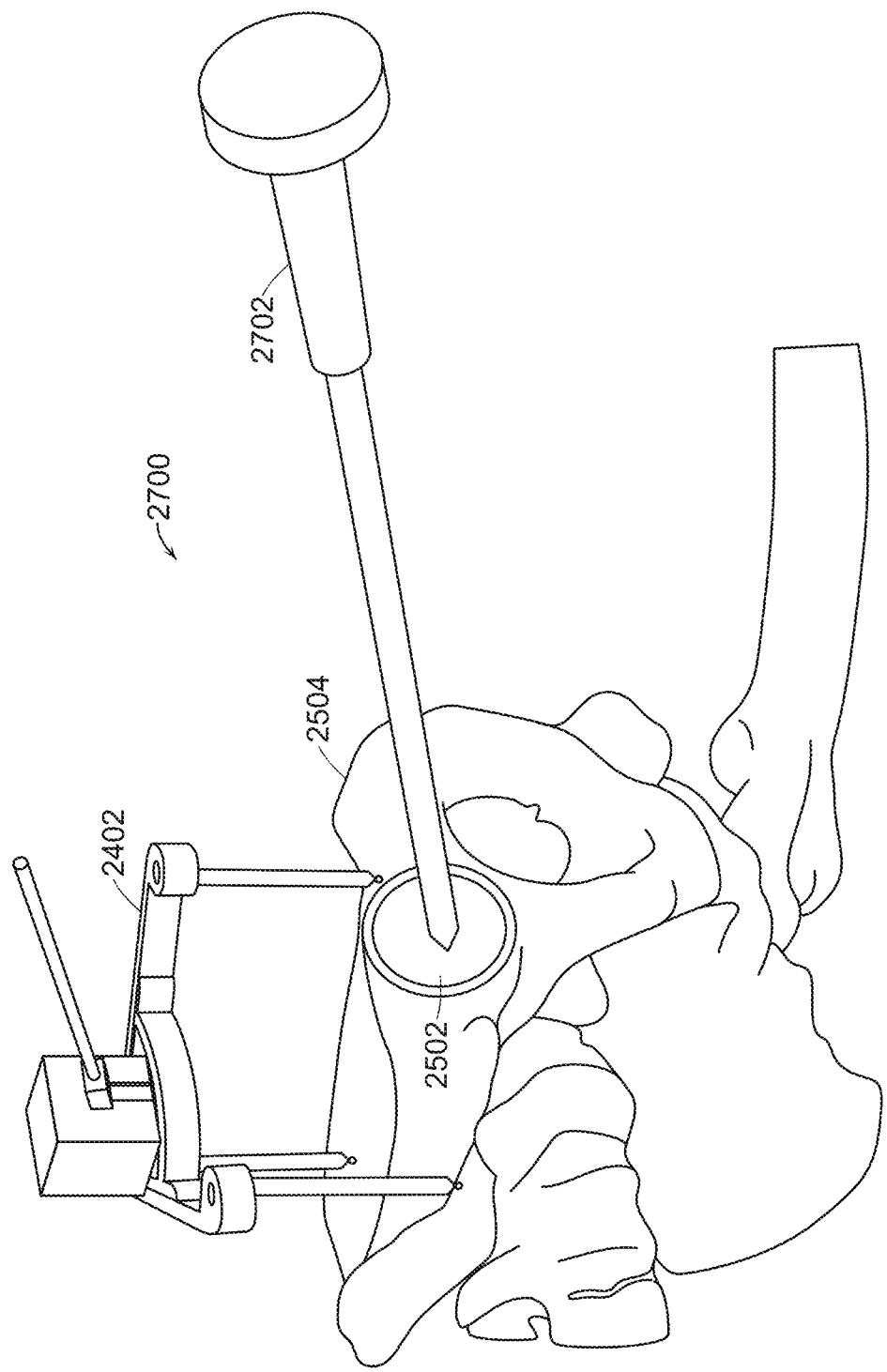
FIG. 27 is a pictorial representation of a hologram in accordance with one or more embodiments.

FIG. 27 is a pictorial representation of a hologram 2700 in accordance with one or more embodiments. The hologram 2700 may include the hologram 2402 of the HipXpert device, the hologram 2504 of the patient's pelvis, the hologram 2602 of the cup bed as planned, and a hologram 2702 of a cup impactor disposed at the final location for implanting the prosthetic cup component at the planned orientation and position. During the surgical procedure, the hologram 2700 may be co-located to the corresponding physical objects either manually and/or automatically, for example by co-locating the hologram 2402 of the HipXpert device with the physical HipXpert device.

Figure 20:
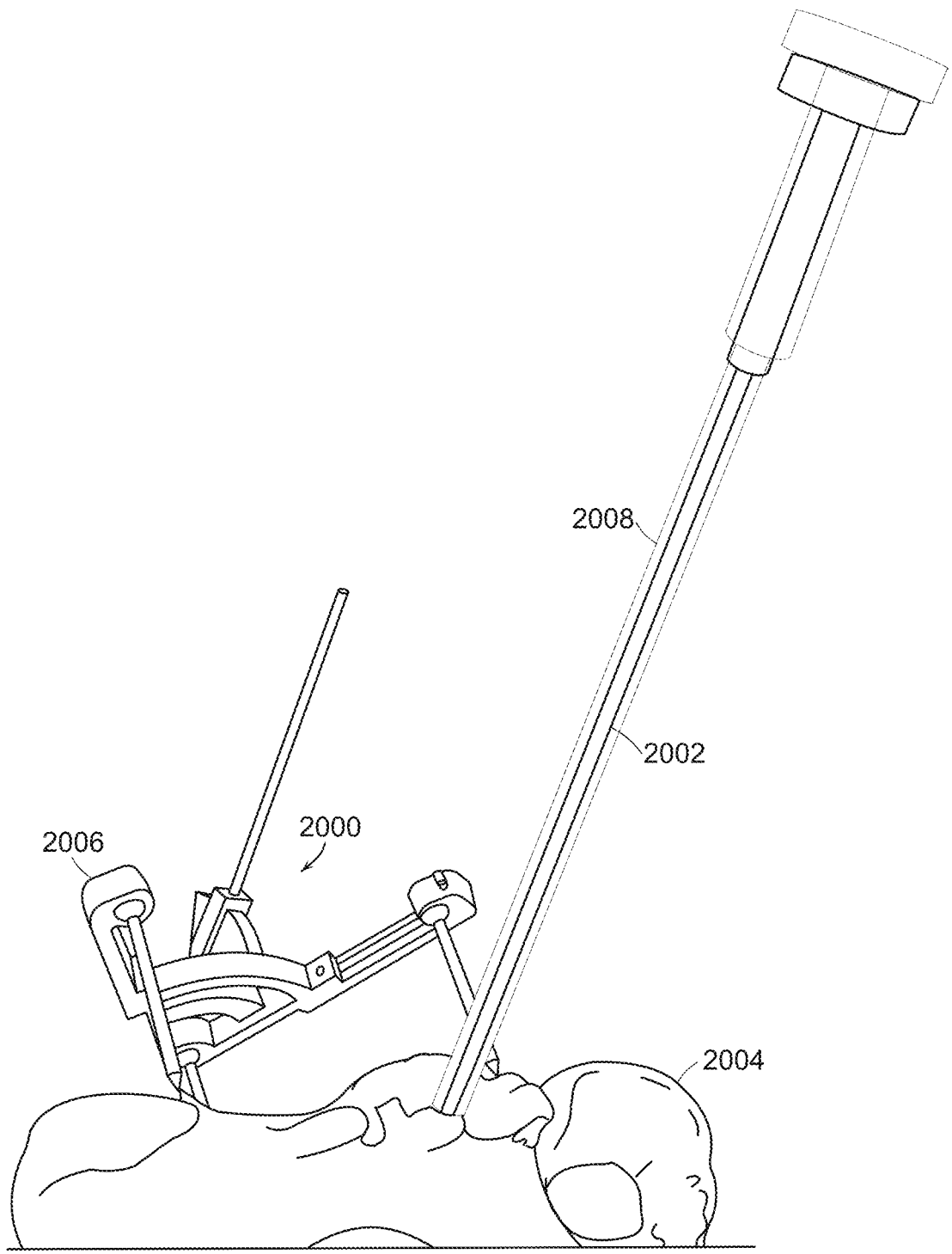
FIG. 20 is a pictorial representation of a hologram in accordance with one or more embodiments.

FIG. 20 is a pictorial representation of a hologram 2000 in accordance with one or more embodiments. The hologram 2000 may include a hologram of a pelvis 2004, a hologram of the HipXpert tool 2006, and a hologram of a cup impactor 2008. During the surgical procedure, the hologram 2000 may be positioned such that the hologram of the HipXpert tool 2006 is co-located, e.g., spatially aligned, with the physical HipXpert tool docketed to the patient's pelvis. The surgeon may then use a physical cup impactor 2002 to implant the prosthetic cup component in the cup bed. The surgeon may operate the physical cup impactor 2002 until it is co-located with the hologram 2008 of the cup impactor. When the physical cup impactor 2002 is co-located with the hologram 2008 of the cup impactor, the cup component will be positioned in the cup bed as planned, e.g., at the planned depth and orientation in the acetabulum.

Figure 55:
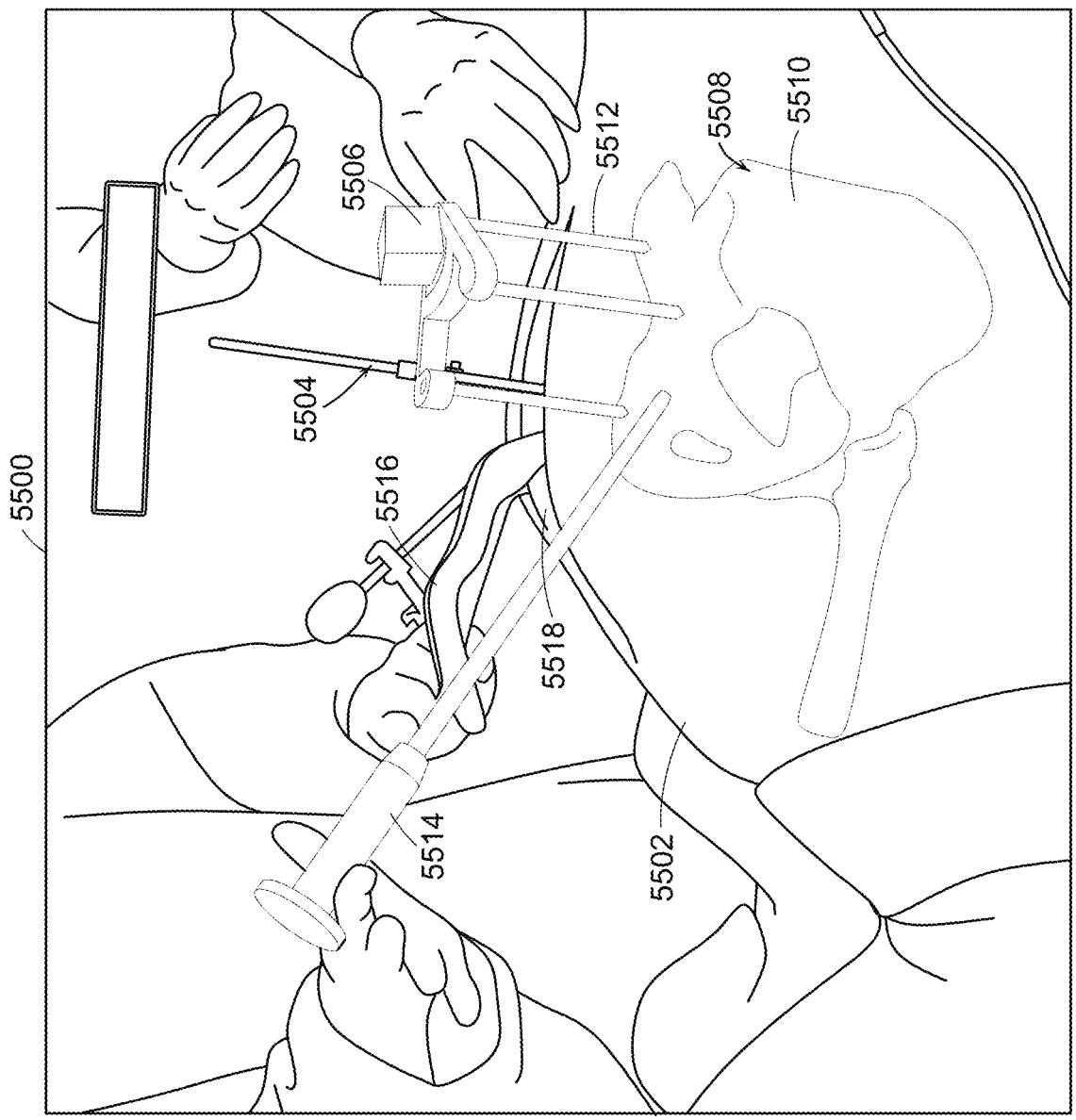
FIG. 55 is a pictorial representation of a surgical scene as viewed through an AR device in accordance with one or more embodiments.

FIG. 55 is a pictorial representation of a surgical scene 5500 as viewed through the AR device 200 in accordance with one or more embodiments. Included in the surgical scene 5500 is a patient 5502. Docked to the patient's pelvis, which is below the skin and not visible, is a three legged registration and tracking device 5504. The registration and tracking device 5504 includes a cube 5506 with QR codes on its surfaces. Also included in the surgical scene 5500 is a hologram indicated generally at 5508 as presented by the AR device 200. The hologram 5508 includes a hologram of the patient's pelvis 5510, a hologram of a registration and tracking device 5512 and a hologram of a cup impactor 5514 at a planned location for implanting a prosthetic cup component. As illustrated, the hologram of the registration and tracking device 5512 is co-located with the physical registration and tracking device 5504, e.g., through image recognition of one or more of the QR codes by the AR device 200 or object recognition of at least a portion of the registration and tracking device 5504. Accordingly, the hologram of the patient's pelvis 5510 is also co-located with the patient's pelvis. A surgeon may position a physical cup impactor 5516 in alignment, e.g., be co-located, with the hologram of the cup impactor 5514. While the hologram of the cup impactor 5514 is straight, the physical cup impactor 5516, which extends into an incision 5518 and is only partially visible, is C-shaped. With the physical cup impactor 5516 positioned in alignment with the hologram of the cup impactor 5514, the surgeon may operate the cup impactor 5516 to implant the cup component disposed at the end of the cup impactor 5516 and thus not visible (except through the incision 5518) at the planned location.

As described, the systems and methods may register the patient's pelvis during surgery with the patient in the operating room. Then, a sequence of holograms may be presented relative to the pelvis as registered. The holograms may include holograms of surgical tools at planned locations and the surgeon may line up physical surgical tools with the holograms to achieve the one or more goals of the surgery. The physical surgical tools do not themselves have to be tracked in the operating room. Nonetheless, in some embodiments, the surgical tools may be tracked, e.g., by the object tracker 1606.

In some embodiments, in addition to presenting static holograms, the AR device 200 may present a sequence of holograms in the form of a holographic movie, which may be paused and resumed by the surgeon as needed during the surgical procedure. The holographic movie may be updated, e.g., in real time, for example based on tracking of the operations of one or more surgical tools.

In some embodiments, the surgeon may operate the AR device 200 to render a hologram of the prosthetic cup component/HipXpert tool/pelvis with the hologram of the cup component at the planned orientation and location within the acetabulum. The surgeon may operate user interface elements provided by the AR device 200 to resize, move, and/or rotate the hologram of the cup component/HipXpert tool/pelvis so that the hologram is co-located with the physical HipXpert tool attached to the patient's pelvis. The surgeon may operate the AR device 200 to peg or anchor the hologram of the cup component/HipXpert tool/pelvis at that location within the operation room. The surgeon may look through the incision in the patient and compare the location and orientation of the physical cup component with the hologram of the cup component. The surgeon may determine whether the appearance of the physical cup component as implanted matches the hologram of the cup component. If not, the surgeon may reposition physical cup component until it matches the hologram of the cup component.

Figure 28:
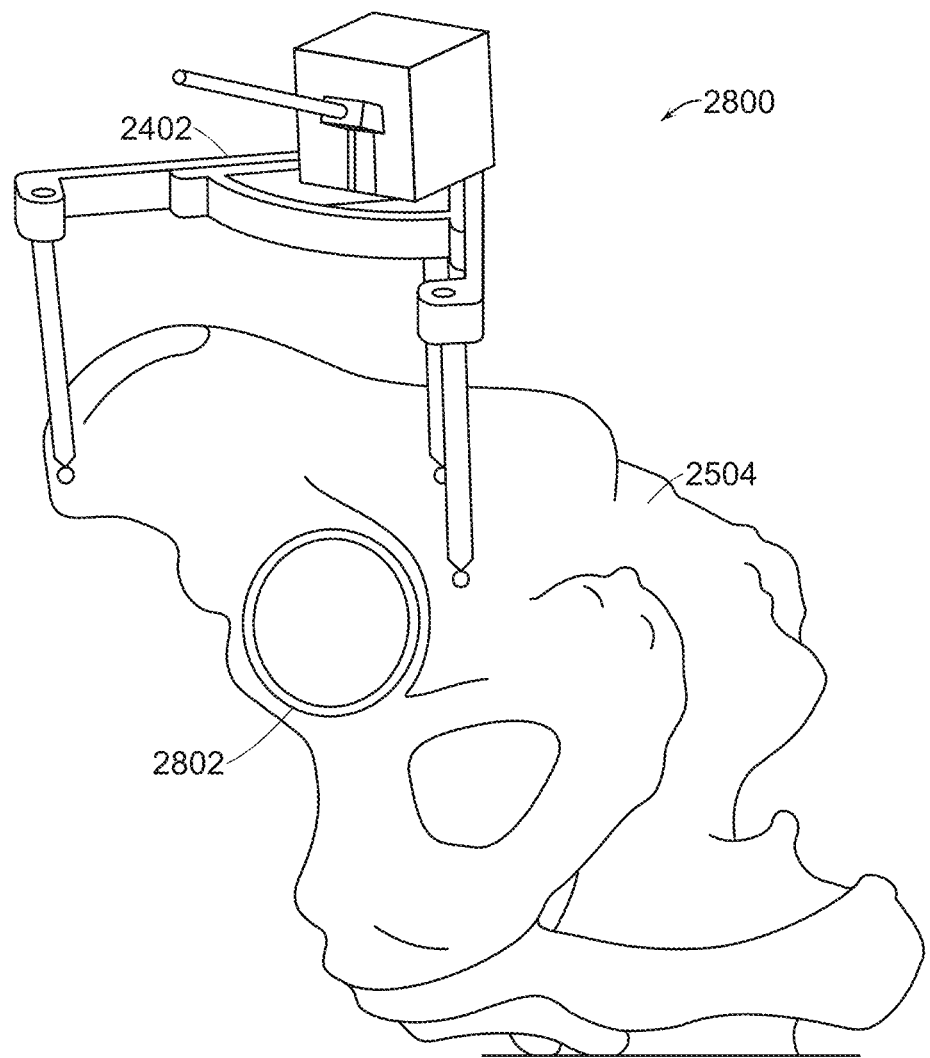
FIG. 28 is a pictorial representation of a hologram in accordance with one or more embodiments.

FIG. 28 is a pictorial representation of a hologram 2800 in accordance with one or more embodiments. The hologram 2800 may include the hologram 2402 of the HipXpert device, the hologram 2504 of the patient's pelvis, and a hologram 2802 of the cup component implanted in the patient's acetabulum as planned. During the surgical procedure, the hologram 2800 may be co-located to the corresponding physical objects either manually and/or automatically, for example by co-locating the hologram 2402 of the HipXpert device with the physical HipXpert device. The surgeon may then examine the physical cup component as implanted, e.g., through the use of the cup impactor, and see if the location and orientation of the physical cup component matches the hologram 2802 of the cup component as planned. If not, the surgeon may reposition the physical cup component, e.g., using the cup impactor, until the location of the physical cup component matches the hologram 2802.

In some embodiments, the surgeon may utilize the hologram 2800 to determine where to insert one or more screws for holding the physical cup component in place. More specifically, the surgeon may base his or her decision on where to place the one or more screws based on the hologram 2504 of the patient's pelvis. For example, the surgeon may place the one or more screws such that they are anchored securely to the patient's pelvis as indicated by the hologram 2504. For example, the cup may be planned such that the screw holes in the cup are optimally positioned to achieve the best fixation with the screws, and the surgeon may co-locate the physical cup with the hologram during surgery thereby implementing the planned best fixation.

Figure 38:
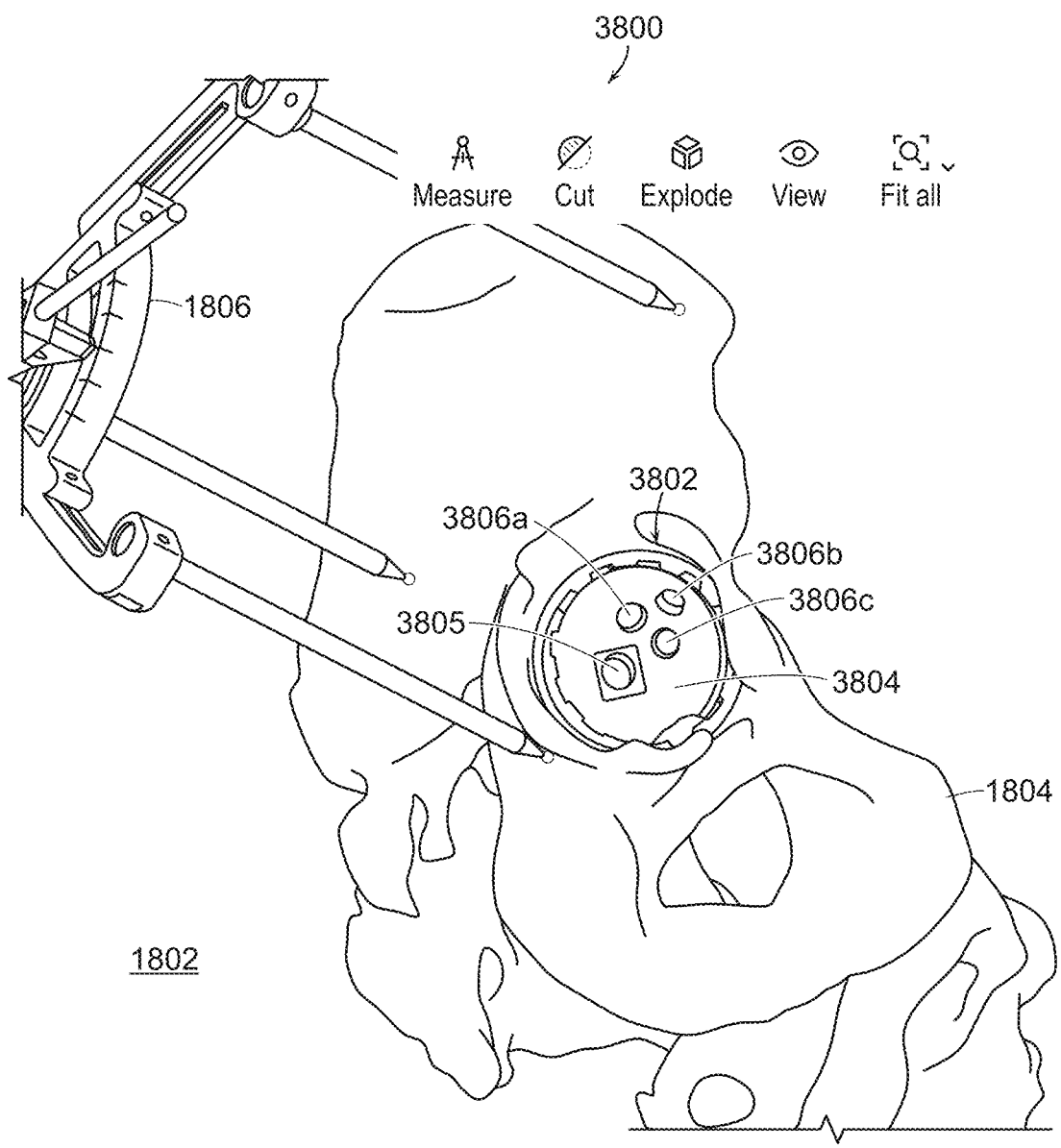
FIG. 38 is an illustration of a planning window in accordance with one or more embodiments.

FIG. 38 is an illustration of an example planning window 3800 generated by the surgical planning system 1700 and presented on the display 1718 in accordance with one or more embodiments. The planning window 3800 includes a model pane 1802 presenting a 3D model of the patient's pelvis 1804. Docketed to the model of the pelvis 1804 is a 3D model of the HipXpert tool 1806. The pelvis 1804 includes an acetabulum 3802 and disposed in the acetabulum 3802 is a shell 3804 of an acetabular cup component. The shell 3804 includes a dome hole 3805 for attaching the shell 3804 to a cup impactor and three screw holes 3806a-c for receiving bone screws for securing the shell 3804 to the acetabulum 3802. The shell 3804 may be rotated within the acetabulum 3802 thereby changing where the screws enter the pelvis. The location of the shell 3804 may be planned so that the bone screws will penetrate bone, improving fixation of the screws to the pelvis. The position of the screw holes 3806a-c also may be planned so that the bone screws do not extend beyond the bone and injure a blood vessel or other object. Here, the shell 3804 is positioned at minus 20 degrees of rotation. In this location, the anterior/inferior screw inserted in the screw hole 3806c may have to be short and may even penetrate the anteromedial inner cortex, presenting risk to vital structures of the patient.

Figure 39:
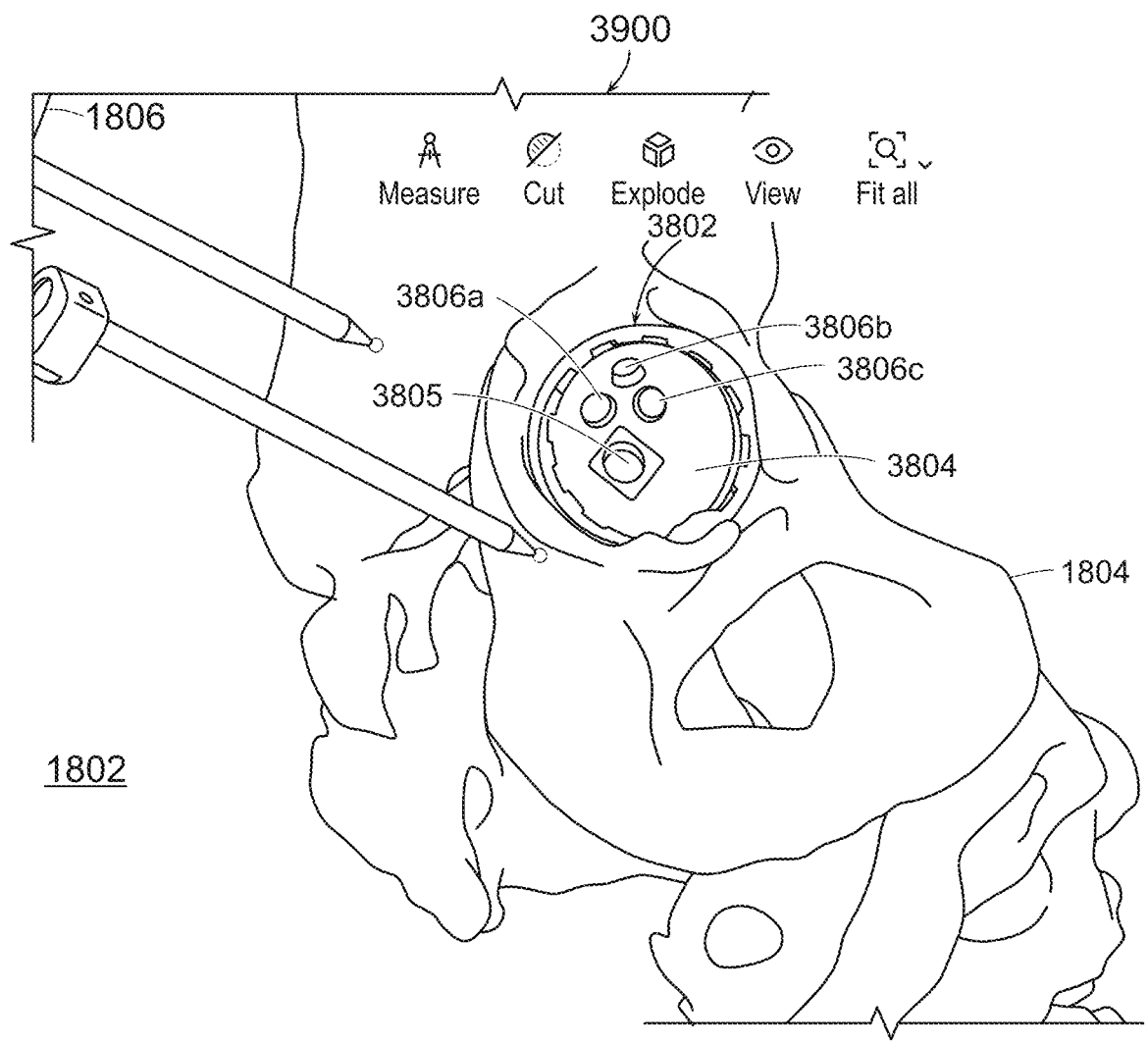
FIG. 39 is an illustration of a planning window in accordance with one or more embodiments.

FIG. 39 is an illustration of an example planning window 3900 generated by the surgical planning system 1700 and presented on the display 1718 in accordance with one or more embodiments. The planning window 3900 includes a model pane 1802 presenting a 3D model of the patient's pelvis 1804 and the HipXpert device 1806. Here, the shell 3804 is moved to a new location in the acetabulum 3802 relative to the location illustrated in FIG. 38. Specifically, the shell 3804 is positioned at plus 20 degrees of rotation. In this location, the posterior inferior screw hole 3806b is getting closer to where it might need to have a short length to avoid extending beyond the posterior wall.

Figure 40:
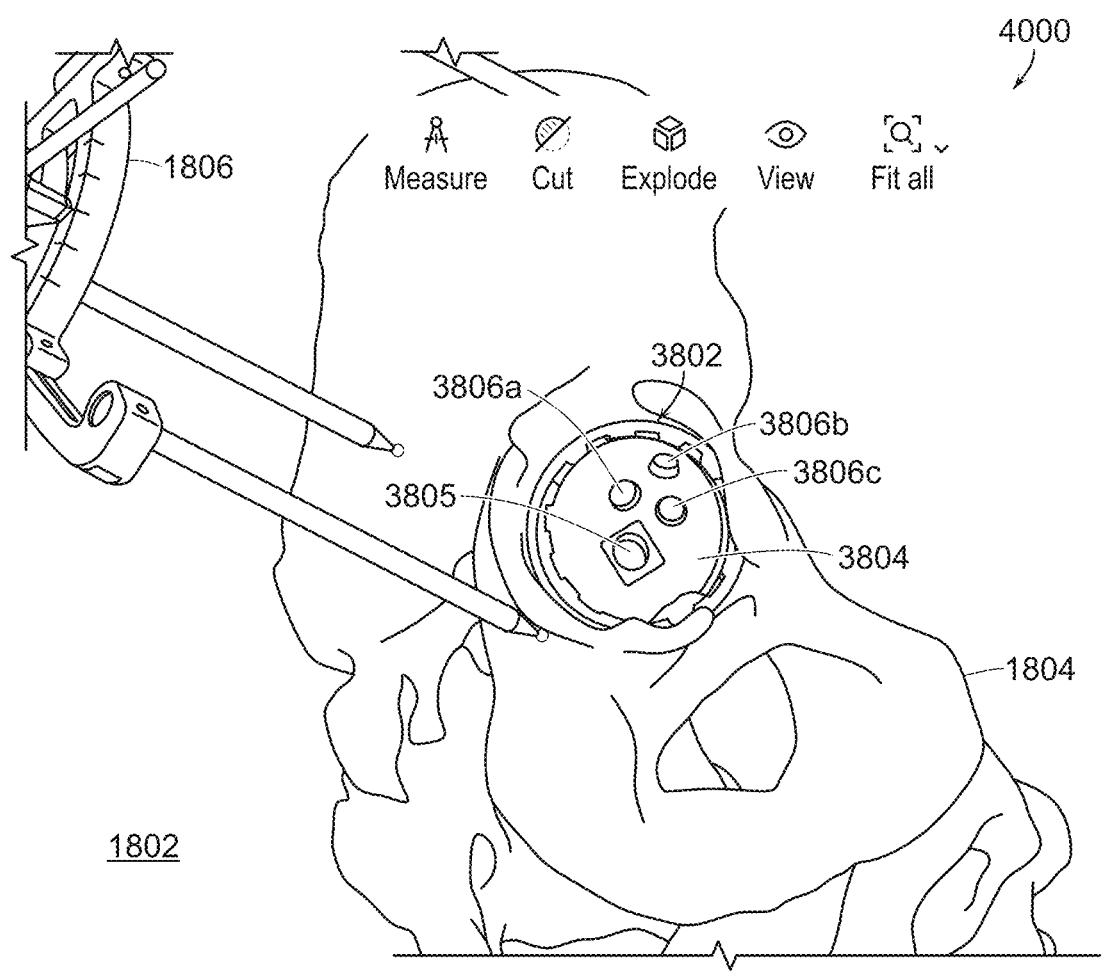
FIG. 40 is an illustration of a planning window in accordance with one or more embodiments.

FIG. 40 is an illustration of an example planning window 4000 generated by the surgical planning system 1700 and presented on the display 1718 in accordance with one or more embodiments. The planning window 4000 includes a model pane 1802 presenting a 3D model of the patient's pelvis 1804 and the HipXpert device 1806. Here, the shell 3804 is moved to a new location in the acetabulum 3802 relative to the location illustrated in FIGS. 38 and 39. Specifically, the shell 3804 is positioned at zero degrees of rotation. At this location, all of the screw holes 3806a-d are in locations that provide excellent screw length supporting strong bone fixation. Accordingly, the planner may choose zero degrees of rotation for the planned location of the shell during surgery. Furthermore, one or more holograms may be generated based on the models of the hip, the HipXpert device, and the shell as illustrated in FIG. 40. The hologram may be presented during surgery and the surgeon may align the physical shell with the shell included in the hologram so that the screw holes are in the planned locations.

In some embodiments, in addition to determining ideal locations for the screw holes of the shell, the direction and lengths of the bone screws in the screw holes may also be planned. The direction of the bone screws may be planned to maximize screw fixation and/or avoid penetrating beyond the bone or causing any injury. One or more holograms may be generated that illustrate the planned directions and lengths of the bone screws. The representation of the direction of the bone screws may be illustrated in several ways. For example, a line showing the directions may be included in the holograms and the surgeon may operate a drill to drill holes for the bone screws along these lines. In other embodiments, holograms of the bone screws at the planned directions with the tips at the screw holes may be provided. It should be understood that the planned directions of the bone screws may be illustrated in the hologram in other ways.

In some embodiments, the drilling depth for the bone screws and/or the size, e.g., length, of each bone screw may be presented in one or more holograms. For example, a hologram of a drill at the planned depth and with the drill bit in the planned direction may be presented. The surgeon may operate a physical drill so that the physical drill bit is in the planned direction and the surgeon may stop drilling when the physical drill reaches alignment with the hologram.

This approach for planning bone screws has several advantages. For example, it may reduce risk by avoiding dangerous drill trajectories, drilling too far, which might penetrate the far cortex in a dangerous location, reduce the risk of placing a screw that is too long in the wrong place, reduce risk by avoiding short screws when longer screws can be safely placed, and save time since the surgeon need not measure screw depths during the surgical procedure. It also avoids the risk of using screws that are unnecessarily short that would have poor purchase.

With the physical cup component implanted as planned, the surgeon may insert a liner into the cup component.

Figure 29:
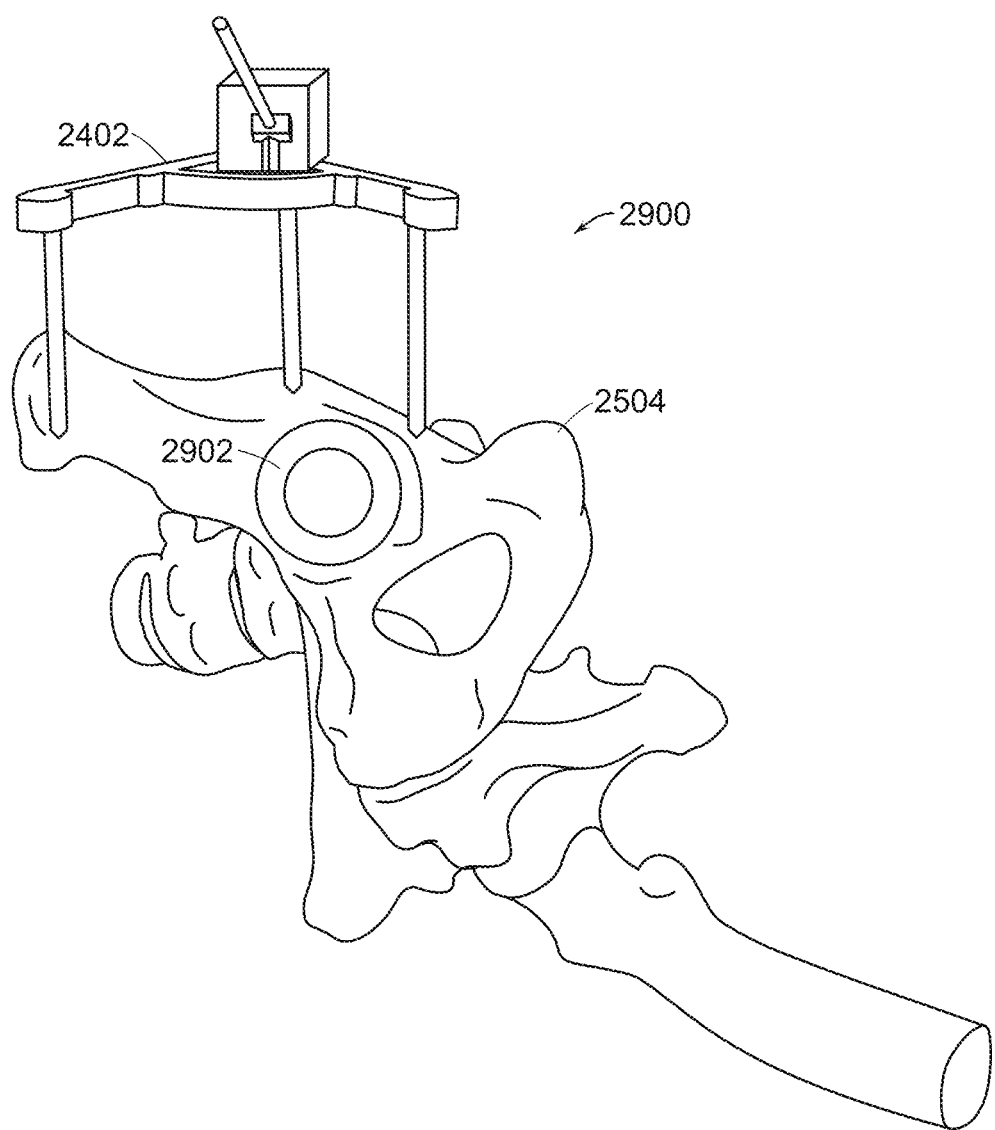
FIG. 29 is a pictorial representation of a hologram in accordance with one or more embodiments.

FIG. 29 is a pictorial representation of a hologram 2900 in accordance with one or more embodiments. The hologram 2900 may include the hologram 2402 of the HipXpert device, the hologram 2504 of the patient's pelvis, and a hologram 2902 of the cup component with liner implanted in the patient's acetabulum as planned. During the surgical procedure, the hologram 2900 may be co-located to the corresponding physical objects either manually and/or automatically, for example by co-locating the hologram 2402 of the HipXpert device with the physical HipXpert device. The surgeon may then examine the physical cup component with liner as implanted and see if the location and orientation of the physical cup component with liner matches the hologram 2902. If not, the surgeon may reposition the physical cup component and/or the liner until its location matches the hologram 2902.

Predicted Range of Motion and Impingement.

Preoperatively, the placement of the components and the trimming of specific osteophytes can be planned. In addition, range of motion of the hip joint with the planned components and the planned locations may be simulated and the composite range of motion (in all directions) until some type of impingement occurs may be calculated. This could be bone femur-bone pelvis, implant femur-bone pelvis, bone femur-implant pelvis, or implant femur-implant pelvis impingement.

During surgery, once the physical cup is implanted and the physical osteophytes removed, the AR device 200 may perform object recognition of the cup to determine the exact placement of the cup relative to the pelvis. The AR device 200 may determine where the physical cup and/or other implants are, and may further determine the shape of the bone after osteophyte trimming. The AR device 200 may then update the 3D surface model(s) of the pelvis and calculate a range of motion to impingement based on the location of the cup and/or other implants as implanted.

During the procedure, the surgeon may check that the physical HipXpert tool is still in alignment with the anchored hologram of the HipXpert tool. If the surgeon sees that the physical HipXpert tool is no longer co-located with the hologram of the HipXpert tool, the surgeon may reposition the hologram including the hologram of the HipXpert tool to co-locate the hologram with the physical HipXpert tool and/or may reposition the patient so that the physical HipXpert tool is co-located with the hologram that includes the hologram of the HipXpert tool. In some embodiments, the navigation system 1600 may keep the hologram co-located with the physical HipXpert tool automatically, for example using methodologies such as image or object recognition.

In some prior art surgical navigation systems, a surgeon needs to look away from the surgical site to a display in order to monitor the tracking of surgical tools. An advantage of the present disclosure is that the surgeon can keep his eyes trained on the surgical site while tracking one or more surgical tools.

In some embodiments, the surgeon may attach one or more tracking devices to the patient. For example, the surgeon may attach a weathervane type device or an object with one or more QR codes to the patient's pelvis. The surgeon may operate the AR device 200 to render a hologram of the one or more tracking devices, e.g., the weathervane, the HipXpert tool, and the pelvis. The surgeon may operate user interface elements provided by the AR device 200 to resize, move, and/or rotate the hologram of the weathervane/HipXpert tool/pelvis so that the hologram is co-located with the physical HipXpert tool attached to the patient's pelvis. The surgeon may operate the AR device 200 to peg or anchor the hologram of the weathervane/HipXpert tool/pelvis at that location within the operating room. The surgeon may adjust the physical weathervane until it is co-located with the hologram of the weathervane. Once the physical weathervane is co-located with the hologram of the weathervane, the surgeon may secure or fix the physical weathervane at that location. The surgeon may then remove the physical HipXpert device from the patient's pelvis. The surgeon may utilize the physical weathervane and/or the hologram of the weathervane to implant the prosthetic cup component at the planned orientation and location. For example, the weathervane (physical or hologram) may have an indicator that points along the planned orientation for the central axis of the prosthetic cup component. The surgeon may use the weathervane (physical or hologram) as a guide to implant the prosthetic cup component at the planned orientation and/or location.

In some embodiments, the weathervane or a QR cube may be randomly positioned space in the operating room. The systems and methods could regenerate new holograms on the fly that show representations of those objects by scanning where they are relative to other objects.

One or more of the holograms described herein may include the weathervane, which may be used as the registration tool in place of or in addition to the HipXpert tool.

With the cup component implanted at the planned location, e.g., depth and orientation, the surgeon may continue with the surgical procedure. For example, the surgeon may reduce the hip joint and close the incision. In other cases, the surgeon may remove the femoral head, implant a prosthetic stem, reduce the hip joint, and close the incision.

In some embodiments, the AR device 200 may utilize object detection to detect the cup component as implanted at the patient's acetabulum. In some embodiments, the cup component may include a notch or other physical feature from which its orientation may be determined by the AR device 200. The AR device 200 may register the pelvis based on the location of the cup component as detected. The AR device 200 may then utilize the cup component to anchor one or more holograms as planned relative to the pelvis. In some embodiments, once the AR device 200 detects the cup component, the HipXpert device may be removed. In other embodiments, registration of the pelvis may be transferred from the cup component to another object such as a tracker attached to the patient's pelvis. Thus, the AR device 200 may continue to anchor holograms as planned even if the cup component is no longer in view.

Automated Image Recognition: Example QR Code

In the described embodiments, a surgeon wearing the AR device 200 may manually register one or more of the holograms to corresponding objects in the operating room, such as the HipXpert tool.

In some embodiments, the object recognizer 1602 may be configured to detect and track an image, such as a barcode, which may be a two dimensional (2D) Quick Response (QR) code. For example, a QR code tracking tool is available in the Windows Mixed Reality driver for immersive VR HMDs, such as the HoloLens HMD with the VuForia Engine. The object recognizer 1602 may incorporate and/or utilize the Windows Mixed Reality driver for immersive (VR) HMDs In some embodiments, one or more QR codes may be added to and/or incorporated into a registration and tracking tool, such as the HipXpert tool. The one or more QR codes may be arranged in a predetermined geometric relationship relative to the HipXpert tool. For example, a three-dimensional (3D) shape, such as a cube, may be mounted on the HipXpert tool and one or more QR codes may be placed and/or formed on the respective sides or faces of the cube. The object recognizer 1602 may detect at least one of these QR codes, such as the QR code on the side of the cube that faces the AR device 200. Other 3D shapes that may be used include pyramids, triangular prisms, cuboids, etc.

Figure 21:
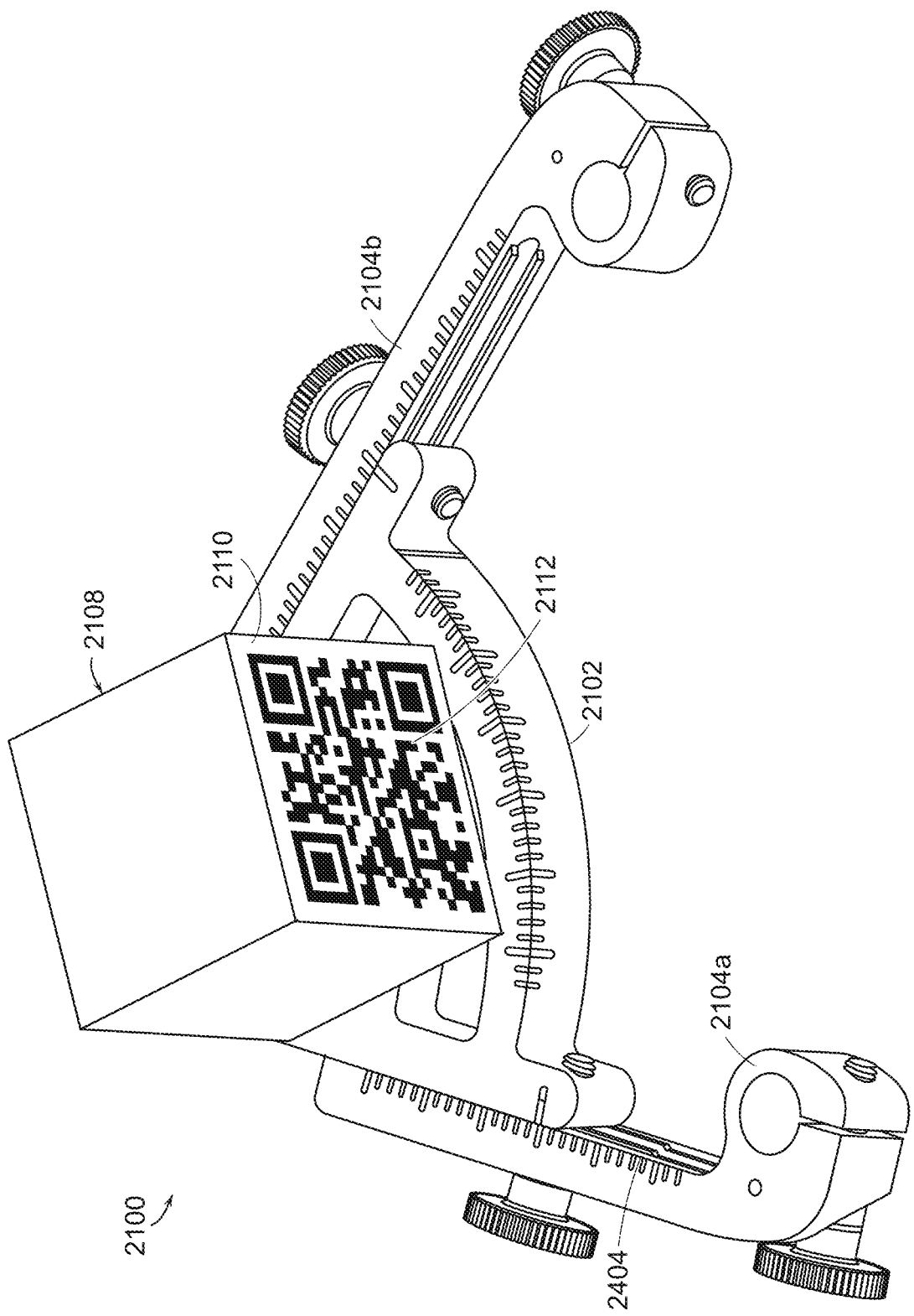
FIG. 21 is a pictorial representation of a portion of a registration and tracking tool in accordance with one or more embodiments.

FIG. 21 is a pictorial representation of a portion of a registration and tracking tool 2100 in accordance with one or more embodiments. The tool 2100 may be a HipXpert tool with the compass and guide elements removed. The tool 2100 includes a hub 2102 and two arms 2104*a* and 2104*b* adjustably extending from the hub 2102. The tool 2100 further includes three (3) legs (not shown) that extend perpendicularly from a nominal plane defined by the hub 2102 and the two arms 2104*a* and 2104*b*. A first leg extends from the hub 2102 and second and third legs extend from ends of the two arms 2104*a* and 2104*b*. Mounted on the hub 2102 opposite the legs is a cube 2108. The cube 2108 may include a front surface 2110 carrying a QR code 2112. In some embodiments, QR codes may be placed on more than one side of the cube 2108, such as all but the side used to mount the cube 2108 to the hub 2102, e.g., the bottom side. In addition, the object recognizer 1602 may detect the QR code on the side of the cube 2108 that most closely faces the AR device 200. In some embodiments, the object recognizer 1602 may detect more than one QR code simultaneously to improve registration and/or tracking accuracy.

As described, the nominal plane of the defined by the hub 2102 and the two arms 2104*a* and 2104*b* may be parallel to the plane defined by the tips of the three legs. When docked to a pelvis, the tips of the three legs may define a patient-specific ipsilateral hemipelvic plane having a known geometric relationship to the AP Plane coordinate system for the pelvis. The nominal plane defined by the hub 2102 and the two arms 2104*a* and 2104*b* thus also has a known geometric relationship to the AP Plane coordinate system and/or to any other patient-specific coordinate systems chosen to be defined. Similarly, the cube 2108 is positioned on the tool 2100 to provide a known geometric relationship between the front surface 2110 of the cube 2108 which carries the QR code 2112.

A 3D model of the tool 2100 including the cube 2108 and the QR code 2112 may be generated.

Figure 22:
FIG. 22 is a perspective view of a portion of a 3D model of a tool in accordance with one or more embodiments.

FIG. 22 is a perspective view of a portion of a 3D model 2200 of a registration and tracking tool in accordance with one or more embodiments. The 3D model 2200 corresponds to the physical registration and tracking tool 2100 including the cube 2108 having the QR code 2112.

In some embodiments, the model of the registration and tracking tool used in the pre-operative planning stage may correspond to the 3D model 2200. Similarly, the physical registration and tracking tool used during the surgical procedure may correspond to the physical registration and tracking tool 2100. The file(s) of the 3D model 2200 of the tool may be exported to a form from which the AR device 200 may generate one or more holograms.

During the surgical procedure, the object recognizer 1602 may search image or other data captured by the AR device 200 for the QR code(s) on the physical registration and tracking tool 2100. Upon detecting a QR code, the object recognizer 1602 may automatically co-locate, e.g., spatially align, the hologram of the registration and tracking tool with the physical registration and tracking tool with the QR code. Once the hologram has been co-located with the physical registration and tracking tool 2100, the surgeon may operate the AR device 200 to peg or anchor the hologram. In this way, the surgeon need not manually co-locate the holograms to the corresponding physical objects/devices. In some embodiments, when the application on the AR device 200 opens, the surgeon may identify, e.g., point to, a folder created for the patient that includes all planned holograms in the sequence of the procedure. When the AR device 200 identifies the QR code, a first hologram from the folder may be displayed in the right scale, position, and orientation. It should be understood that one or more of the holograms do not need to include the registration and tracking device itself, e.g., the HipXpert device. However, by including the HipXpert tool and the QR cube in the holograms, there is a constant visual confirmation to the surgeon that the anchoring is correct, e.g., because the physical HipXpert tool and the QR code, which sit outside of the patient's body, are co-located with the virtual images of those objects in the hologram.

In some embodiments, one or more applications (apps) may be created and loaded on the AR device 200. The app may include a planning application for running a surgical plan created for a patient and a navigation application for detecting a QR code and/or other object and presenting one or more virtual images, e.g., holograms. The app may be controlled through user interface elements provided the AR device 200, such as hand gestures for opening and interfacing with applications. In other embodiments, a surgeon may control and/or operate the app using verbal commands. For example, in response to a first verbal command, e.g., "load", the app may automatically open a file explorer window. The surgeon can then select a hologram file in a subfolder with a hand gesture. The app may automatically pick up a transformation matrix for the hologram, which may also be located in the same folder, identify the physical QR code in the surgical scene, and anchor the hologram. In other embodiments, the surgeon can use other verbal commands to cause the AR device to load and present additional holograms. Exemplary verbal commands include "hologram2", "hologram3", etc. for presenting the holograms in the planned order for the surgical procedure.

One or more components of the navigation system 1600 and/or the surgical planning system 1700 may be or may include software modules or libraries containing program instructions pertaining to the methods described herein, that may be stored on non-transitory computer readable media, and executed by one or more processors of a data processing device. In some embodiments, one or more components of the navigation system 1600 and/or the surgical planning system 1700 may each comprise registers and combinational logic configured and arranged to produce sequential logic circuits. In other embodiments, various combinations of software and hardware, including firmware, may be utilized to implement the present disclosure.

In some embodiments, one or more components of the navigation system 1600 and/or the surgical planning system 1700 may run on the AR device 200. During surgery, the surgeon may open the surgical plan using the surgical planning system 1700 running on the AR device 200. As described, the surgical plan may be updated based on the actual alteration of the acetabulum, the femur, or other bone or portion of anatomy and/or the actual placement of one or more implants.

In some embodiments, the AR device 200 may present one or more of the User Interfaces of the surgical plan in the operating room for review by the surgeon. For example, one or more of the User Interfaces may be presented on a wall or other surface of the operating room.

Transformation Matrices

Figure 36:
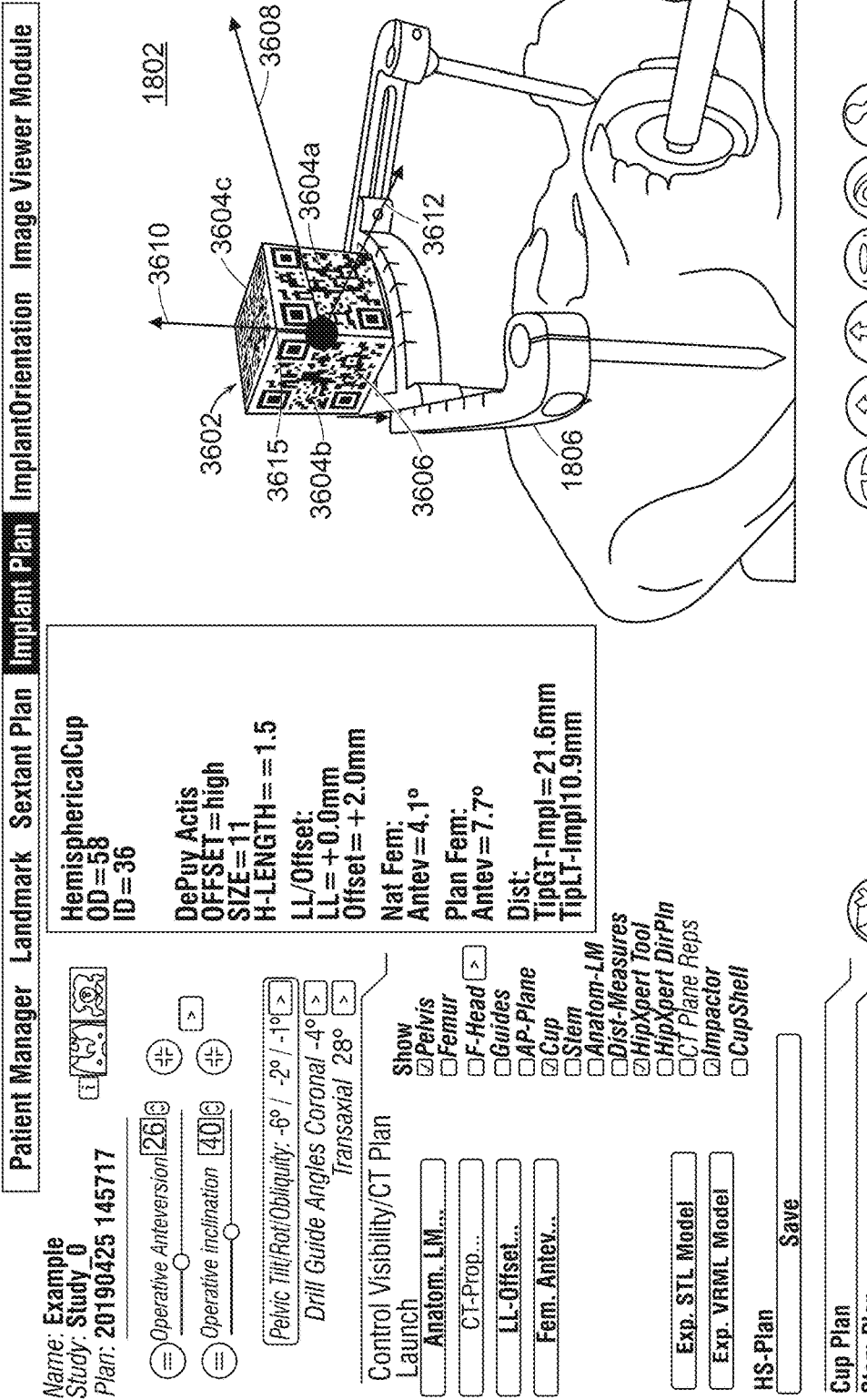
FIG. 36 is an illustration of a planning window in accordance with one or more embodiments.

FIG. 36 is an illustration of an example planning window 3600 generated by the surgical planning system 1700 and presented on the display 1718 in accordance with one or more embodiments. The planning window 3600 includes a model pane 1802 presenting a 3D model of the patient's pelvis 1804. Docketed to the model of the pelvis 1804 is a 3D model of the HipXpert tool 1806. Mounted on the HipXpert tool 1806 is a cube 3602. The cube 3602 may include a plurality of faces, e.g., surfaces, carrying one or more QR codes, such as a front surface 3604*a*, a side surface 3604*b*, and a top surface 3604*c*. One or more coordinate systems may be established for the cube 3602. In some embodiments, a coordinate system may be established at the center of the cube 3602. For example, an origin, indicated at 3606 may be located at the center of the cube 3602 and x, y and z axes 3608, 3610 and 3612 may be defined relative to the origin 3606. The x, y and z axes 3608, 3610 and 3612 may be aligned with, e.g., by parallel to, respective edges of the cube 3602.

In addition, each QR code may expose a spatial coordinate system that is aligned with the QR code, for example at the top left corner of the finder pattern. As an example, the QR code 3604*b* may expose a spatial coordinate system indicated at 3615. It should be understood that the other QR codes may expose their own spatial coordinate systems. It should be understood that the spatial coordinate systems associated with the QR codes may be aligned at other locations besides the top left corner, such as the center of the QR codes, among other locations.

Because the cube 3602 is mounted on the HipXpert device 1806 and the HipXpert device 1806 is docked to the patient's pelvis, the cube 3602 is located in a fixed location in space relative to the patient's pelvis and thus relative to the AP Plane defined for the patient's pelvis (or any other chosen pelvic coordinate system). In some embodiments, the cube 3602 may always be mounted in the same way to the HipXpert device 1806 used for each patient.

In some embodiments, the planning tool 1706 generates one patient-specific transformation matrix that may be used in determining where to present the virtual images, e.g., holograms, created for a surgical procedure. For example, the planning tool 1706 may generate a patient-specific transformation matrix that determines the orientation and position of the virtual image, e.g., hologram, relative to the coordinate system established at the center of the cube 3602. In particular, the transformation matrix may specify the orientation and position of the hologram relative to the coordinate system that includes the origin 3606 and the x, y and z axes 3608, 3610 and 3612 defined for the front face 3604*a* of the cube 3602. This patient-specific transformation matrix may relate the coordinate system at the center of the cube to the random position of the patient in the CT scanner (or other image modality) from which the surface models of the patient's anatomy are generated.

In addition, a transformation matrix may be defined that relates the spatial coordinate system associated with each QR code to the coordinate system established at the center of the cube 3602. Because it is a cube, these transformation matrices may all be the same.

As described herein, during the surgical procedure, the AR device 200 may detect the QR code applied to one of the faces or surfaces of the physical cube mounted on the physical HipXpert device that is docked to the patient's pelvis. The AR device 200 may utilize the transformation matrix associated with the detected QR code and the patient-specific transformation matrix to orient and position the virtual image, e.g., the hologram. The AR device 200 may anchor the hologram relative to the coordinate system at the center of the cube. In some embodiments, the patient-specific transformation matrix may be stored in the folder with the holograms. The transformation matrix or matrices associated with the QR codes may be hard coded in the application or in other embodiments may also be stored in the folder. When the AR device 200 accesses a hologram from the folder for presentation, the AR device 200 may also retrieve the patient-specific transformation matrix.

As noted, a patient-specific transformation matrix may be defined for the holograms that will be presented during a surgical procedure. This patient-specific transformation matrix may be defined relative to a selected point of the cube 3602. The selected point may be the center of the cube 3602. As noted, the cube 3602 may be mounted to the HipXpert device, which in turn is docked to the patient's pelvis in a predetermined and known location. Accordingly, the center of the cube 3602 is in a fixed and known location relative to the patient's pelvis, e.g., relative to the AP Plane (or any other pelvic coordinate system). Locations and orientations of implants, e.g., the cup component, and tools, e.g., reamers and cup impactors, may be planned for a patient, e.g., relative to the AP Plane. Geometric relationships between these planned locations and orientations and the center of the cube 3602 may be determined. During surgery, the AR device 200 may recognize one or more of the QR codes on the physical cube of the HipXpert as docked to the patient. With the location of the physical cube in space determined, the AR device 200 can then use the patient-specific transformation matrix to determine where to locate the holograms such that the holograms appear in the planned locations and orientations.

In some embodiments, one or more secondary transformation matrices may also be defined. For example, secondary transformation matrices may be defined for each of the five QR codes applied to the faces of the cube 3602, e.g., front face, left face, right face, rear face, and top face. These secondary transformation matrices may provide geometric transforms from the respective QR code to the patient-specific primary matrix defined for the center of the cube 3602. When the AR device 200 detects a QR code (the particular QR code depending on the way the surgeon happens to be viewing the HipXpert device), the AR device 200 may retrieve the secondary transformation matrix associated with the detected QR code. The AR device 200 may then utilize this secondary transformation matrix together with the patient-specific transformation matrix to orient and position the respective hologram. While the transformation matrix generated for the center of the cube 3602 may be patient-specific, the secondary transformation matrices are not patient-specific. Instead, the secondary transformation matrices are the same for each cube geometry, e.g., dimensions. Thus, assuming the same cube 3602 is being reused or a cube 3602 with the same dimensions is being used with another patient, the same secondary transformation matrices may be re-used.

In sum, just a single patient-specific transformation matrix between the orientation and position of the QR code and the orientation and position of the rest of the hologram for every hologram that is to be presented may be generated. With the present disclosure, by detecting in space a QR code (that is on a cube mounted on a HipXpert device docked to a patient's pelvis), the AR device 200 can automatically register and track the patient's pelvis and allows for the presentation of one or more co-located holograms. In particular, the tips of the legs of the HipXpert device when docked to a patient's pelvis may define a hemi-pelvic ipsilateral reference plane having a known geometric relationship to the AP Plane. Furthermore, the frame of the HipXpert device from which the legs extend may be parallel to this hemi-pelvic ipsilateral reference plane (and thus have a known geometric relationship to the AP Plane). The cube which carries the one or more QR codes may be mounted on this frame. Accordingly, by detecting a QR code, the pelvis may be registered and tracked.

Figure 37:
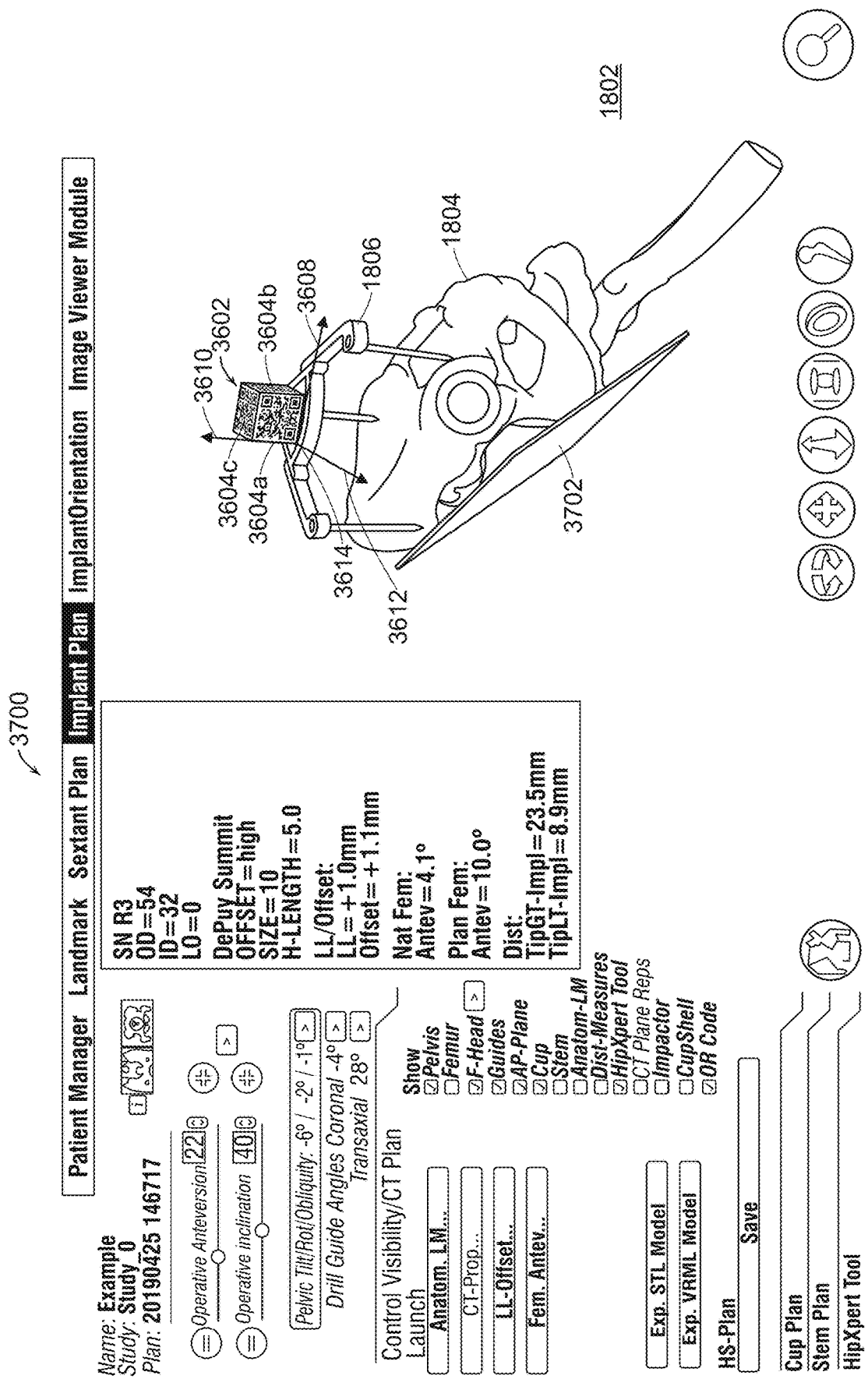
FIG. 37 is an illustration of a planning window in accordance with one or more embodiments.

FIG. 37 is an illustration of an example planning window 3700 generated by the surgical planning system 1700 and presented on the display 1718 in accordance with one or more embodiments. The planning window 3600 includes a model pane 1802 presenting a 3D model of the patient's pelvis 1804. Docketed to the model of the pelvis 1804 is a 3D model of the HipXpert tool 1806. Mounted on the HipXpert tool 1806 is the cube 3602. An AP Plane 3702 is defined for the pelvis 1804.

As described, the QR cube may be mounted on a central portion of the frame of the HipXpert device. Because the legs of the HipXpert device may be of fixed lengths, the location of the QR cube and thus QR code(s) is constant from one patient to another. A patient-specific transformation matrix instructs the system as to where the QR cube and QR code(s) are located in space relative to random image-space coordinate system and also the anterior pelvis plane coordinate system. This transformation matrix is then a predetermined "patient-specific pass-code". When the holograms are exported, the "key" or patient specific transformation matrix is also exported, which is used to determine where to present the holograms in space for that patient's specific surgical plan.

Cross-Section Display of Image Data Such as CT or MR Data.

As described, images of a patient such as a CT or MR study may be taken of a patient during a preoperative phase. For example, for hip surgery, a CT scan may be taken of the patient's pelvis and hips (with some images of the distal femur for coordinate system development). For knee surgery, a CT scan or MR study may be taken of the patient's knee (again, potentially with images of the hip and ankle for coordinate system development). Such image modalities create an image volume that can be displayed as sequential sliced in the original image acquisition plane, or can be displayed in any cut plane through the image volume. In fact, the display need not be a perfect plane, the image sampling could be made in any desired shape. For the purposes of this discussion the images could be generated as planar images. In addition, the image volume may be used to construct a 3D surface model, e.g., of the patient's pelvis or knee. The 3D surface model may be opened and manipulated using a CAD software environment. Pre-operative planning may be performed using the 3D surface model. For example, the 3D surface model may be used to plan the preparation of bone surfaces and the selection, location and orientation of one or more prosthetic implants.

In some embodiments, the entire image data volume such as a CT image volume for a patient or a portion thereof may be loaded onto or otherwise made accessible to the AR device 200. During surgery, the AR device 200 may display desired sub-sections of the image volume to the surgeon. For example, the AR device 200 may register the portion of the patient's anatomy being operated on using one of the registration methods described, such as the patient's pelvis or knee, and then tracked using a registration and tracking device such as a QR cube as described. The AR device 200 may then co-locate and anchor the entire image volume, such as a CT data volume, in space relative to the registration and tracking device. The system then may give the surgeon the option of seeing a portion of the image volume in space co-located with the actual location that the image data was acquired from on the patient. For example, the image volume could be cut in a planar cross-section that is perpendicular to the view of the surgeon wearing the AR device 200. That planar cross section could be determined as a fixed distance from the viewer or for example a fixed origin within the volume. For example, the surgeon, when preparing the acetabulum, may want to know the thickness of the remaining bone deep to the proposed cup placement. The origin of the cross section could be fixed at the center of the proposed placement of the acetabular component, and the displayed planar section through the volume would vary as the surgeon moves to stay perpendicular to the viewpoint of the surgeon's eyes.

For example, the CT data volume for the patient's pelvis may be co-located with the patient's pelvis in the operating room. The AR device 200 may generate one or more planar cuts through the CT data volume to produce a two dimensional (2D) CT image from the CT data. The AR device 200 may present this 2D CT image to the surgeon. The 2D CT image may be generated from a planar cut, also referred to as a cut plane, through a plurality of the slices included in the CT data volume. The planar cut through the CT data volume may be perpendicular to the surgeon's line of sight relative to the CT data volume as co-located with the patient's anatomy, e.g., the pelvis or knee. By co-locating the CT data volume with the patient, the 2D CT image, as displayed by the AR device 200, may appear to the surgeon as overlaid on and co-located with the patient's anatomy. The cut plane may be set at a predetermined distance from the AR device 200. For example, if the surgeon moves his or her head and consequently the AR device 200 closer to the patient (e.g., lying supine on the operating table), the cut plane is moved backward (posterior) through the CT data volume. Similarly, as the surgeon moves his or her head away from the patient, the cut plane moves forward (anterior) through the CT data volume. Thus, by simply moving his or her head, the surgeon can control where the cut plane is formed in the CT data volume, and thus the resulting 2D CT image generated and presented by the AR device 200.

Figure 41:
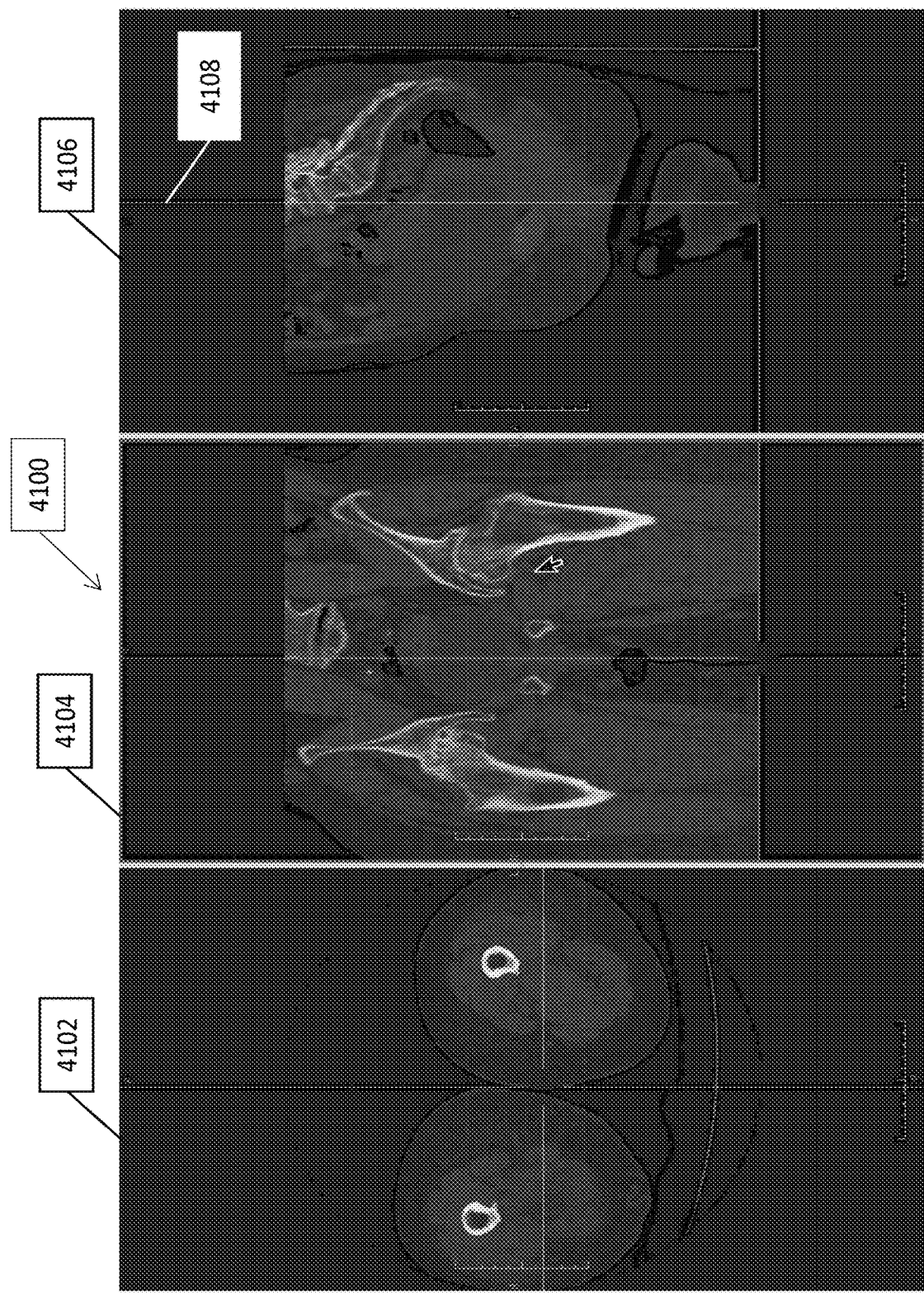
FIG. 41 is a pictorial representation of an example 2D CT image set of a patient's pelvis in accordance with one or more embodiments.

FIG. 41 is a pictorial representation of an example 2D CT image set 4100 of a patient's pelvis in accordance with one or more embodiments. The 2D CT image set 4100 may include an image 4102 through an axial plane, an image 4104 through a coronal plane, and an image 4106 through a sagittal plane. The coronal image 4104 shows the patient's left and right hip joints and a portion of the patient's spine. Suppose the patient is lying supine on an operating table, and the surgeon is looking down at the patient. The AR device 200 may generate and present a 2D CT image similar to the image 4104 through the coronal plane. The 2D CT image may be formed based on a cut plane indicated at 4108 on the sagittal image 4106 that is a predetermined distance from the AR device 200.

Now, suppose the surgeon moves his or her head away from the patient.

Figure 42:
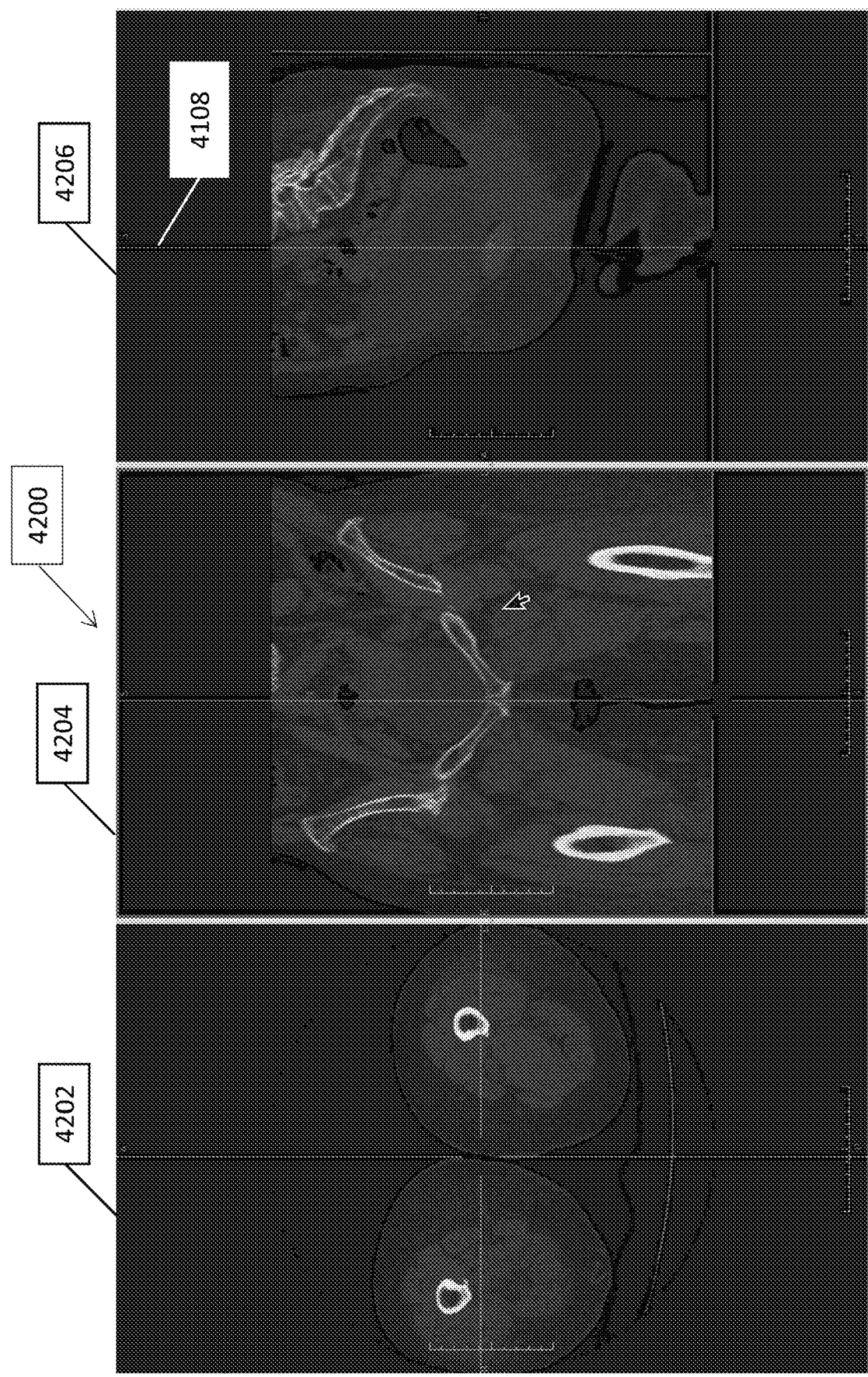
FIG. 42 is a pictorial representation of an example 2D CT image set of a patient's pelvis in accordance with one or more embodiments.

FIG. 42 is a pictorial representation of an example 2D CT image set 4200 of a patient's pelvis based on the new position of the surgeon's head in accordance with one or more embodiments. The 2D CT image set 4200 may include an axial image 4202, a coronal image 4204, and a sagittal image 4206. As illustrated, because the surgeon moved his or her head away from the patient, the cut plane 4208, which remains a fixed distance from the AR device 200, is moved anterior through the CT data. The coronal image 4204 is thus different than the coronal image 4104 (FIG. 41).

Now, suppose the surgeon moves his or her head closer to the patient relative to the distance producing the 2D CT image set 4100 (FIG. 41).

Figure 43:
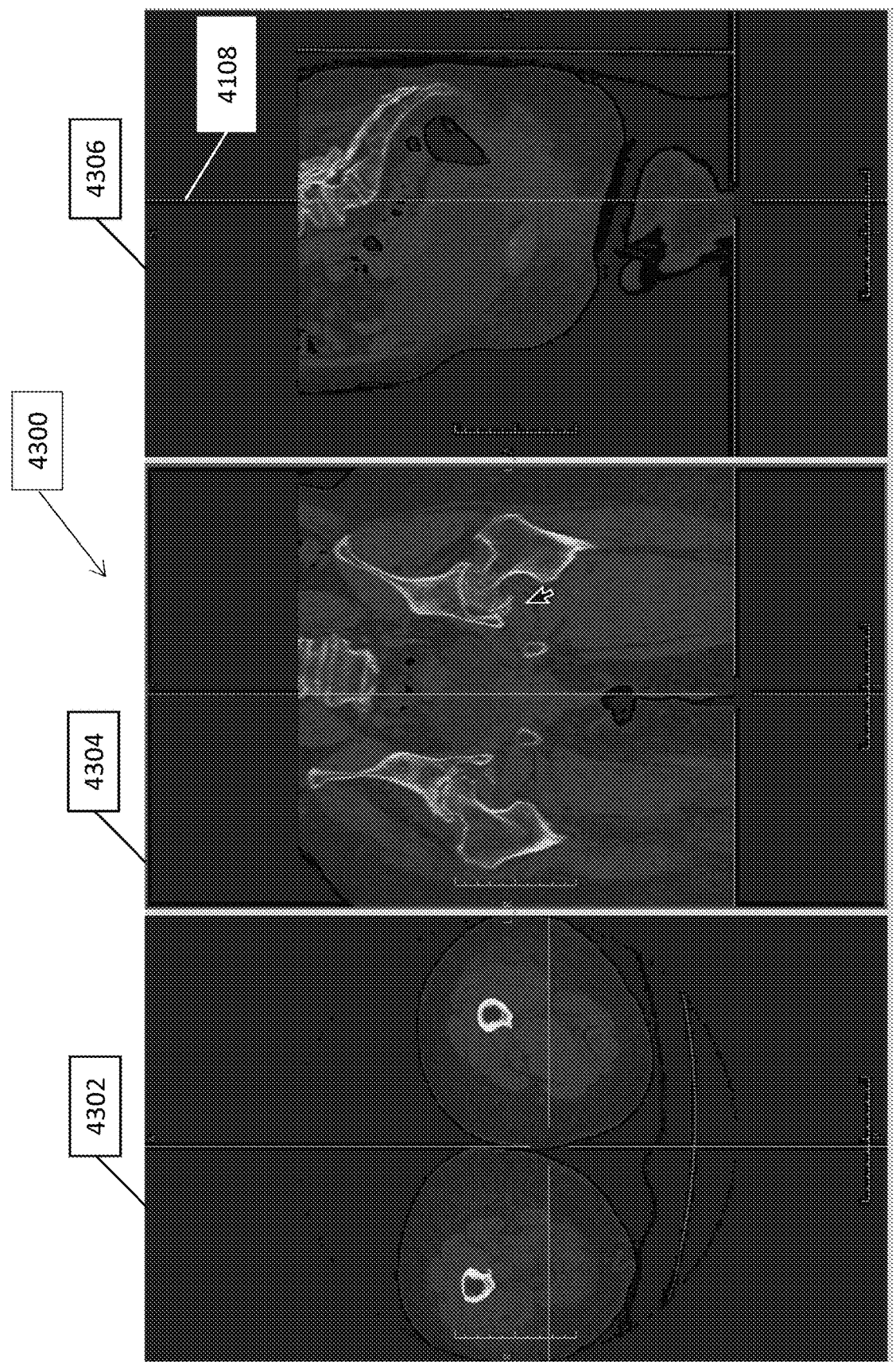
FIG. 43 is a pictorial representation of an example 2D CT image set of a patient's pelvis in accordance with one or more embodiments.

FIG. 43 is a pictorial representation of an example 2D CT image set 4300 of a patient's pelvis based on the new position of the surgeon's head in accordance with one or more embodiments. The 2D CT image set 4300 may include an axial image 4302, a coronal image 4304, and a sagittal image 4306. As illustrated, because the surgeon moved his or her head closer to the patient, the cut plane 4108, which remains a fixed distance from the AR device 200, is moved posterior through the CT data volume. The coronal image 4304 is thus different than the coronal images 4104 (FIG. 41) and 4204 (FIG. 42).

As noted, the 2D CT image generated and presented by the AR device 200 may be based on a cut plane that is a fixed distance from the AR device and perpendicular to the surgeon's line of sight. A suitable fixed distance is 50 cm for example. The 2D CT image is thus a cross-section of the CT data volume. In other embodiments, the 2D CT image data may correspond to one of the slices of the CT data volume.

In some embodiments, the AR device 200 may present one or more holograms in addition to the 2D CT image. For example, in addition to the 2D CT image, the AR device 200 may present one of the holograms including the reamer tool, the cup impactor tool, a cup component, a knee cutting jig, a knee component, etc. The presentation of one or more 2D CT images together with a hologram of a reamer may provide the surgeon with additional information, such as whether the reamer is getting close to reaming all the way through the inner wall of the patient's acetabulum. For example, while the AR device 200 presents a 2D CT image, the surgeon could intuitively determine how far the reamer has cut into the patient's acetabulum, e.g., by placing his or her finger in the wound while viewing the 2D CT image.

As the surgeon is reaming the acetabulum to prepare the cup bed for receiving the cup component, he or she may want to know how much bone is left behind the reamer medially, for example to avoid going through the bone. A cut plane that is along the surgeon's line of sight while reaming would provide this information. In some embodiments, the AR device 200 may present such a cut plane through the CT volume data. The cut plane display may be locked in position so that the surgeon may then move his or her head to observe the cut plane and thus see how much bone is left behind the reamer. In other embodiments, another medical professional in the operating room wearing an AR device 200 may observe this cut plane and inform the surgeon of how much bone is remaining.

Figure 46:
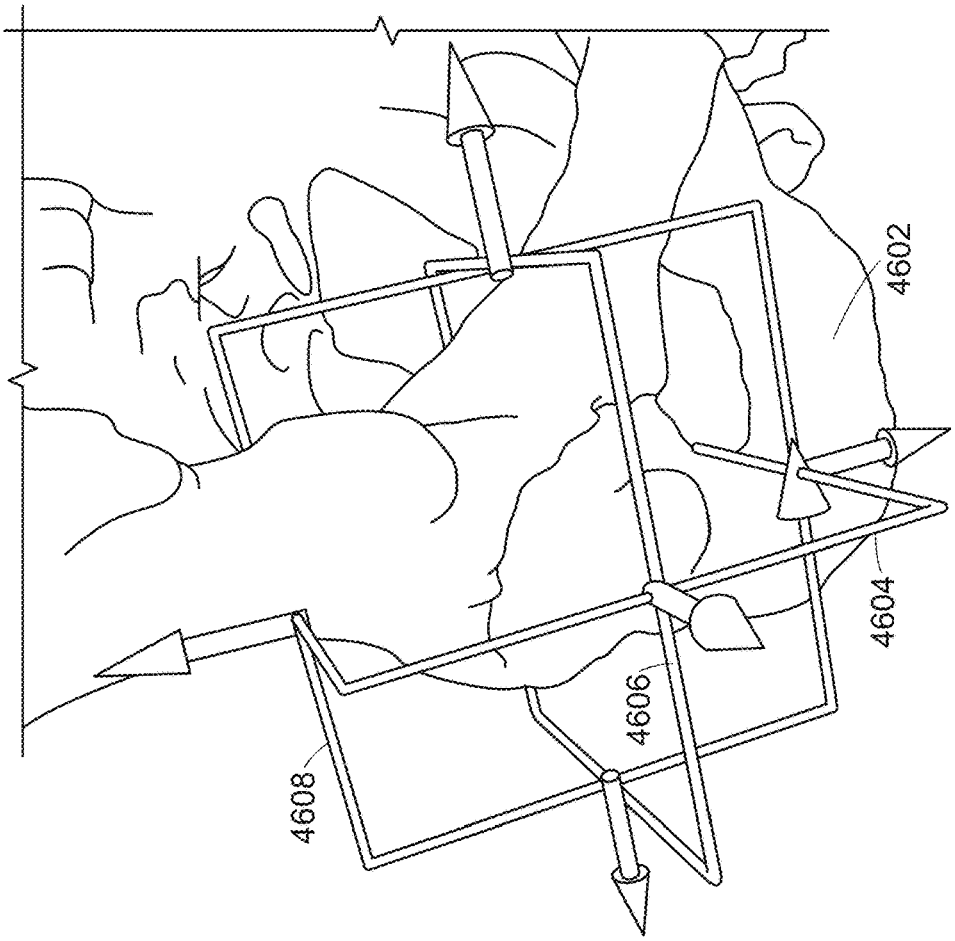
FIG. 46 is an illustration of a surface model of a pelvis with three cut planes in accordance with one or more embodiments.

FIG. 46 shows a surface model of the pelvis 4602 with 3 cut planes. The green box 4604 signifies one image-generation plane, the red box 4606 signifies a second image-generation plane, and the yellow box 4608 signifies a third image-generation plane.

Figure 47:
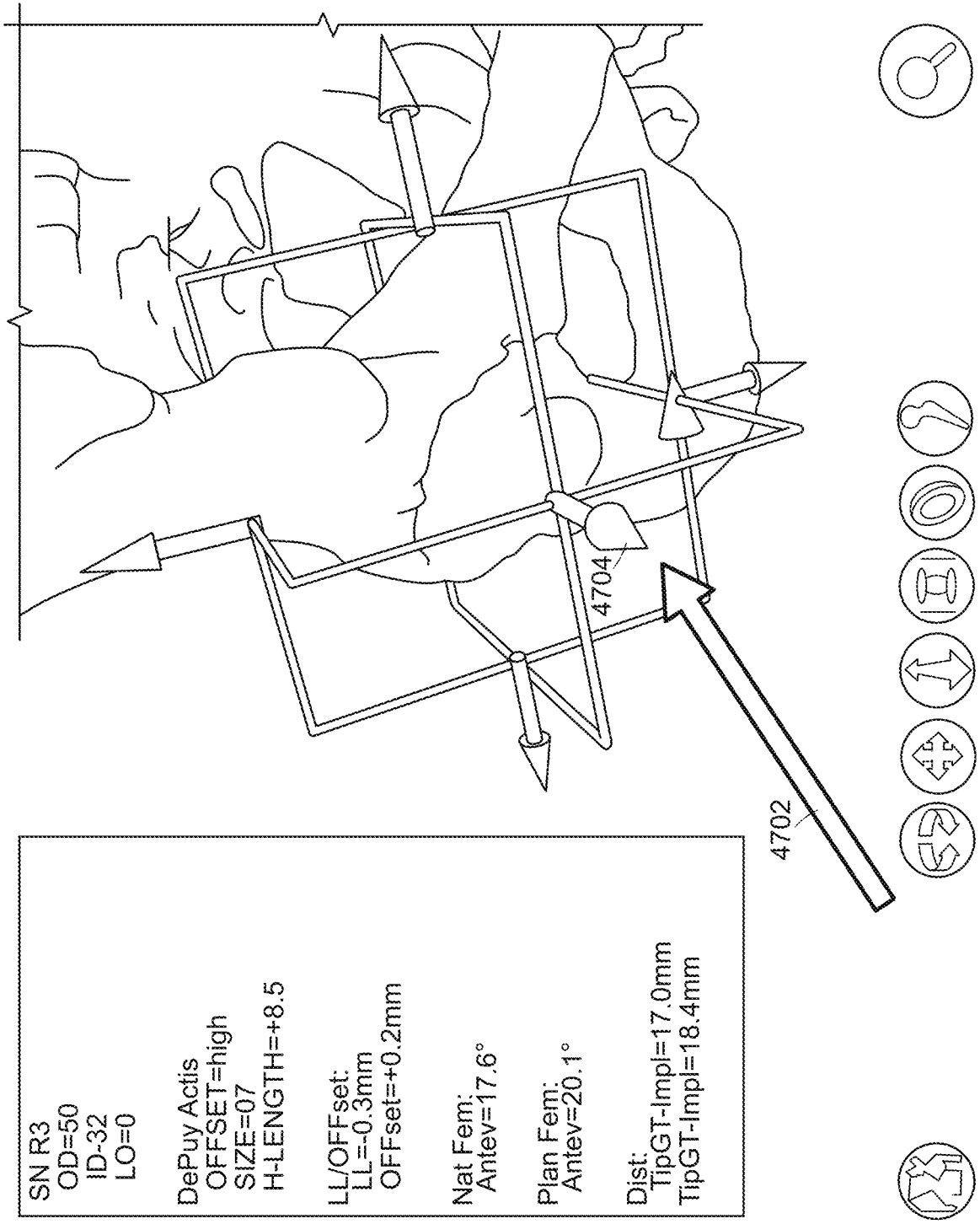
FIG. 47 is an illustration of a surface model of a pelvis with three cut planes in accordance with one or more embodiments.

FIG. 47 shows a purple arrow 4702 pointing to a particular red arrow 4704 from the same image as illustrated in FIG. 46. A surgeon might often view the hip from the perspective of the designated red arrow 4704.

Figure 48:
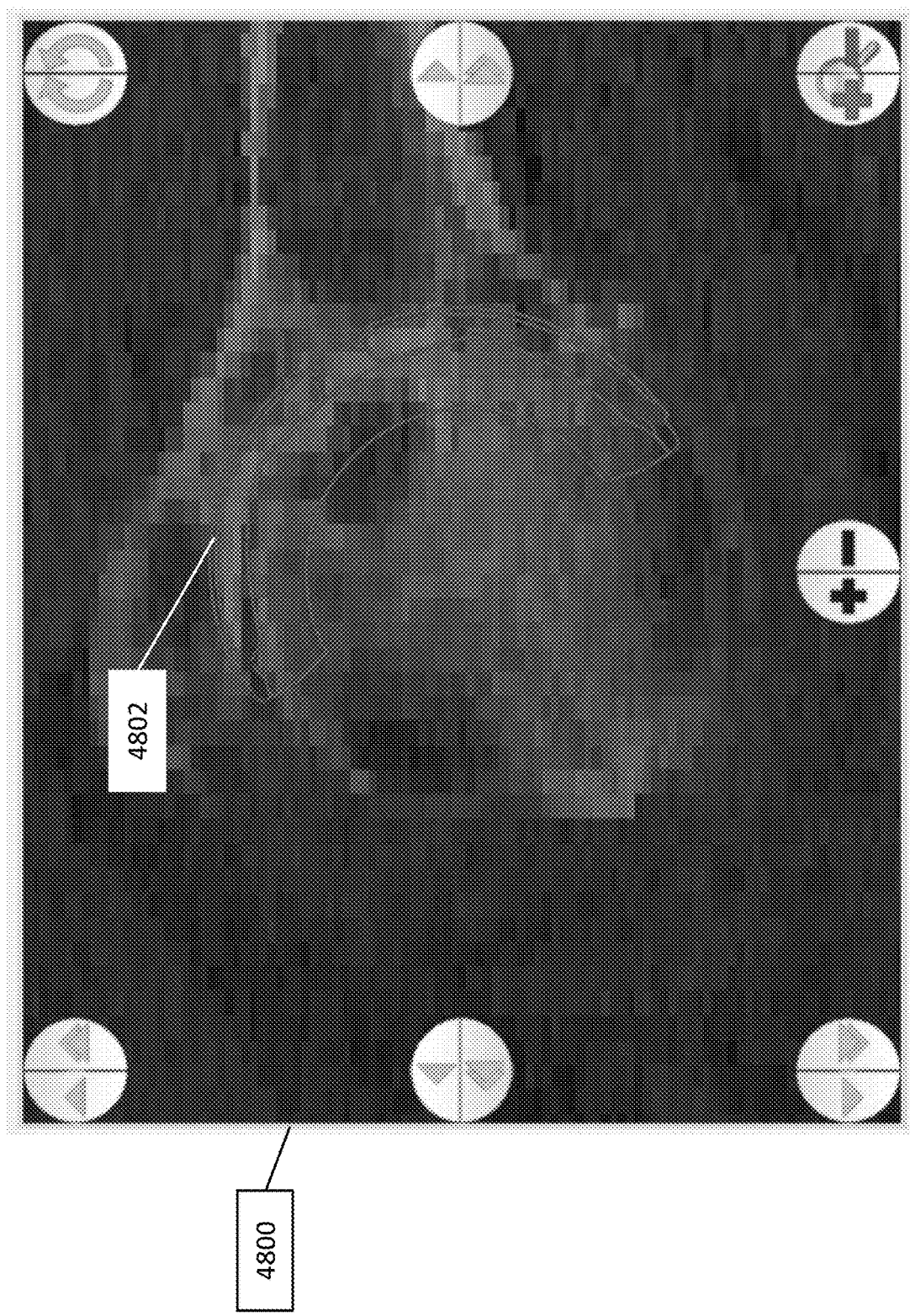
FIG. 48 is a pictorial representation of an image generated and projected by an AR device in accordance with one or more embodiments.

FIG. 48 is a pictorial representation of an image 4800 projected by the AR device 200 in the exact location within the patient's body that the data were acquired from. This image 4800 represents an image generated in the yellow box plane 4608 of FIG. 46 in that it is both perpendicular to the surgeon's viewpoint and in a plane that includes the center of the planned acetabular component. FIG. 48 also shows a cross section of the planned acetabular component indicated at 4802 that could be turned on or off depending upon the surgeon's preference.

Figure 49:
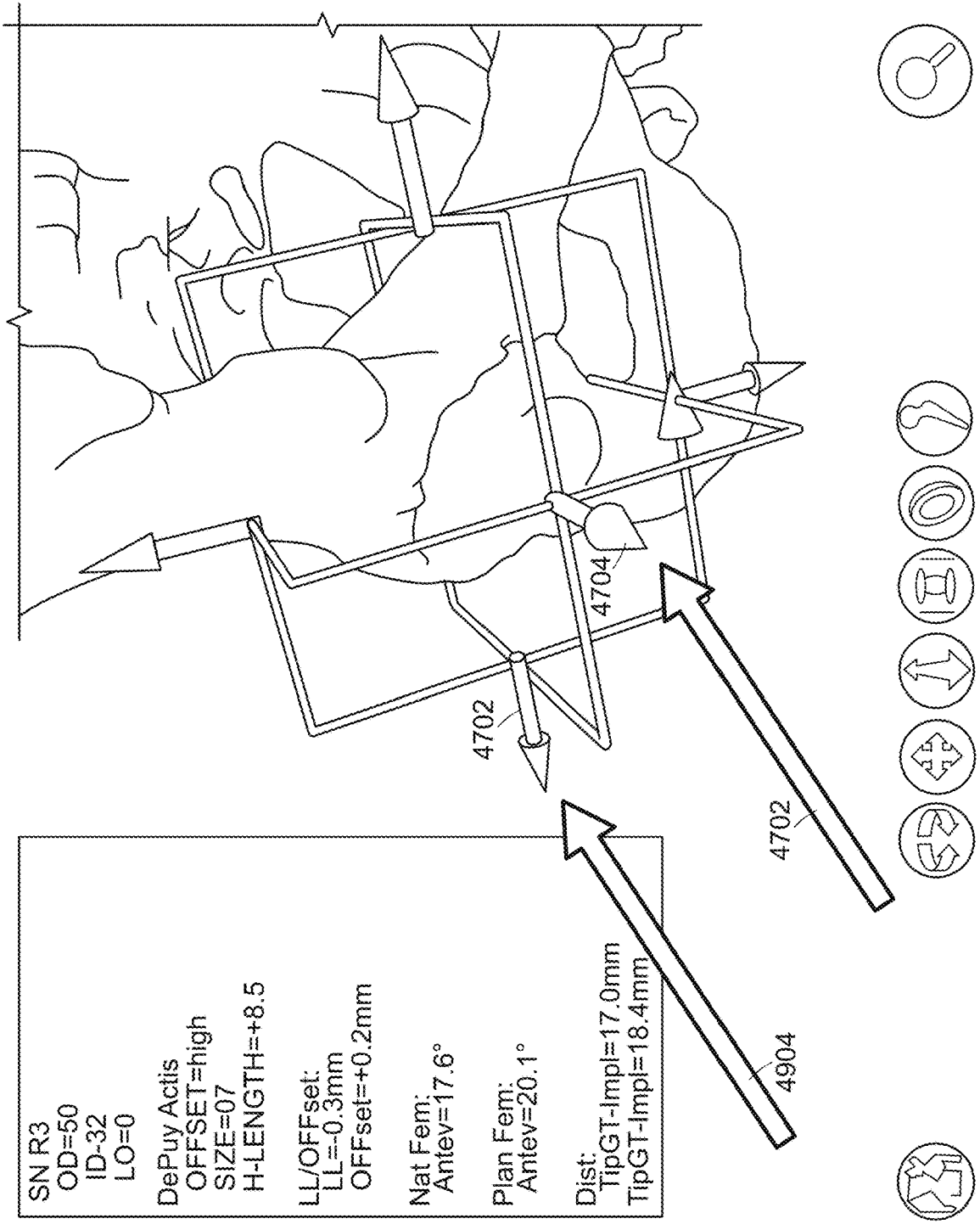
FIG. 49 is an illustration of a surface model of a pelvis illustrating viewpoints of a surgeon in accordance with one or more embodiments.

FIG. 49 shows the original surgeon's viewpoint (the red arrow 4704 designated by the purple arrow 4702) and a potential second viewpoint that is the red arrow 4902 designated by the light blue arrow 4904.

Figure 50:
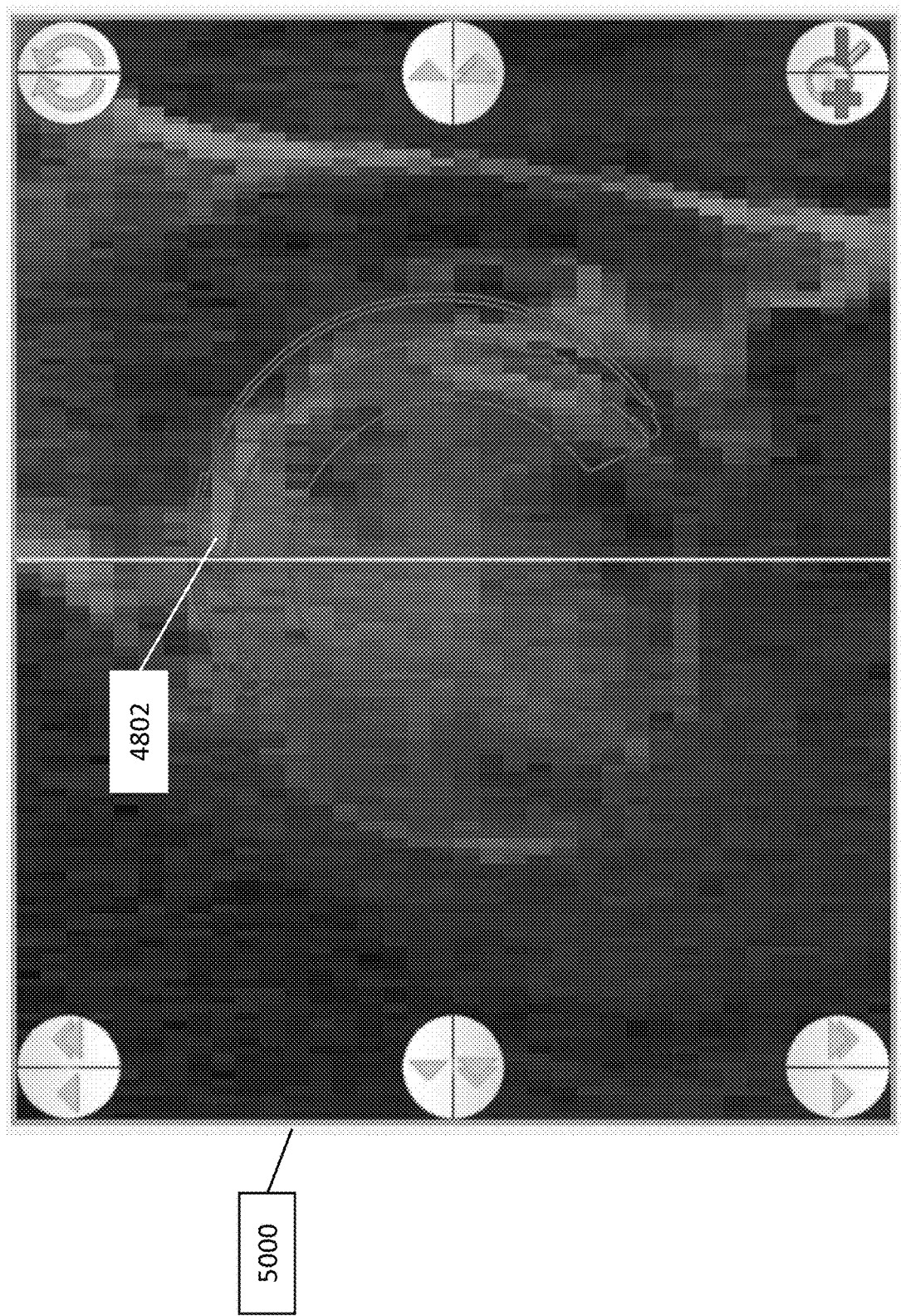
FIG. 50 is a pictorial representation of an image generated and projected by an AR device in accordance with one or more embodiments.

FIG. 50 is a pictorial representation of an image 5000 generated by the AR device 200 of a cut plane in the plane of the green box 4604, being perpendicular to the surgeon's line of sight when viewing from the point of view of the red arrow 4902 that is designated by the light blue arrow 4904. The AR device 200 may display the image 5000 in the exact location from which the image pixels were acquired from inside the patient's body at the time that the CT study (or any other image study with such a dataset) was acquired.

As described, the AR device 200 may automatically display images that are perpendicular to the surgeon's viewpoint in real time as the surgeon moves his or her head around. The AR device 200 also may "hold" the display of an image in the green box 4604, e.g., in response to user input, and the surgeon wearing the AR headset 200 may be able to move the AR headset 200 around without causing a new image to be recalculated.

The AR device 200 may thus create and present images that are co-located with the actual patient, from any desired angle, depth, and shape. In addition, the image need not even be a planar image.

Figure 51:
FIG. 51 is a pictorial representation of an image generated and projected by an AR device in accordance with one or more embodiments.

FIG. 51 is a pictorial representation of an image 5100 generated by the AR device 200 of a cut plane in the plane of the red box 4606.

In some embodiments, multiple planar cuts may be made through the CT volume data and presented by the AR device 200. For example, three orthogonal, planar cuts can be made in the CT volume data and presented by the AR device 200.

It also should be understood that the cuts made through the CT volume data need not be planar. For example, a curved cut or other shaped cut may be made through the CT volume data and presented by the AR device.

In addition, the presentation of portions of CT volume data may be utilized in other procedures besides orthopedic surgery of the hip, knee, and other joints. For example, a CT scan may be conducted of a tumor. During a percutaneous biopsy of the tumor, images based on one or more cut planes through the CT volume data may be generated and presented to assist the surgeon in performing the biopsy.

Multiple AR Devices

In some embodiments, more than one person in the operating room 100 may be wearing an AR device 200. For example, one or more assistants in addition to the surgeon 114 may be wearing AR devices 200. The AR device 200 worn by the surgeon may be primary AR device, which may operate as a server, and the other AR devices may operate as clients of the primary AR device.

Figure 52:
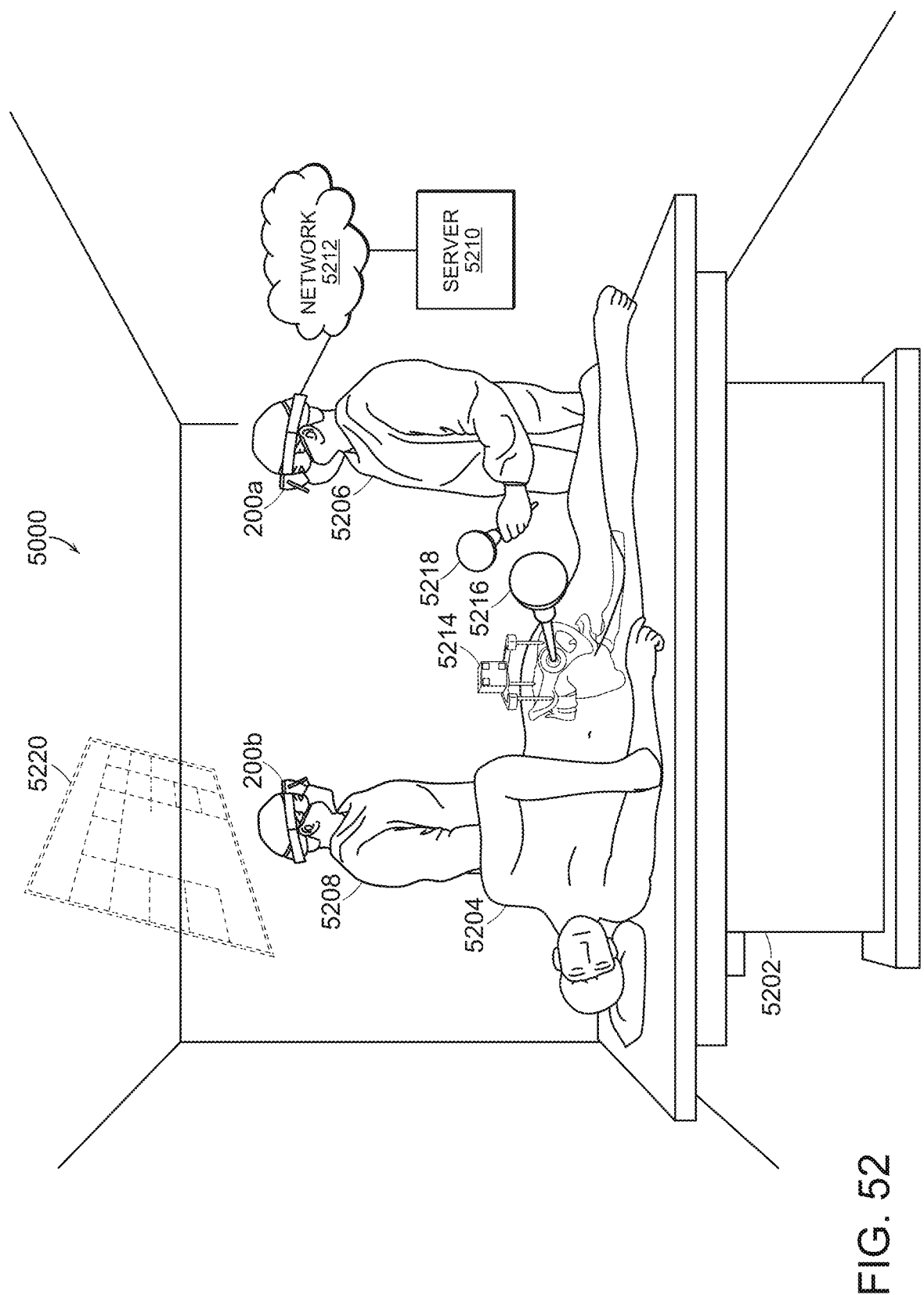
FIG. 52 is a schematic illustration of an operating room in accordance with one or more embodiments.

FIG. 52 is a schematic illustration of an operating room 5200 in accordance with one or more embodiments. Disposed in the operating room 5200 is an operating table 5202 on which a patient 5204 is positioned for a surgical procedure. A surgeon 5206 and at least one other medical professional 5208 may be in the operating room 5200. The surgeon 5206 and the medical professional 5208 may each be wearing an AR device 200a and 200b respectively. One or more of the AR devices, such as the AR device 200a, may be connected to a server 5210 via a network 5212. A physical registration and tracking device 5214 may be docked to the patient's pelvis. The AR devices 200a and 200b may present one or more virtual images, e.g., holograms, during the surgical procedure on the patient 5240. For example, a hologram 5216 of a cup impactor may be presented in a planned location relative the patient's pelvis. For example, the AR device 200a may detect the physical registration and tracking device 5214 and present the hologram 5216 of the cup impactor. The surgeon 5206 may guide a physical cup impactor 5218 to be aligned with the hologram 5216 to achieve one or more goals of the surgical procedure, such as implanting a prosthetic cup component at a planned location in the patient's pelvis. In some embodiments, one or more of the AR devices 200a and 200b may present a User Interface (UI), as indicated at 5220, in the operating room 5200, such as in space or against one or more walls of the operating room. The UI may be of a planning application presenting a surgical plan for the surgical procedure on the patient.

Automated Object Recognition and Registration of Tools and Body Structures.

The navigation system 1600 may receive data captured by one or more of the camera(s) on the AR device 200 of the surgical scene, such as image data in some embodiments. The object recognizer 1602 may detect an object in the received image data, and the object tracker 1606 may track the detected object. For example, the AR device 200 may transmit captured image data, e.g., via the network device 112, to the data processing device 100. The model database 1608 may be configured with data regarding the shape of the patient-specific HipXpert tool, such as three-dimensional (3D) shape for the HipXpert tool. As noted, the data may be one or more CAD files, 3D model data, etc. The object recognizer 1602 may search for an object in the received image data that matches this data, thereby identifying the HipXpert tool for example in the image data. The information in the model database 1608 may include the dimensions of the HipXpert tool on a patient specific basis, e.g., as adjusted for a specific patient, and may also know the location of the pelvis relative to the HipXpert tool, for example as determined during the surgical planning phase. The object recognizer 1602 may detect and/or recognize the HipXpert tool in a field of view, e.g., the image data, and the object pose detector 1604 may determine its orientation from which the navigation system 1600 may then calculate and track the location of the patient's pelvis in space. The object recognizer 1602 may implement the Vuforia Engine and Vuforia Model Targets technology from PTC Inc. of Boston, Mass.

The surgeon may affix a second object, e.g., a tracker attached to the patient's pelvis, that can then be tracked, and a calculation of the second object's location relative to the HipXpert tool can be made by the navigation system 1600. The location of the pelvis can then be determined relative to this second object, allowing the HipXpert tool to be removed. That is, the navigation system 1600 may recognize the HipXpert tool itself optically because its size and shape are known to the system 1600, and so "seeing" it from any angle would allow for the determination of exactly where the HipXpert tool is positioned and oriented in space. The dimensions of the HipXpert tool and the predicted docking of the HipXpert tool onto the patient's pelvis is patient-specific, so the system 1600 may need to be configured with those parameters on a patient-specific basis.

Other tools also can be tracked in space either by teaching the system the unique CAD geometry of the other tools or affixing an object that is more easily tracked to the tool to be tracked. This may be useful for a cup impactor or acetabular reamer. The same may be true for the femur or any instrument used on the femur. The femur may be registered by recognizing a unique small visible section of the surface with a tracker attached to it, as described. The navigation system 1660 may track the femur based on object recognition and tracking of the object. In some embodiments, a tracker may then be attached to the femur and tracking continued based on this tracker allowing the surgeon to change the femur surgically making it no longer recognizable while still allowing the femur to be tracked. The process may be called patient-specific shape recognition registration methodology.

As described, tracking may be performed using the spatial detection system provided by the AR device 200, such as the depth camera 230 and the IR emitters. For example, the navigation system 1600 may implement simultaneous localization and mapping (SLAM) utilizing the data generated by the depth camera 230. In other embodiments, tracking may be performed by two cameras of known relative orientation to allow for stereoscopic calculation. Further, the stereoscopic cameras could be affixed to the AR device 200 as described, while in other embodiments image data from the 3D detection system 108 may be used by the navigation system 1600 either alone or in combination with image data from the AR device 200. The advantage of acquiring the image information from the one or more cameras on the AR device 200 is that the surgeon always needs a primary line of site, giving the camera(s) of the AR device 200 the same line of site as the surgeon. This is in contrast to the situation with traditional infrared stereoscopic cameras where line-of-site competition between the surgeon and the camera can occur. The other advantage of having the camera(s) on the surgeon's head is that the viewpoint of the camera(s) relative to the surgeon's eyes is known so that an augmented reality display of virtual objects can be displayed in the same perspective that the real objects would be seen in (except that they would otherwise be invisible, being buried deep inside the body) except perhaps for small exposed subsections during surgery.

In other embodiments, other tools besides by the HipXpert tool may be used and recognized and tracked by the navigation system 1600.

To aid in detecting a patient-specific object and determining its orientation and/or pose, the object may be asymmetrical and/or uniquely recognizable within the surgical scene. For example, to the extent the object is a tool, the tool may be asymmetrical. To the extent the object is a body part, the body part may be asymmetrical. Nonetheless, symmetrical objects, such as body parts, and/or tools may be used in the present disclosure.

In some embodiments, the compass portion of the HipXpert device may be omitted or removed.

In some embodiments, a second object may be attached to the object, e.g., body part, or to the tool to aid in detecting the object or tool in the image data and/or in determining its orientation and pose. The second object may be attached to the object or the tool in known geometric relationships such that locating the second object and determining its orientation and/or pose can be used to determine the location and/or orientation of the object and/or tool, e.g., using one or more translations.

In further embodiments, one or more markings may be applied to the object and/or tool to aid in its detection and/or in determining its orientation and/or pose. For example, a checkerboard or other unique and/or recognizable pattern may be applied to the object.

During the planning stage, adjustments may be determined for the physical registration and tracking tool 2100 so that it will fit, e.g., be docked to the patient's pelvis, as planned. The adjustments may include how far to slide out the extendable arms 2104a and 2104b so that the tips of the legs contact the patient's pelvis at planned locations. Thus, the dimensions of the tool 2100 may vary from one patient to another. Nonetheless, the dimensions of the hub 2102 of the tool 2100 is identical for all patients, e.g., it is a static component of the tool 2100. Furthermore, as described, the cube 2108 may be attached to the hub 2102 of the tool 2100 in the same manner for all patients.

In some embodiments, the cube 2108 with the QR code(s) may be omitted from the tool 2100. With this embodiment, the AR device 200 may be configured to recognize the physical tool 2100 in the operating room. For example, the AR device 200 may recognize one or more portions of the physical tool 2100 that is the same for all patients, such as the hub 2102. In this way, the same recognition process may be used for all patients even though the tool 2100 also includes portions adjusted on a patient-specific basis, e.g., the extent to which the arms 2104a and 2104b are extended. A patient-specific transformation matrix may be determined relative to the static portion of the tool being recognized, e.g., the hub 2102. Providing a portion of a registration and tracking tool that is static, e.g., the same, for all patients, and configuring the AR device 200 to recognize this portion of the tool may be more efficient, e.g., in terms of planning, processing and memory resources, than individually configuring the AR device 200 for each patient to recognize the tool as a whole as adjusted for each patient.

Figure 45:
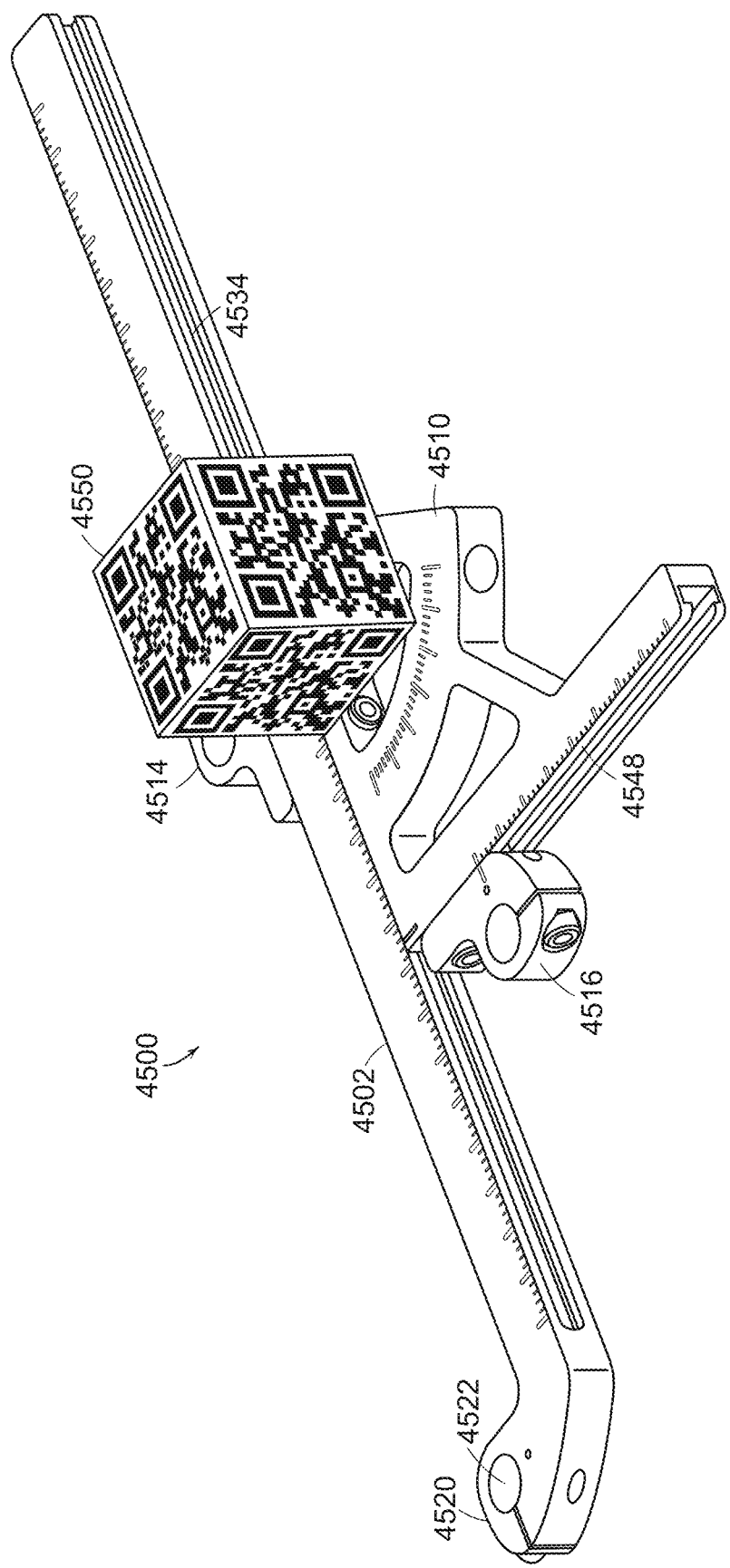
FIG. 45 is a perspective view of a portion of a registration and tracking tool in accordance with one or more embodiments.

FIG. 45 is a perspective view of a hip registration and tracking tool 4500. The tool 4500 may include an elongated support arm 4502, a support frame 4510, a first moveable leg brace 4514, and a second moveable leg brace 4516. The elongated support arm 4502 may include a first end 4520. Disposed at the first end 4520 may be an opening 4522 configured to receive an end of a first leg (not shown) that may extend perpendicularly from the support arm 4502. An end of a second leg may be received at the first moveable leg brace 4514, and an end of a third leg may be received at the second moveable leg brace 4516. The second and third legs may also extend perpendicularly from the elongated support arm 4502, like the first leg.

A first track 4534 may be formed along at least a portion of a front side of the support arm 4502, and a second track (not shown) may be formed along at least a portion of a back side of the support arm 4502. The first and second tracks may be recessed tracks, such as slots or grooves. The support frame 4510 may include a first edge that engages the first track 4534 securing the support frame 4510 to the elongated support arm 4502, while allowing the support frame 4510 to slide along the front side of the elongated support arm 4502. The first moveable leg brace 4514, and thus the second leg, may be configured for slidable attachment to the back side of the elongated support arm 4502. The support frame 4510 may include a second edge 4548 to which the second moveable leg brace 4516 may slidably attach.

The first leg may have a tip configured to contact the right ASIS. Second and third legs may be slidably attached to the elongated support arm relative to the first leg. The distances between the first leg and the second and third legs may be determined preoperatively so that, when the second and third legs, are set to these predetermined distances along the elongated support arm, a tip of the second leg contacts the left ASIS, and a tip of the third leg contacts an anterior aspect of the ischium of the patient's pelvis below the acetabulum of the hip being operated on. An operating surgeon may access the patient's hip joint using the anterior approach or the anterolateral approach (e.g., with the patient in the supine position), and may dock the apparatus to the patient, thereby registering the patient's pelvis and establishing the patient-specific, supine pelvic reference plane and/or coordinate system.

Mounted to the support frame 4510 may be a cube 4550 with one or more QR codes. During surgery, the first moveable leg brace 4514 and the second moveable leg brace 4516 of the physical tool 4500 may be adjusted as planned so that the tips of the respective legs contact the patient's pelvis at the planned locations. The tool 4500 may be docked to the patient's pelvis. The AR device 200 may detect the one or more QR codes on the cube 4550 and may anchor one or more holograms as described herein.

The tool 4500 may be flipped over so that it may be used to operate on a patient's left or right hips. The support frame 4510 and the cube 4550 may also be flipped around so that it remains on top of the tool 4500.

Thus, the only things that may be specific for a patient when using a HipXpert registration and tracking tool or the tool 4500 are the arm lengths or the positions of the moveable leg braces, respectively, and the single patient-specific matrix, which may relate where the respective tool is in space to the raw image coordinate system from the CT scanner with the patient randomly placed within it.

In some embodiments, instead of utilizing a single tool that operates as a combination registration and tracking device, separate registration and tracking tools may be utilized. For example, a cube with one or more QR codes may be randomly attached to a patient's pelvis. A surgeon may then register the patient's pelvis, e.g., utilize a digitizing probe to digitize a plurality of points on the patient's pelvis. The location of the cube with the one or more QR codes may then be determined relative to the patient's pelvis as registered. The AR device 200 may then present one or more holograms in the planned locations and as anchored relative to the cube with the one or more QR codes.

It should be understood that other elements besides or in addition to a QR code may be used to register the pelvis or another anatomical structure, such as a tracker.

Figure 57:
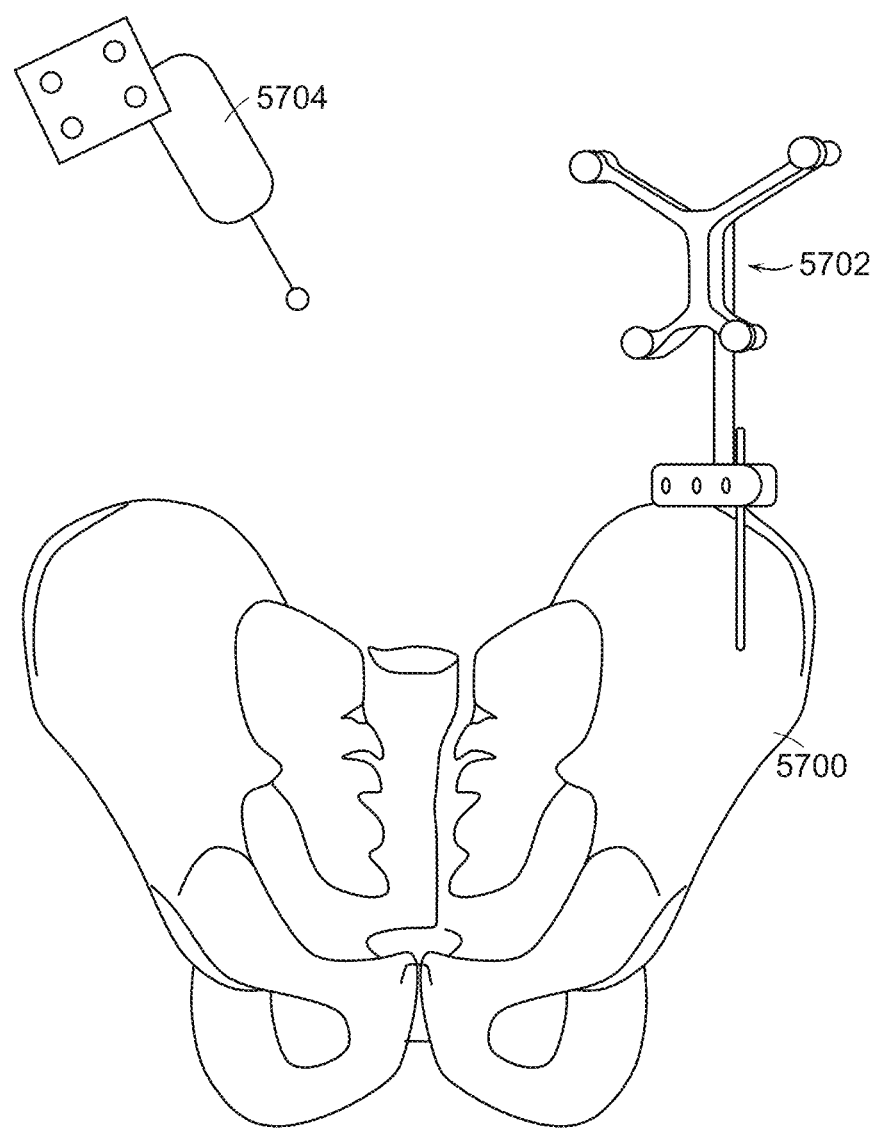
FIG. 57 is a schematic illustration of a front view of a pelvis in accordance with one or more embodiments.

FIG. 57 is a schematic illustration of a front view of a pelvis 5700 in accordance with one or more embodiments. During the surgical procedure, a surgeon may attach a tracker 5702 to the pelvis 5700 at a random location. In some embodiments, the AR device 200 may recognize the tracker 5702 by virtue of its shape using object recognition and/or the AR device 200 may recognize an image on the tracker 5702, such as by way of example only a QR code. Alternatively, the tracker 5702 may include optical or magnetic elements that can be detected by the tracking system 106. The surgeon may utilize a digitizing probe 5704 to digitize a plurality of points on the surface of the pelvis 5700. The AR device 200 may similarly recognize the tracker using object and/or image recognition. Alternatively, the digitizing probe 5704 may include optical or magnetic elements that can be detected by the tracking system 106. The navigation system 1600 may process the digitized points to register the pelvis 5700. The navigation system 1600 may also track the pelvis 5700 via the tracker 5702 as detected by the AR device 200 or the tracking system 106. The AR device 200 may present one or more holograms anchored to the pelvis 5700 relative to the tracker 5702.

It should be understood that a similar process may be used with other anatomical structures, such as the knee.

Augmented Reality for Hip Replacement Surgery:

Having the navigation system 1600 know where the pelvis is and having the navigation system 1600 know where the display is located in front of the surgeon's eyes allows for the detailed display of virtual images including computer models, e.g., of the pelvis and one or more tracked tools, from the same perspective as the surgeon. This would allow the surgeon to see the patient in reality, and also to see virtual objects such as the computer model of the pelvis projected onto the lenses of the AR device 200 in the same location as the actual object inside the patient.

Figure 4:
FIG. 4 is a pictorial representation of a surgical procedure showing a registration and tracking device docked on a patient in accordance with one or more embodiments.

FIG. 4 is a pictorial representation of a surgical procedure showing a registration tool, e.g., the HipXpert tool, docked on a particular patient in accordance with one or more embodiments.

The location of the pelvis relative to the HipXpert tool may be known pre-operatively, e.g., during a planning phase. Using the spatial detection systems built into the AR device 200, the navigation system 1600 can calculate the perspective of the 3D object, e.g., the HipXpert tool, another tool, the patient's pelvis, another portion of the patient's anatomy, etc., from the surgeon's viewing perspective at that moment.

Figure 5:
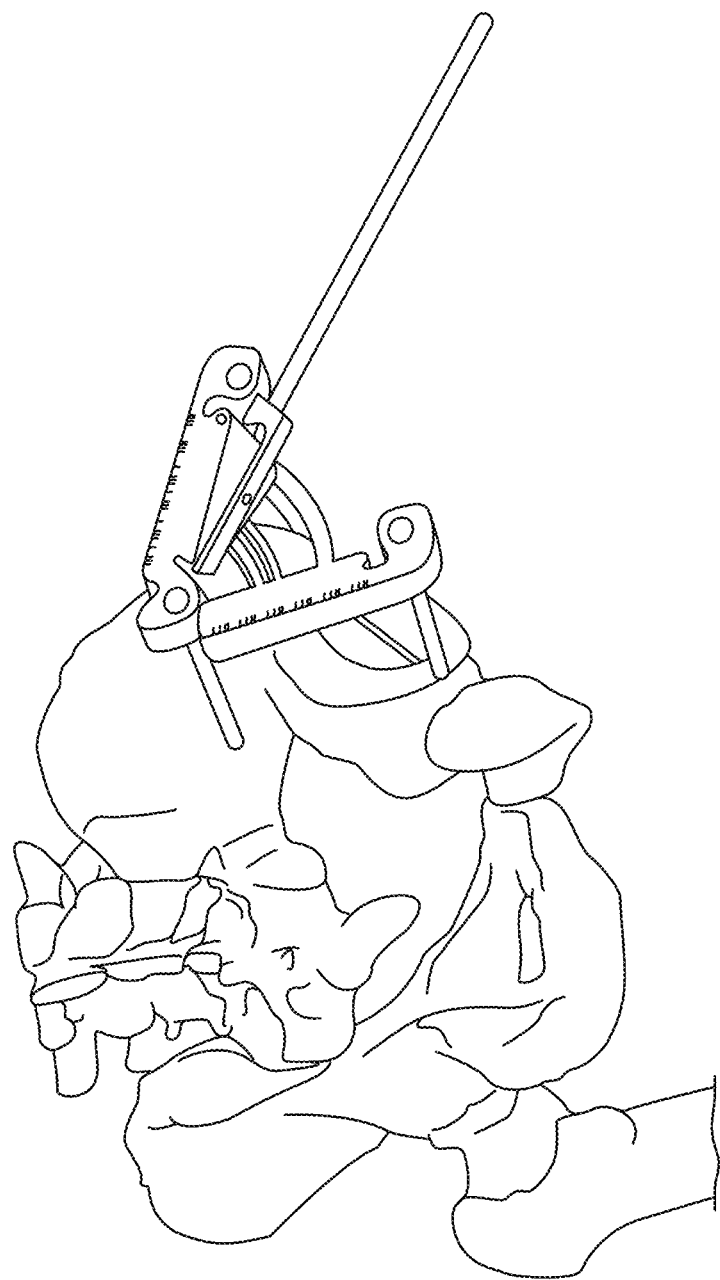
FIG. 5 is an illustration of a 3D surface model of a pelvis with a model of the registration and tracking device docked thereto in accordance with one or more embodiments.

FIG. 5 is an illustration of a 3D surface model of a pelvis with a model of the registration and tracking device docked thereto in accordance with one or more embodiments.

Figure 6:
FIG. 6 is a schematic illustration of an image projected by an AR device showing a virtual image of the patient's pelvis underneath the skin from the exact same perspective as the surgeon at that moment in accordance with one or more embodiments.

Having calculated the surgeon's perspective of the tool and the pelvis, a virtual model of the pelvis can then be projected onto the lenses of the AR device 200 and thus within the surgeon's point of view in real time FIG. 6 is a schematic illustration of an image projected by the AR device 200 showing a virtual image of the patient's pelvis underneath the skin from the exact perspective of the surgeon at that moment in accordance with one or more embodiments.

Similarly, tools that are used on the patient could be seen in reality and a superimposed virtual model of the same tool in the same location could be projected by the AR device 200 for viewing by the surgeon. This would allow the surgeon to see the exact location of a part of the tool which, in reality, has disappeared inside of an incision, but yet a virtual image of which can be "seen" through the AR device 200.

Additionally, work that the tool accomplishes when being used can be tracked by the navigation system 1600 and the object that is changed can be updated. This would be true for example if a virtual display of the pelvis is projected as is a virtual display of an acetabular reamer. The camera(s) is able to track the relative locations of the two objects, and may also track and integrate an effect that the reamer has on the acetabulum, allowing for updating of the pelvis model to reflect the acetabular reaming itself and that could be compared both to the original structure and the planned structure of the acetabulum that the surgeon aims to achieve prior to implantation of the acetabular cup component. Accordingly, the navigation system 1600 may show the surgeon where s/he started, where s/he are so far, and where s/he needs to go next to accomplish to final goal of acetabular reaming.

Automated Object Recognition and Registration of Tools and Body Structures: Example: A Small Field of View Inside the Acetabulum An alternative method of calculating the location of the pelvis in real time during total hip replacement surgery, for example is to get a small view of the actual pelvis through the incision. Assuming the shape of the bone surface within that field of view is sufficiently unique, then the pelvis could be registered automatically by the navigation system 1600 just by "seeing" a small part of this patient-specific, unique object. For example, during total hip replacement, the femoral head is removed and the inside of the acetabulum is exposed. As long as the spatial detection system can see this bony structure, an automated shape registration of the entire bone could be accomplished.

Figure 7:
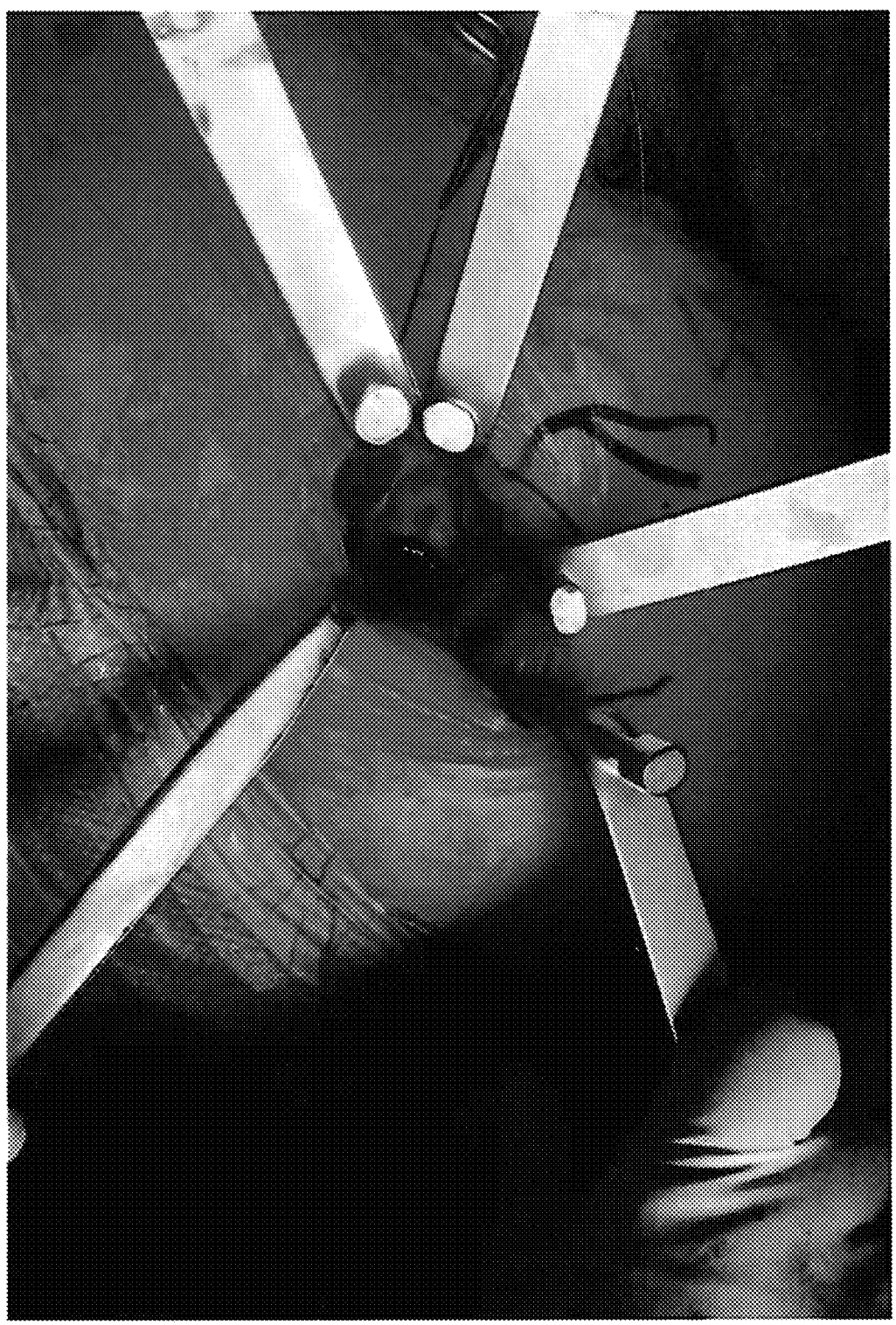
FIG. 7 is a pictorial representation of the view into the acetabulum of a patient through an incision during surgery in accordance with one or more embodiments.

FIG. 7 is a pictorial representation of the view into the acetabulum of a patient through an incision during surgery in accordance with one or more embodiments.

Figure 8:
FIG. 8 is an illustration of a 3D surface model of the patient's pelvis from the same perspective as FIG. 7 in accordance with one or more embodiments.

FIG. 8 is an illustration of a 3D surface model of the patient's pelvis from the same perspective as FIG. 7 in accordance with one or more embodiments. This matching registration can be done by the navigation system 1600, for example, by matching unique actual and virtual shapes together using object recognition.

Figure 9:
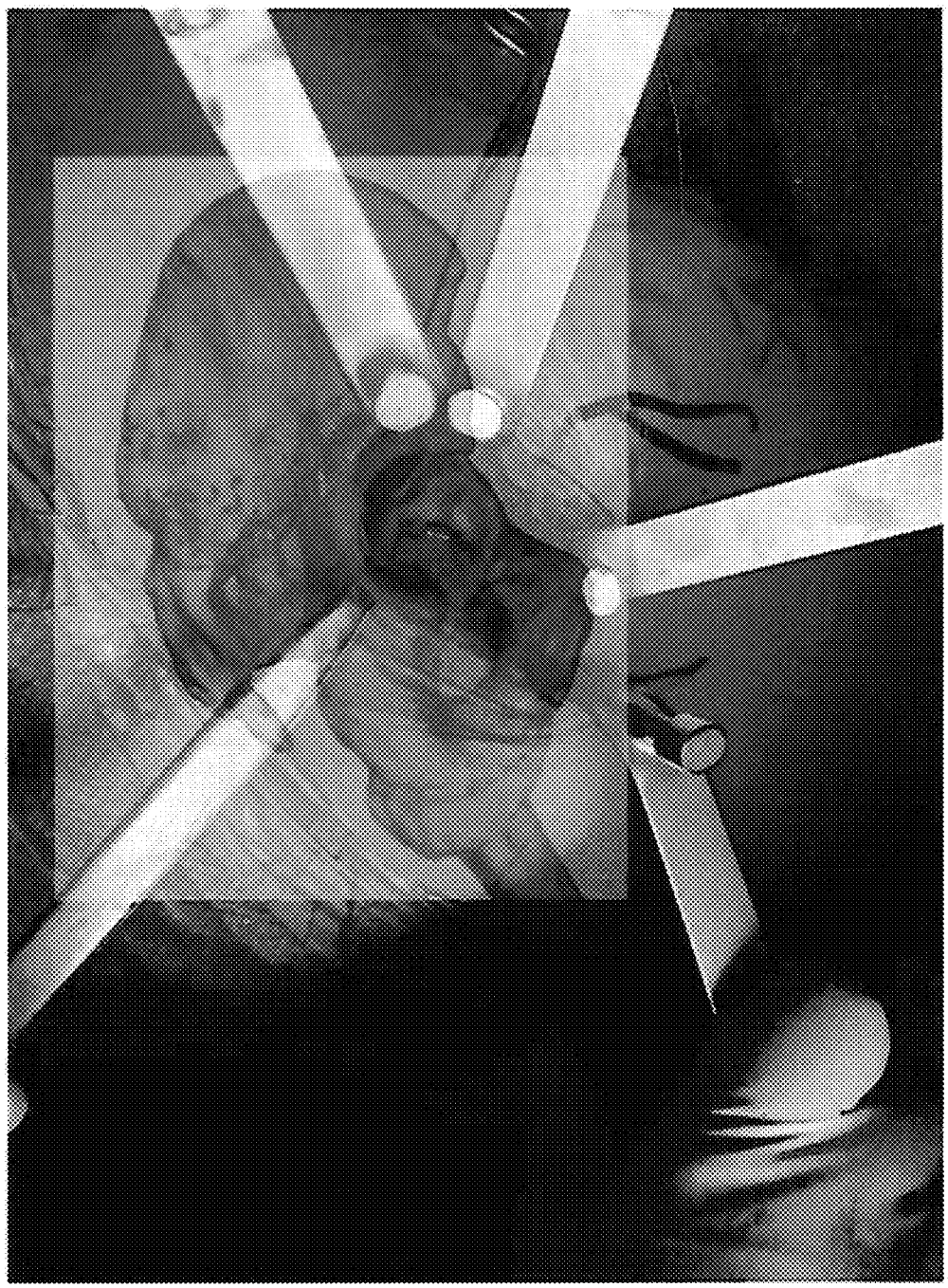
FIG. 9 is a schematic illustration of an image projected by an AR device showing a virtual image of the patient's pelvis underneath the skin from the exact same perspective as the surgeon at that moment in accordance with one or more embodiments.

FIG. 9 is a schematic illustration of an image projected on the AR device 200 showing a virtual image of the patient's pelvis underneath the skin from the same perspective of the surgeon at that moment in accordance with one or more embodiments.

With existing systems, if instruments block the view or the bone surface is changed, then accurate registration and tracking is lost. In accordance with one or more embodiments of the present disclosure, this disadvantage can be avoided by attaching a separate tracker to the bone and transferring the relative information achieved through recognition of the patient-specific object and then simultaneous identification of the location of the separate tracker to the pelvis. Then, so long as the separate tracker can be tracked, surgery can proceed even though the surface that was used to achieve initial registration has been modified.

The system could combine the registration techniques depicted in FIGS. 4-6 and FIGS. 7-9 to achieve even greater accuracy.

Reality Feedback and Update Loop

In some embodiments, one or more anatomical structures may not be prepared in precisely the manner as planned. Nonetheless, a surgeon may determine that the partial preparation is acceptable, for example to achieve the one or more goals of the surgical procedure. For example, suppose a patient's acetabulum is prepared and a cup component implanted. However, suppose further that the cup component is not implanted exactly as planned, e.g., the position and/or orientation of the cup component within the acetabulum is somewhat different than the planned position and/or orientation. In some embodiments, the cameras or other sensors of the AR device 200 may be trained on the cup component as implanted. The object recognizer 1602 may detect and recognize the cup component. The navigation system 1600 may determine the position and/or orientation of the cup component as implanted and provide this information to the surgical planning system 1700. The surgical planning system 1700 may update the surgical plan for the patient using the actual position and/or orientation of the cup component as implanted, rather than the planned position and/or orientation. In other embodiments, the navigation system 1600 may determine the actual position and/or orientation of the cup component as implanted by determining a final location of the cup impactor. For example, the object recognizer 1602 may recognize the cup impactor while in its final location. The navigation system 1600 may determine the actual position and/or orientation of the cup component based on the final location of the cup impactor and the known geometry of the acetabular liner that is then inserted into the cup. For example, the navigation system 1600 may be configured with the geometric relationship between the cup impactor and the cup component. Thus, the navigation system 1600 can derive the position and/or orientation of the cup component from the position and/or orientation of the cup impactor. Alternatively or additionally, one or more trackers may be attached to the cup impactor, and the navigation system 1600 may determine the position and/or orientation of the cup impactor from the one or more trackers.

It should be understood that this is but one example of a reality feedback and update mode of the present disclosure. Feedback and updating the surgical plan may be performed with other elements besides the cup component and in other surgical procedures, such as knee repair.

In some embodiments, a sequence of holograms may be as follows:

1. pelvis and HipXpert device custom adjusted for the patient and docked to patient's pelvis, with the pelvis unchanged;

2. pelvis and HipXpert device custom adjusted for the patient and docked to patient's pelvis with the ideal cup bed as planned at the acetabulum;

3. HipXpert device custom adjusted for the patient (without pelvis), with ideal cup bed;

4-7. pelvis and HipXpert device custom adjusted for the patient and docked to the patient's pelvis and with a sequence of reamers and reamer handles in proposed locations. For example, if the planner wants to put in a 56 mm acetabular cup component, the planner might plan for the use of a 51 mm, a 53 mm, a 55 mm, and finally a 56 mm reamer. Each one of these reamers will do a certain amount of the work to achieve the final cup bed at the acetabulum. Holograms could be generated for each reamer and, during surgery, the holograms could be presented and the surgeon could work each reamer to match up with the hologram;

8. pelvis and HipXpert device custom adjusted for the patient and docked to the patient's pelvis, the cup component and the cup impactor with the screw holes of the cup component lined up in the planned orientation as the cup can be rotated around the handle. Alternatively or in addition, a hologram of the cup component and the cup impactor floating in space so that the surgeon can line up the screw holes perfectly rotationally;

9. pelvis and HipXpert device custom adjusted for the patient and docked to the patient's pelvis and the cup component and the cup impactor with the cup component located at the final location. Then, during surgery, with the physical cup impactor that matches the hologram, the surgeon would know that the cup component is in the planned, final location when the physical cup impactor and the physical cup component attached thereto line up perfectly with the hologram;

10. pelvis and HipXpert device custom adjusted for the patient and docked to the patient's pelvis and the cup component and the proposed screws for the cup component with planned directions and lengths to indicate to the surgeon the planned, e.g., optimal, direction to drill in and how long the screws will be;

11a and b. pelvis and HipXpert device custom adjusted for the patient and docked to the patient's pelvis and cup component showing with (a) and without (b) surrounding osteophytes to show the surgeon what to trim. Having planned removal of osteophytes, the systems and methods can determine what the potential impingement and/or free range of motion would be from the surgery and could show this information, for example based on degree of osteophyte removal; and 12. pelvis and HipXpert device custom adjusted for the patient and docked to the patient's pelvis and the cup component and the liner, e.g., the final product;

In some embodiments, the systems and methods may then do object recognition of the cup component and the pelvis to determine what the actual result of implantation is. Based on this information, the systems and methods could recalculate impingement and/or range of motion, i.e., on the spot, as desired.

Example of Clinical Implementation for Total Knee Arthroplasty.

Three technologies exist for Total Knee Arthroplasty (TKR). They include:

1. image-based registration and navigation (with or without robotics) and/or statistical shape modeling, e.g., based on a large data set and patient-specific characteristics;
2. image-free registration and navigation (with or without robotics); and
3. physical template registration.

Image-based navigation of TKR was one of the first methods employed where 3D models and coordinate systems are developed in advance, and then the bones are registered in surgery by digitizing surface points that allow for matching registration. This method fell out of favor until a more recent resurgence with robotics.

Alternatively, image-free methods allow for knee navigation by (with a tracker affixed) moving the hip around to triangulate its position, directly digitizing ankle points, and then putting in the requisite information on the distal femur and proximal tibia with a digitizer.

A third method (which is image-based) makes a physical template that locks into the anatomy in a predictable way. The physical template may contain cutting slots to allow for bone surface resection as planned. Alternatively, the template may be used to transfer the information to one or more other tools, for example by having drill holes for the drilling of holes within the bone for the placement of pins. The template may then be removed and another surgical tool that fits over the same pins in a predictable way may be affixed and used. Used this way, these physical templates do not allow for the traditional navigational calculations such as alignment, ligament balance and range of motion but they do allow for accomplishing the goals of the surgery in a more basic way.

Again, alternatively, the physical templates may be used as a registration and tracking device for subsequent navigation. An exemplary physical template is the acetabular template disclosed in U.S. Pat. No. 8,986,309 for an Acetabular Template Component and Method of Using Same During Hip Arthroplasty, which is hereby incorporated by reference in its entirety.

Figure 44:
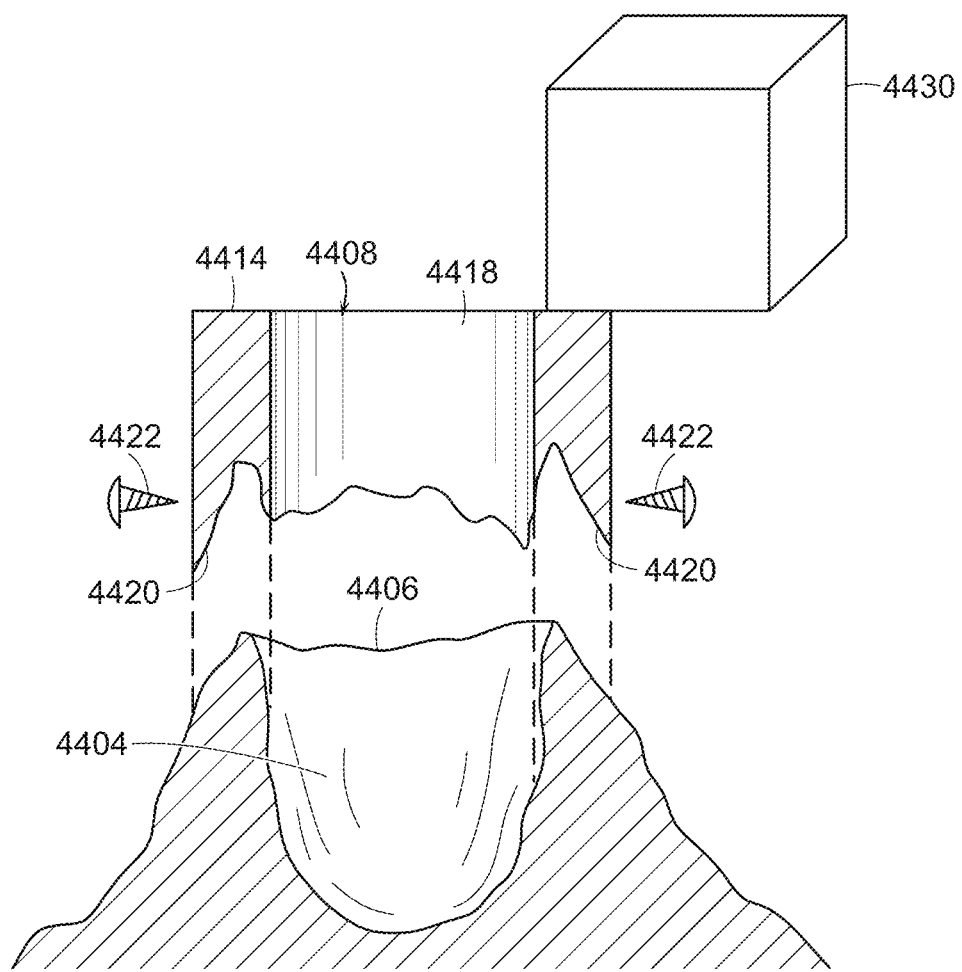
FIG. 44 is a partial side view of a patient's acetabulum with a custom fitted template in accordance with one or more embodiments.

FIG. 44 is a partial side view of a patient's pelvis 4402 showing the patient's acetabulum 4404 and acetabulum rim 4406 with a custom fitted template 4408 in accordance with one or more embodiments. The custom fitted template 4408 may be generally circular shaped to mate with all or a substantial portion of the patient's acetabular rim 4406. Because the template 4408 matches the rough and uneven shape of the acetabular rim 4406, it fits to the rim 4406 and thus the pelvis in a single orientation. The template 4408 may have an upper surface 4414 and a lower surface 4420 opposite the upper surface 4414. Mounted on the upper surface 4414 may be a cube 4430 having QR codes (not shown) on at least some of its surfaces or faces. The lower surface 4420 is shaped to match the acetabular rim 4406. The template 4408 may have an open interior 4418 so that the template 4408 does not interfere with the placement of an acetabular cup component within the patient's acetabulum 4404.

The template 4408 may be held in place by one or more fasteners, such as screws 4422. With the template 4408 fitted to the patient's acetabulum, the AR device 200 may detect one or more of the QR codes on the cube 4430 and register the patient's pelvis. One or more patient-specific transformation matrices may be associated with the cube 4430 and/or QR codes and used to determine the orientation and position of virtual images, e.g., holograms, relative to a QR code and/or the cube 4430.

Automated Object Recognition and Registration of Tools and Body Structures: Example: The Distal Femur for TKR The present disclosure may use the spatial detection system of an augmented reality HMD for example to register and track anatomical structures and/or tools, for example by recognizing the three dimensional orientation of a portion of exposed anatomy, e.g., as viewed through an incision. For example, the knee may be opened and the spatial detection system or the camera(s) in the AR device 200 may see the end of the femur. The navigation system 1600 may then track the orientation of the entire femur by having the one or more of the sensors or cameras of the AR device 200 see a portion of the patient-specific anatomical object. In some embodiments, this may be referred to as an object-based, image-based methodology in which a particular object is identified pre-operatively and the navigation system 1600 searches the image data for that particular patient-specific object in the operative scene. As noted, for hip surgery, the HipXpert tool is tuned, e.g., adjusted, to the particular patient, and the navigation system 1600 is prepared to recognize that the HipXpert tool as adjusted for the patient within the image data of the surgical scene. Based on the detection of the patient specific object within the surgical scene, the navigation system 1600 may then register the rest of the "internal" scene, e.g., the patient's pelvis, another anatomical component or feature, etc.

For total knee replacement (TKR), CT, MR, statistical shape or other predictive modeling, or other data may be obtained of the patient's femur, tibia, hip, and ankle pre-operatively. The acquired data may be used to generate 3D models, which may be in the form of CAD files, of patient's femur, tibia, hip, and ankle, including the portions of the femur and tibia that are to be exposed during TKR surgery. These models may be stored in the model database 1608 of the navigation system 1600 and utilized during the object recognition and object orientation/pose determination steps.

In some embodiments, the AR device 200 may perform object recognition of the top end of the tibia. Suppose, the top surface of the tibia is amorphous such that the AR device 200 locks on the location of the tibia just with object recognition of the top of the tibia leading to insufficient registration. The object recognition may be sufficient for height of the tibial articular surface for example, but not for accuracy of the longitudinal axis. The AR device 200 may present a hologram of the whole tibia and a QR cube on the tibia with a phase 1 registration step of less than sufficient registration based on object recognition of the proximal tibia alone. If the AR device 200 presents the tibia—top and bottom, as a hologram, and the tracker keeps the top end closely matched, then the surgeon could move the patient's ankle into position to make it coincident with the hologram. That is, the surgeon may move the reality, e.g., the patient's leg, into alignment with the augmented reality, e.g., the hologram.

Figure 10:
FIG. 10 is a pictorial representation of a patient's knee showing a view of the distal femur during total knee replacement in accordance with one or more embodiments.

In the case of the femur for knee replacement, the surgeon may want to modify the very anatomical part that the navigation system 1600 is tracking, which might otherwise end the tracking. To obviate this, the navigation system 1600 may transfer the information to an object, such as a tracking frame, affixed to the bone that could still be tracked throughout the procedure. Using this technique, the navigation system 1600 can recognize and track the entire femur by seeing a sufficient amount of the distal femur and matching it up in real time to a virtual model of the entire femur. If a tracking frame is then attached, its relationship to the model of the entire femur can then be determined by the navigation system 1600, e.g., through one or more geometric translation operations. In the case of patient-specific anatomical object recognition and registration of the bone that is being described now, the location of the bone is already known at the time that the tracking frame is affixed so there is no subsequent registration step. Once the information it transferred to the second object, the bone can then be modified in the surgery and tracked throughout the procedure even though the original patient-specific anatomical object that was initially used to determine the location of the bone no longer exists in a subsequent stage of the surgery. FIG. 10 is a pictorial representation of a patient's knee showing a view of the distal femur during total knee replacement in accordance with one or more embodiments.

In some embodiments, a physical template having a surface that matches the surface of the distal femur or the proximal tibia may be attached to the femur or tibia. The physical template may include a tracker. The tracking system 106 and/or the AR device 200 may recognize the physical template and/or the tracker and register the femur or tibia. A tracker may be attached to the femur or tibia in a random manner, and the registration of the femur or tibia may be transferred to this tracker. The physical template may then be removed and the procedure continued.

Figure 11:
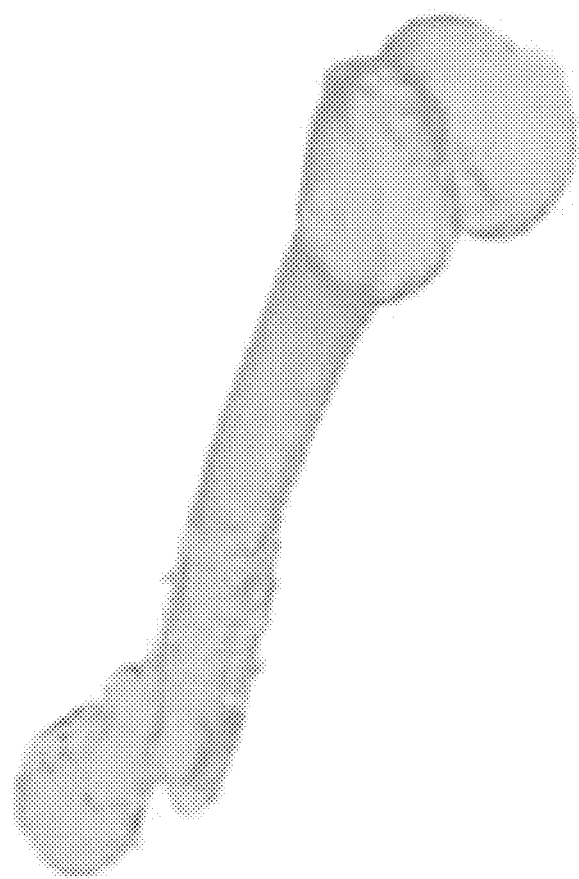
FIG. 11 is an illustration of a 3D surface model of the patient's femur intended to depict the exact same bone in the exact same orientation as the surgeon's view, for example as determined by automated surface matching using stereoscopic cameras or any other method of stereoscopic surface detection in accordance with one or more embodiments.

FIG. 11 is an illustration of a 3D surface model of the patient's femur intended to depict the exact same bone in the exact same orientation as the surgeon's view as determined by automated patient specific anatomical object recognition in accordance with one or more embodiments.

Figure 12:
FIG. 12 is a schematic illustration of an image projected by an AR device showing a virtual model of the femur placed in space in the exact same place as the actual femur as seen from the surgeon's point of view in accordance with one or more embodiments.

FIG. 12 is a schematic illustration of an image projected by the AR device 200 showing a virtual model of the femur placed in space in the exact same place as the actual femur as seen from the surgeon's point of view in accordance with one or more embodiments.

Again, attaching a tracker to the bone would allow the registration information to be transferred to the tracker so that the surfaces that were originally used to achieve registration can be modified. This would allow for continued navigation and augmented reality display continuously from the surgeon's point of view no matter what that view is. In addition to trackers having optical or magnetic elements, such as the tracker 5702 illustrated in FIG. 57, a tracker may be a 2D or 3D shape that is spatially unique and thus recognizable by the AR device 200. Exemplary 3D shapes include an optical tracker without the reflective elements, e.g., just the arm elements. Exemplary 2D shapes include a metal plate having a non-symmetrical star shape or a non-symmetrical cross shape, etc.

As disclosed, in some embodiments, the present disclosure may replace the use of physical templates, such as templates used at the knee and/or acetabulum. Instead, the system effectively presents a virtual template, such as a hologram of a template, that locks onto the patient's anatomy using patient-specific anatomical object recognition instead of an actual 3D printed physical template. The navigation system 1600 may navigate knee surgery instruments using one or more QR codes and/or object recognition. For example, the sequence may start with resection of the distal femur. In this case, the process may proceed as follows:

1. A QR cube may be affixed to the femur by the surgeon.
2. The AR device 200 may recognize the distal femur using object recognition, thus preliminarily registering the femur. The AR device 200 may also track the QR cube. Registration of the femur may be augmented by moving the hip around, watching the QR cube and/or distal femoral object, and calculating the hip center. For example, the AR device 200 may track the QR cube to calculate the hip center and may also or alternatively use object recognition to track the location of the distal femur during motion to triangulate to the hip joint center. This may be done before the QR cube or other tracker is affixed, but is preferably done after the tracker is attached. It should be understood that another tracking device, besides the QR cube may be used. In fact, it could just be another unique "object" that could also be tracked using object recognition as opposed to image recognition.
3. Once the femur is registered and holograms may be anchored, the AR device 200 may present one or more holograms of an ideal distal femoral cut plane. The surgeon may then put any distal cutting block in the field. In fact, a metal sheet may be placed into the saw blade slot of the cutting block, and the surgeon may place the cutting jig so that the metal sheet is coincident with the hologram of the distal cut plane hologram. The surgeon may then pin the jig in place, do the cut, and compare the cut to the hologram of the cut. The surgeon could then fine tune the cut, either through the jig or free-hand. Before projecting a hologram of the 4 in 1 cutting block, the AR device 200 may project a hologram of the proposed drill holes that would be needed for the pegs on the back of the 4 in 1 cutting block.
4. This process also may be applied to cutting blocks that provide multiple cutting planes, such as "4 in 1" cutting blocks. Typically, the 4 in 1 cutting block is affixed to the femur with two pegs or pins. The AR device 200 may display a hologram of the preferred locations of the pin hole, as planned, and the surgeon may drill holes to match the hologram, and put on the 4 in 1 cutting jig. Then, the AR device 200 may display a hologram of the preferred, e.g., planned, distal femoral preparation surface including the anterior, anterior bevel, distal, posterior bevel, and posterior cuts. These could be visually checked by the surgeon before making the cuts and again a metal sheet could be placed in the cutting slots to assist in lining up the physical 4 in 1 cutting block to the hologram thereof. Then, after the cuts are made and the 4 in 1 cutting block (or other jig) is removed, the AR device 200 may display a hologram of the cut surfaces as planned, and the surgeon can again fine tune the bone cuts either through the jig or free hand again to match the cut surfaces presented in the hologram.

The AR device 200 may project the ligament distraction with a hologram perpendicular to the tibia for the surgeon to check ligament balance and possibly change rotation of the 4 in 1 cutting block before completing this step.

5. At this point, the distal femoral preparation is complete. However, the AR device 200 can also display a hologram that shows the bone and the final femoral component on it.
6. The AR device 200 can register the tibia through object recognition of the exposed proximal tibial bone surface. In some embodiments, a tracker, such as a QR cube, may be placed on the tibia, e.g., to improve registration. The AR device 200 may present a hologram of the initial registration, and then rotating this hologram around manually, e.g., through user interaction by the surgeon, or automatically using the surgeon's palpation of the medial and lateral malleoli of the ankle. This process could replace traditional registration with image-free navigation of the knee, in which a tracker is put on the tibia and points are digitized on the proximal tibia. In addition, with traditional registration, the tip of the digitizer is placed on the skin compressed on the medial malleolus and then a second point is acquired with the tip of the digitizer placed on the skin compressed on the lateral malleolus. The traditional registration provides information on the longitudinal axis of the tibia. With the present technique, the longitudinal axis is included in the hologram. The surgeon puts a finger and thumb on the medial and lateral malleoli, and the hologram is then rotated to be placed between the finger and the thumb. In this way, the tibia is registered by moving the virtual axis in line with the ankle distally. This technique obviates the need for a digitizer. It may also leverage the capability of the AR device 200, which monitors the surgeon's hand and could be used to automatically determine the location of the surgeon's thumb and finger at the same time or allow a single finger to be the digitizer of the two ankle points. In some embodiments, a digitizer with a QR cube on it could be used to register the tibia. In other embodiments, object recognition of the specific digitizing object may be used to register the tibia. In sum, the systems could use various combinations of object recognition of the proximal tibia, direct digitization (which may require tracking two objects), tracking an object without a tracker on it such as the tip of the surgeon's finger or a standard, uniquely shaped digitizing instrument (the tip of which could be tracked by tracking the whole object using object recognition). Such an object-recognition-tracked-digitizer could be used to help with femoral registration as well. No QR cube needs to be included on the digitizer.

7. Once the tibia is registered and displayed in one or more holograms, the planned proximal tibial cut plane may be displayed in one or more holograms. In addition, the AR device 200 can also display in one or more holograms not only the tibia, but a model of whatever extramedually resection cutting jib is to be used. For simplicity's sake, if the AR device 200 displays just the cut plane, then the surgeon can put any cutting jig against the tibia, put a physical metal cut plane saw blade replacement through the tibial cut plane saw blade cutting slot, and then the instrument could be pinned to the tibia at that location, where the physical representation of the proposed cut plane matches with the hologram of the proposed cut plane. The cut could then be made and then the surgeon could compare the achieved cut plane to the planned cut plan as displayed by the hologram.

8. Additional tibial holograms that may be displayed by the AR device 200 include showing drill pin holes for placement of the tibial preparation tray that determines rotation and a keel for the tibial component. Another hologram that may be displayed by the AR device 200 may show the tibia and the tibial metal component with the proposed plastic insert within, i.e., the final implant appearance as planned.

9. A common method of determining femoral AP position and rotation is anatomically using the posterior femoral condyles. The posterior cut plane is typically a predetermined (e.g., 9 mm) distance from the backs of the two condyles and perpendicular to the distal cut plan. The anterior cut plane is then a fixed distance from the posterior and purely dependent upon the size of the proposed component. A surgeon, however, before just going with an anatomical measure, may check the ligament balance. This can be done by registering the tibia before the femoral preparation is finished. The tibial resection guide may be placed against the femur with the ligaments between the femur and tibia distracted by retractors. The surgeon can then visually check that the tibial jig is parallel to the proposed rotation of the femur (based on anatomical landmarks). This would show that the ligament balance would be good if the bone cuts are performed where proposed anatomically. In some embodiments, a similar process may be followed without the tibial jig, for example by displaying a hologram with a plane that is perpendicular to the long axis of the tibia onto the femur. With the ligaments distracted, it should match up with the pin holes of the 4 in 1 cutting jig. This can be checked by the surgeon before the femur is prepared. If the two methods (anatomic and ligament distraction) do not agree, the surgeon has a choice of releasing ligaments, changing the femoral rotation, or a combination of the two.

11. In some embodiments, the AR device 200 may display holograms of one or more Anterior Posterior (AP) cutting jigs used in knee surgery. The cutting jigs may be patient-specific or their locations recommended on a patient-specific basis and include indications of where bone cuts are to be made. During surgery, the AR device 200 may display the holograms at a planned location manually, automatically, e.g., using QR codes or object recognition, or a combination of manually and automatically.

The system may apply a similar technique to the tibia or any other body part internal or external.

Figure 13:
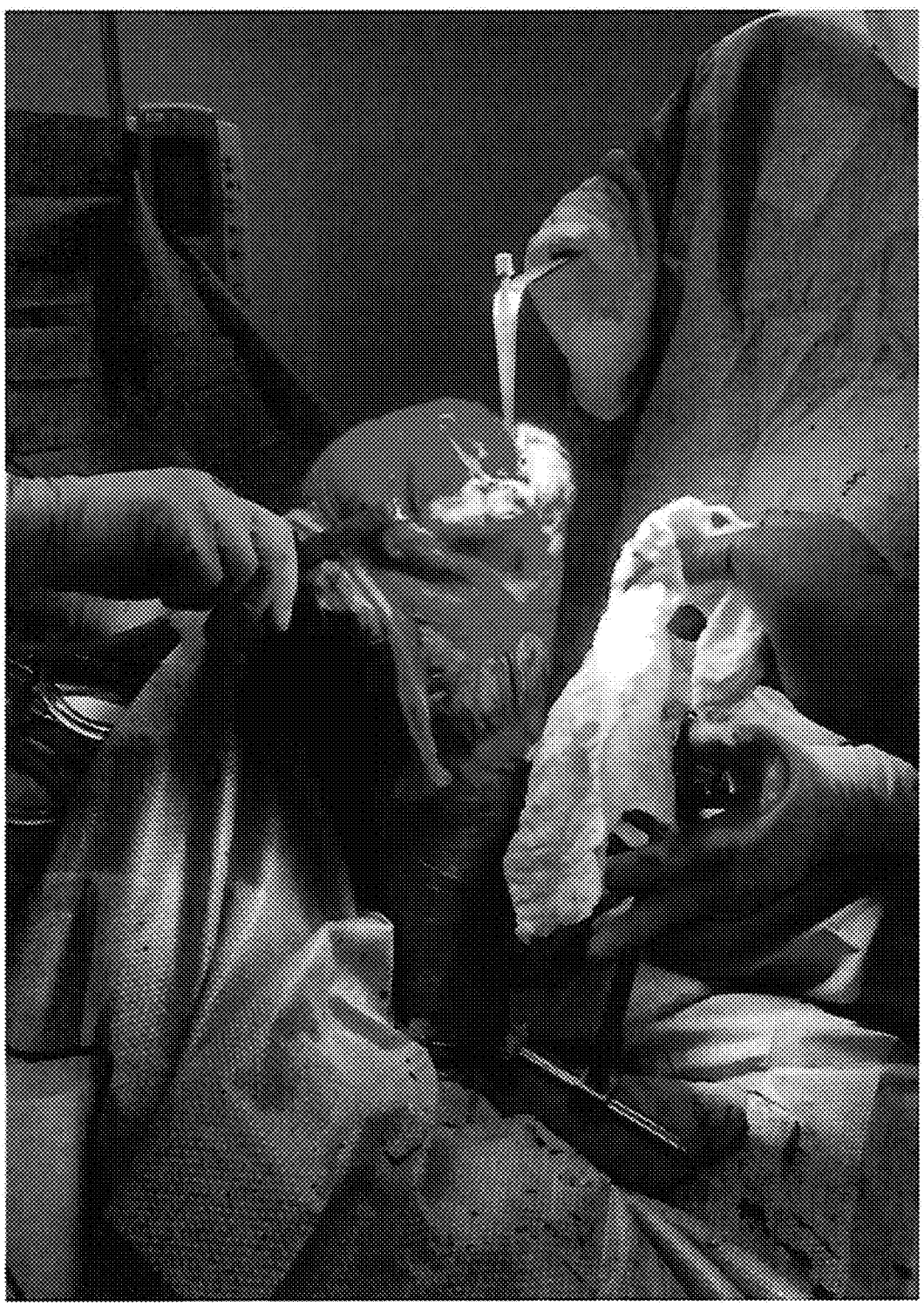
FIG. 13 is a pictorial representation of a patient's knee showing the tibia during total knee replacement in accordance with one or more embodiments.

FIG. 13 is a pictorial representation of a patient's knee showing the tibia during total knee replacement in accordance with one or more embodiments.

Figure 14:
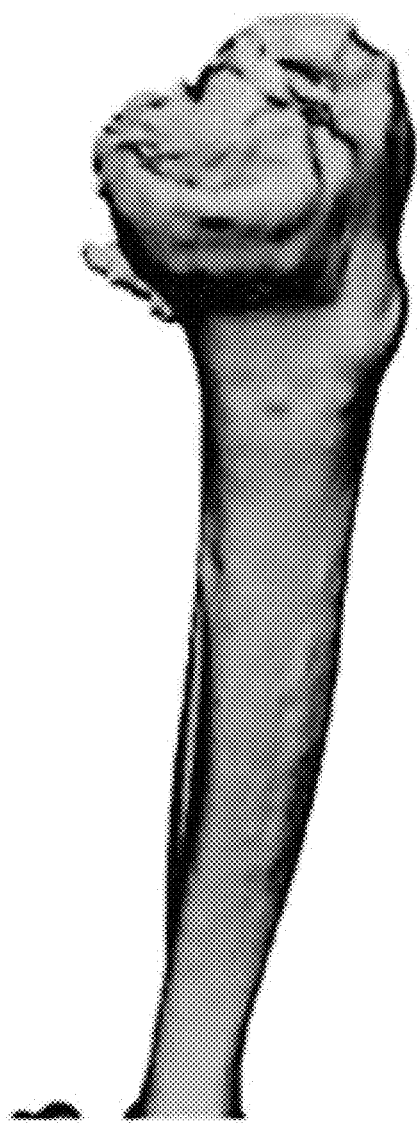
FIG. 14 is an illustration of a 3D surface model of the patient's tibia intended to depict the exact same bone in the exact same orientation as the surgeon's view in accordance with one or more embodiments.

FIG. 14 is an illustration of a 3D surface model of the patient's tibia intended to depict the exact same bone in the exact same orientation as the surgeon's view as determined by automated surface matching using stereoscopic cameras or any other method of stereoscopic surface detection in accordance with one or more embodiments.

Figure 15:
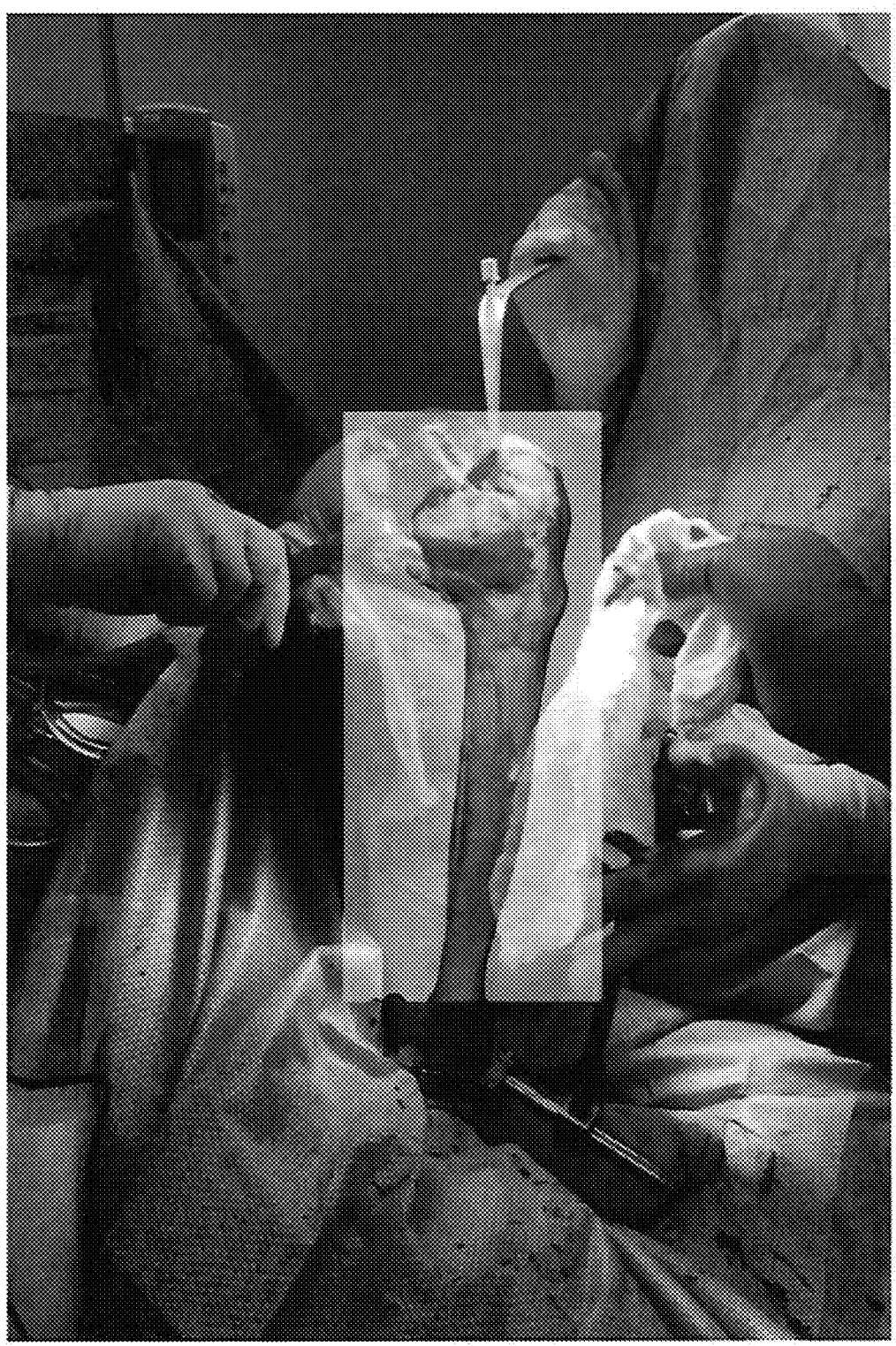
FIG. 15 is a schematic illustration of an image projected by an AR device showing a virtual model of the tibia placed in space in the exact same place as the actual tibia as seen from the surgeon's point of view in accordance with one or more embodiments.

FIG. 15 is a schematic illustration of a hologram projected by the AR device 200 showing a virtual model of the tibia placed in space in the exact same place as the actual tibia as seen from the surgeon's point of view in accordance with one or more embodiments.

Patient-specific anatomical object recognition and CAD file automated surface matching registration methodology may replace use of a physical template. The CAD file of the patient specific anatomical object to be recognized may be prepared pre-operatively with the object then recognized in surgery by searching the data provided by the spatial detection system of the AR device 200 to determine and track the location of the object.

The object may also be tracked either directly or indirectly, e.g., through another object associated with the primary object, such as a tracker placed on the pelvis or the femur, among other options. Again, the tracking may be performed by the spatial detection system (e.g., cameras and/or other sensors) on the AR device 200, the tracking system 106, or the 3D detection system 108, among others. The present disclosure may also eliminate having to make and sterilize a physical template and instead could be planned immediately. The present disclosure may eliminate extensive digitization of surfaces that might otherwise be necessary for image-free or image-based knee navigation.

Combinations of registration techniques (such as digitizing the ankle landmarks or triangulating the center of rotation of the hip joint) could be employed to improve accuracy further.

As noted, knee arthroplasty procedures generally require resection or cutting of both the patient's femur at its distal end and the patient's tibia at its proximal end. These resections or cuts are conventionally accomplished with the aid of cutting jigs or blocks that are placed on the respective bones and guide and direct the surgeon in the cutting of the bones at a desired location and orientation. In some embodiments, the cutting jigs or blocks may be patient-specific.

FEMUR DISTAL RESECTION. In a planning stage, a 3D model of a patient-specific distal femoral cutting jig or block may be created, e.g., based on a 3D model of the patient's femur. The location of the model of the femoral cutting jig or block on the femur may be planned so that the distal end of the femur will be cut as planned. The model of the femoral cutting jig or block may be used to generate a hologram for presentation by the AR device 200. During surgery, an anatomical structure or a tracker may be recognized, the AR device 200 may present the hologram of the femoral cutting block at the planned location at the distal end of the femur. In some embodiments, the surgeon may then co-locate the physical cutting block with the hologram, and secure the physical cutting block in place. The surgeon may then utilize the physical cutting block to resect the distal end of the patient's femur.

In some embodiments, the AR device 200 may present a hologram of an ideal cut plane so that the surgeon could double check the cut plane created by performing a bone preparation cut as guided by the physical cutting jig or block. In addition, with this embodiment, the surgeon may free-hand fine tune the resection of the distal end of the femur to more perfectly match the planned resection in the case that the cut that occurred through the cutting jig or block was close but not perfect.

TIBIAL RESECTION. As with the femur, a 3D model of a patient-specific proximal tibial cutting jig or block may be created, e.g., based on a 3D model of the patient's tibia. The location of the model of the tibial cutting jig or block on the tibia may be planned so that the proximal end of the tibia will be cut as planned. The model of the tibial cutting jig or block may be used to generate a hologram for presentation by the AR device 200. During surgery, an anatomical structure or a tracker may be recognized, the AR device 200 may present the hologram of the tibial cutting jig or block at the planned location at the proximal end of the tibia. In some embodiments, the surgeon may then co-locate the physical cutting block with the hologram, and secure the physical cutting block in place. The surgeon may then utilize the physical cutting block to resect the proximal end of the patient's tibia. Similarly as with the femur, the AR device 200 may present a hologram of an ideal cut plane.

Several methods may be used to plan the resections of the femur and tibia, including the ideal cut planes, and thus where to place the cutting jigs or blocks.

Method 1. Pure Anatomy. A basic way to determine the placement of the AP cutting jig is preoperatively, based purely on preop imaging. Many vendors of physical templates utilize this method. While this method is easy, it does not take ligament balance into consideration.

Method 2. Pure Ligament Balance. Known as the "Insall Technique" for Dr. John Insall. With this method, the distal femoral and proximal tibial resections are made more or less orthogonal to the long axis of their respective axes with minor variations depending upon surgical philosophy, but the rotation of the anterior and posterior cuts can be done with many different philosophies. In addition to a purely anatomic determination based on preop imaging (or intraop digitization), the opposite philosophy would be by ligament distraction technique. This is a classical method. Suppose that the tibia cut is more or less square to its long axis. Suppose further that the surgeon wants the back of the femur to be parallel to that so that when the knee is bent 90 degrees, that the back of the femur and the top of the tibia are parallel (with the ligaments distracted at the time of determination). This means that when the surgeon puts the implants in, that the ligament tension with the knee bent 90 degrees is more or less even. This method involves knee balancing using component rotation and/or soft tissue release as variables at the surgeon's disposal to accomplish this task.

Method 3. Blended Technique. With this method, a surgeon may look at femoral rotation using both methods 1 and 2 and see if they agree. If they do not, the surgeon may do slightly more ligament releasing to make the two methods a little closer to each other. This blended method basically moves method 2 closer to method 1.

Any of these methods may be implemented by the present disclosure.

In some embodiments, one or more guides may be used to determine where to place the cutting blocks or jigs. For example, the LEGION total knee system from Smith & Nephew Inc. of Memphis, Tenn. includes a sizing guide that uses the posterior femora condyles as a reference. The sizing guide may be used by the surgeon to determine where to place a cutting block or jig. In some embodiments, the same sizing guide may be used to correctly place a range of cutting blocks or jigs.

Figure 31:
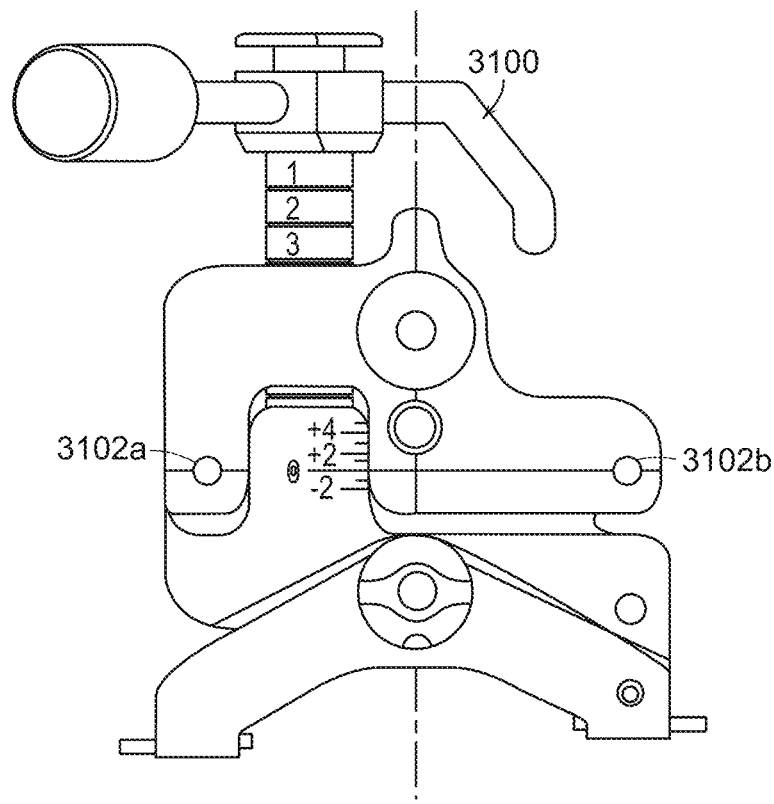
FIG. 31 is a front view of a sizing guide in accordance with one or more embodiments.

FIG. 31 is a front view of a sizing guide 3100 having two locator holes 3102*a* and 3102*b* in accordance with one or more embodiments.

Figure 32:
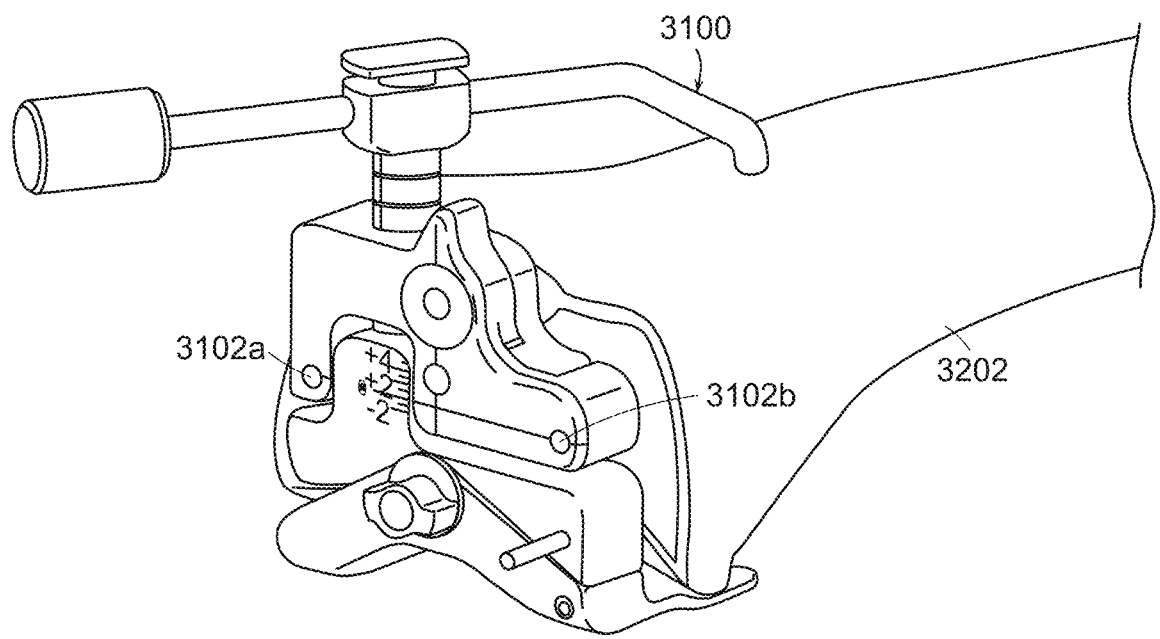
FIG. 32 is a perspective view of a sizing guide in accordance with one or more embodiments.

FIG. 32 is a perspective view of the sizing guide 3100 on a femur 3202 in accordance with one or more embodiments.

With the sizing guide 3100 attached to the patient's femur, a surgeon may utilize the locator holes 3102*a* and 3102*b* to drill two holes into the patient's femur. Next, the sizing guide 3100 may be removed and a cutting block or jig may be attached to the femur using the two holes determined by the locator holes 3102*a* and 3102*b* of the sizing guide 3100. The cutting block or guide may define correct Anterior, Posterior, and angled chamfer cuts for the implant.

Figure 33:
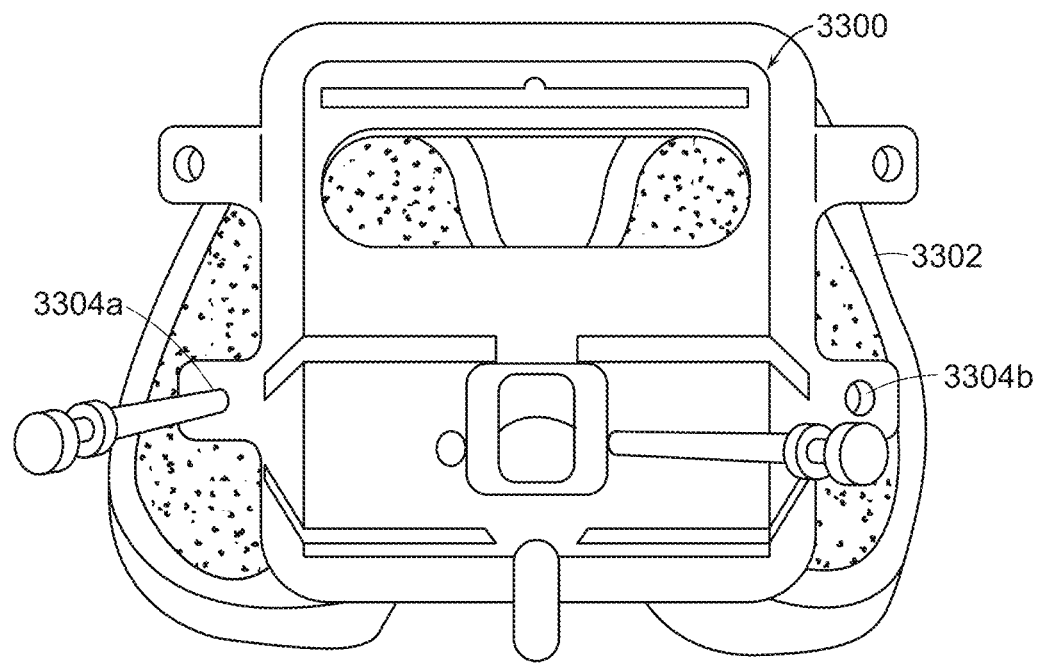
FIG. 33 is a front view of a cutting block in accordance with one or more embodiments.

FIG. 33 is a front view of a cutting block 3300 attached to a patient's femur 3302 in accordance with one or more embodiments. The cutting block 3300 may be attached to the patient's femur 3302 using pins or screws extending into drill holes 3304*a* and 3304*b* that were formed using the locator holes 3102*a* and 3102*b* of the sizing guide 3100.

Figure 34:
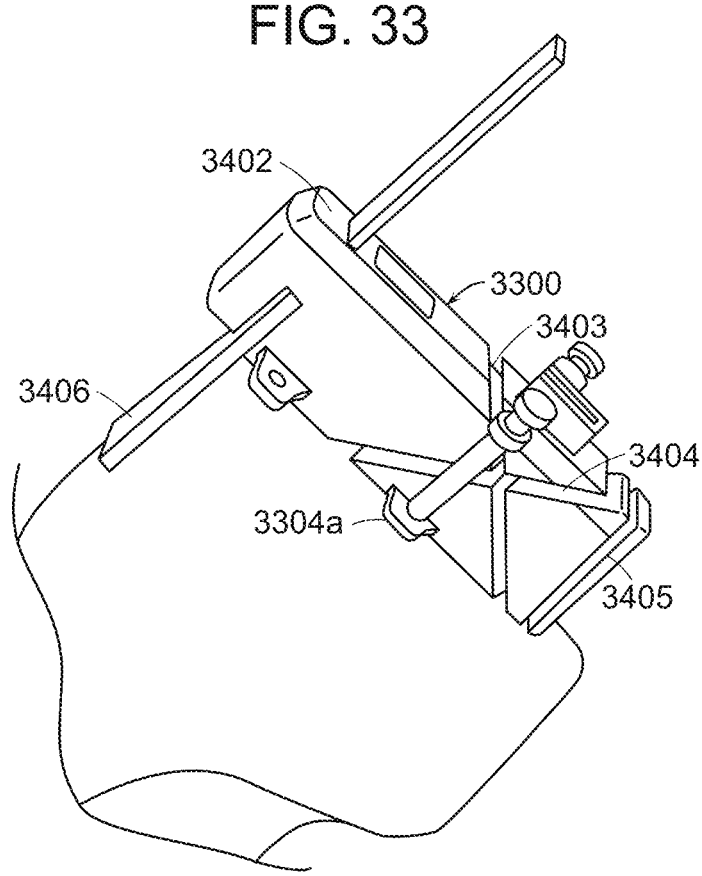
FIG. 34 is a side view of a cutting block in accordance with one or more embodiments.

FIG. 34 is a side view of the cutting block 3300 attached to the patient's femur 3302 in accordance with one or more embodiments. The cutting block 3300 provides an Anterior cutting guide 3402, a Posterior cutting guide 3405, and two angled chamfer cutting guides 3403 and 3404. A surgeon may place a saw blade 3406 in the cutting guides, e.g., the Anterior cutting guide 3402, of the cutting block 3300 to make the planned cuts.

In some embodiments, the AR device 200 may present holograms of the planned locations of the locator pin holes. During surgery, these holograms may be presented and surgeon may use the holograms to align a drill to drill the locator pin holes at the planned locations. For example, a hologram of the sizing guide having drill holes may be presented by the AR device 200. In this implementation, the surgeon may not use the physical sizing guide or any other guide. After drilling the locator pin holes based on the one or more holograms presented by the AR device 200, the surgeon may install the cutting block or guide on the patient's femur. In some embodiments, the AR device 200 may present holograms of the planned Anterior, Posterior, and angled chamfer cutting planes as planned. The surgeon may then check that these holograms of the cutting planes are co-located, e.g., aligned, with the cutting guides of the physical cutting block or jig.

After making the cuts, the surgeon may implant a prosthetic knee component.

Figure 35:
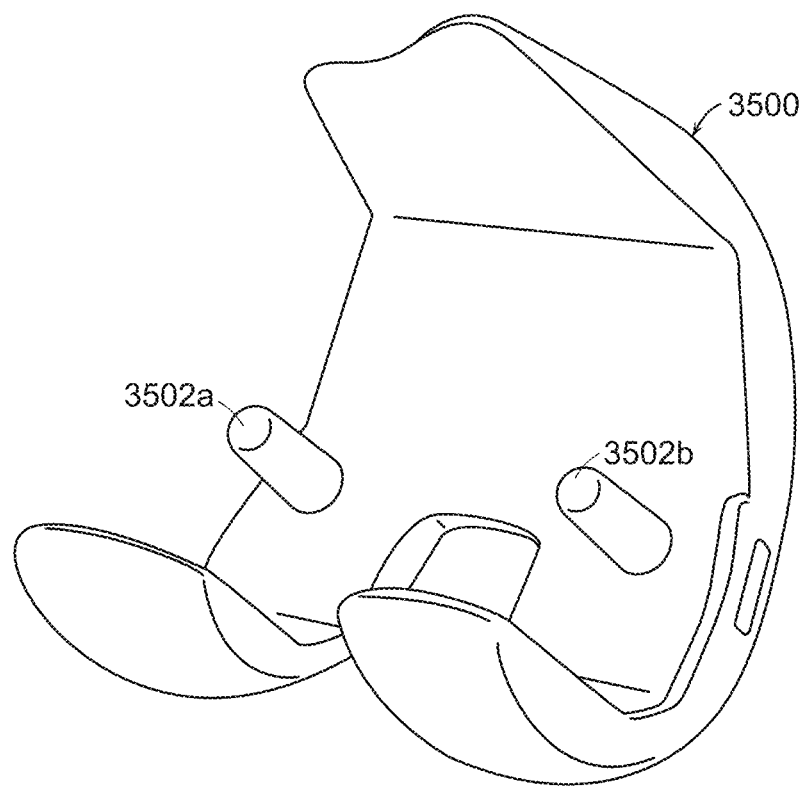
FIG. 35 is a perspective view of a prosthetic knee component in accordance with one or more embodiments.

FIG. 35 is a perspective view of a prosthetic knee component 3500 in accordance with one or more embodiments. The knee component 3500 may include interior surfaces that match the Anterior, Posterior, and angled chamfer cuts made to the patient's femur. In addition, the knee component 3500 may include two pins 3502a and 3502b that may be received in the drill holes that were formed based on the hologram of the locator pin holes.

It should be understood that other guides and/or cutting blocks may be used, such as a five-in-one cutting block or jig, among others.

Other Knee Solutions

It should be understood that other procedures may be utilized.

Pre-operative imaging of the patient's knee may be performed using CT, MR, or other imaging techniques. Alternatively, statistical shaped models having minimal patient-specific information for model fitting may be used.

Software steps may include segmentation of femur and tibia. Landmarks and coordinate systems may then be created. For example, the femoral coordinate system rotation could initially be determined by the posterior femoral condyles.

Next, a plan for the femoral component may be created with the following initial criteria:
1. Distal femoral cut perpendicular to the long axis of the femur in the coronal plane and in a few degrees of flexing in the sagittal plane.
2. The distal cut plane is to be Xmm (e.g., 8 mm or 9 mm) from the most distal cartilage surface of the femur.
3. The posterior and anterior cut planes of the femur are planned such that the posterior cut plane is Xmm anterior (e.g., 8 or 9 mm) anterior to the posterior femoral condyles and perpendicular to the distal femoral resection (unless the particular implant system calls for a slight angle). The anterior cut may be parallel to the posterior cut and determined by the size of the planned femoral component which is in turn determined by the size of the femur.

A plan for the tibial component may be created with the following initial criteria:
1. The proximal tibial resection plane may be perpendicular to the long axis of the tibia on the coronal plane and typically in a few degrees of flexion in the sagittal plane. One way to determine the rotation of the tibial coordinate system, since the knee may have been in extension during the imaging, is to just project the femoral condylar rotation onto the tibia. Another way is to use one or two more anatomical points in addition to the point where the tibial long axis exits the proximal tibia. In addition, the depth of the resection plane below the tibial surface could be either Xmm below the lowest tibial plateau surface or Xmm below the highest tibial plateau surface. This could be a surgeon preference variable.

The AR device 200 may be configured to present the following sequence of static holograms:

F01. The native femur.

F02. The native femur with the distal femoral cut plane.

F03. The native femur, distal femoral cut plane, and generic or impact specific traditional distal femoral resection guide.

F04. Two drill hole holograms that would project into the distal femur that would tell the surgeon where to drill holes so that when a specific "4 in 1" femoral cutting jig is placed using the locating pins on the back surface of jig, the anterior and posterior bone cuts (and chamfer cuts) made using the jig are in the planned locations.

F05. Hologram of the preferred prepared surface of the distal femur that has modified the femur to reflect the distal, anterior, posterior, and chamfer bone cuts.

F06. A hologram of the femur with the femoral component of the planned size in the planned place.

INSALL-technique holograms. The above describes preparing the femur based purely on anatomical landmarks. In some embodiments, ligament balance may be assessed in surgery. One or more holograms may be pre-generated and pulled from a patient specific holographic library for the surgery during ligament balance.

Suppose, the AR device 200 is tracking the tibia and displaying holograms relative to the tibia. Suppose further that a determination is made regarding where the proximal tibial resection will be. Assume the femoral and tibial implant thicknesses taken together are X mm (e.g., 5 mm above the low side of the tibial surface and another 9 mm for the posterior portion of the femoral implant). The surgeon may distract the ligaments and the AR device 200 may project a hologram of a cut plane relative to the tibia in that location. The hologram may be projected upon the femur. This hologram projection may be compared to where the pin holes and posterior cut plane suggested by anatomical landmarking would be.

If the system projected the hologram based on tracking the tibia and also projected a hologram simultaneously based on tracking the femur, these two holograms should ideally overlap. To the extent they differ, the surgeon has several choices:

A. the surgeon may stick with the anatomical position and rotation based in the femoral anatomy, ignoring the tibial information, B. the surgeon may use the tibial/ligament distraction recommendation, C. the surgeon may do more ligament releasing to get the two holograms to line up more closely, and D. with or without C, the surgeon may choose a femoral position somewhere between A and B.

The AR device 200 may present the following tibial holograms:

T01. A hologram of the native tibia.

T02. A hologram of the native tibia plus the preferred tibial cut plane.

T03. T02 plus a proximal tibial cutting jig, either generic or vendor system specific.

T04. A hologram projected on the cut tibial surface that has drill hole projections onto the tibial surface marking where the drill holes would go for the tibial tray jig that is affixed to the tibia in the correct position and rotation and for allowing the Keel Punch preparation to be in the correct place.

T05. A hologram of the tibia reflecting the ideal tibial resection plus the planned tibial component in the correct position and rotation.

Registration and Tracking.

For the femur, a tracking object, such as a cube with one or more QR codes, may be attached in a predetermined location. The AR device 200 may then register the femur primarily using object recognition of the unique patient specific distal femoral anatomy. Registration of the femur may be augmented by other classical methods, such as kinematic triangulation of the femoral head center, direct landmark digitization through the incision, or even REVERSE REGISTRATION, in which the AR device 200 may project a hologram and the surgeon may move the limb into position to overlap the hologram. The AR device 200 may then anchor the hologram at this location.

The tibia could be registered using the reverse registration methodology, since the proximal tibial surface is less distinct in its unique geometric characteristics than the distal femur.

When trial or real implants are in place, the AR device 200 can track both the femur and tibia and project above described holograms T05 and F06, e.g., in real time, as the knee is moved about. The AR device 200 may also calculate alignment and motion and ligament balance.

ACL Reconstruction.

Anterior cruciate ligament (ACL) reconstruction is the most common major non-prosthetic reconstruction procedure on the knee. The current state of the art is to perform arthroscopy and to:

1. debride the stumps of the ruptured ACL,
2. prepare the "notch" of the femur,
3. use anatomic landmarks to determine the femoral and tibial attachment points of the new ligament,
4. place a drill hole through the tibia with the hole in the joint at the proposed tibial attachment point,
5. place a drill hole into the femur with the hole location in the joint at the proposed femoral attachment point,
6. thread the ligament through,
7. secure the femoral attachment using an interference screw (for a bone-ligament-bone graft),
8. tension the ligament, and
9. secure the tibial attachment, again using an interference screw (for a bone-ligament-bone graft).

The procedure is slightly different if a soft tissue graft is used since it is tied down with other fixation methods.

Some of the disadvantages of the current state of the art include:

1. performance of the procedure requires constant visualization within the joint and any clouding of the fluid with bleeding or debris prevents that visualization.
2. determination of the "isometric points" for the tibia and femoral attachments of the graft is not scientifically determined and placing the graft in the wrong location can lead to early rupture.

As described herein, the system of the present disclosure may implement the following technique:

1. optionally, the AR device 200 could be used as both the tracking and visualization technology.
2. Preoperative CT/MR or predictive shape modeling. Create 3D models for "virtual template" object recognition registration in surgery.
3. in surgery, attach tracking objects to the femur and tibia percutaneously that can be recognized and tracked by the spatial detection system of an augmented reality HMD.
4. utilize an arthroscopy camera that has: a) stereoscopic vision or a similar spatial detection system inside the joint at the working end and b) a tracking object on the end that is outside of the body that can be tracked by the spatial detection system of the AR device (or any other tracking method). The technique may utilize two spatial detection systems: one within the joint that can be used to visualize the anatomy for "virtual template" registration and the second being, for example on the AR device 200, that can watch the position of the external end of the arthroscopy device.
5. for femoral registration, the spatial detection system on the arthroscopy device is aimed at the femoral joint surface or any aspect of the femur visible within the joint. The edges of the joint surface, for example, may be used in object detection. With the external spatial detection system watching the position of the arthroscopy device, the knee is moved through a range of motion to be able to identify enough of the unique CAD surface of the femur to determine where the femur is in space relative to the tracker previously placed on the femur. As in the other examples, a patient-specific CAD or other image file may be created, such as a CAD file of the surface of the patient's femur or a portion thereof, such as the distal end of the patient's femur. Furthermore, a patient-specific coordinate system may be determined pre-operatively relative to this object, e.g., the patient's femur. The navigation system 1600 may then search for and detect this object in the image data obtained from the spatial detection system on the AR device 200 of the surgical scene. Once detected, the navigation system 1600 may also register the actual object, e.g., based on the pre-operatively determined, patient-specific coordinate system. The navigation system 1600 would then register the location of the entire femur in space.
6. for tibial registration, the spatial detection system on the arthroscopic device may be aimed at the tibial joint surface. With the external spatial detection system (or other tracking solution), the tibia can be registered. Here, the process includes a preoperative CAD file of the tibial surface based on MRI, and the navigation system 1600 can recognize the exact location of that surface using the internal arthroscopic spatial detection system with the external reference frame attached. The endoscope may be moved to capture more of the surface, such as the surface of the tibia.
7. Proposed attachment points on the tibial and femoral surface may be planned based on anatomy on the MR. Alternatively, after registration, the knee may be cycled through the range of motion in an "ACL competent" position (pressure tensioning the PCL during motion). In this way, the system may calculate optimal isometric points on the femur and tibia.
8. Now that the system knows where the femur and tibia are at all times and where the ideal attachment points are as the ligaments attach in the knee, the system can display the femur and tibia on the AR device 200 from whatever viewpoint the surgeon 114 has at that moment. The system can also show the proposed course of tibial and femoral tunnels for optimal ACL reconstruction. In addition, the system can track any tools including traditional tunnel creating instruments and show the tools in augmented reality and show the virtual project of the proposed tunnel relative to those tools.

At least some of the advantages of the present disclosure include: ACL reconstruction can be performed more reliably since the attachment points would be more reliably placed, reducing the risk of ACL reconstruction failure. The methodology has the further benefit that most of the critical parts of the procedure can be done with augmented reality, reducing the need for arthroscopic visualization, allowing for refining the surgery for visualization with arthroscopy just at specific points during the procedure instead of continuously. In addition to better technical excellence, with proper refinement, the surgery potentially could be performed more efficiently.

Dental Surgery.

Dentists generally place dental implants without navigation or enhanced visualization of any kind. Dentists may rely on plain radiographs and/or CT imaging with multiplanar reformatting, which can show where the available bone is upon which to base a dental implant. However, problems can arise if the bone is quite thin, which can occur particularly on the buccal side of the maxilla or mandible or when teeth have been missing for some time, and if landmarks such as adjacent teeth are not available to spatially guide the dentist. Traditional image-based navigation is rarely used in this field for reasons such as complexity, cost, and the fact that the patient is in one place, and the navigation information is in another, such as on an LCD screen.

Holographic guidance during dental implant surgery may represent a significant and cost-effect advance in this field. The anchoring of holographic guidance may be based at least in part on one or more existing teeth, which are physically available as opposed to being deeply under the skin.

In some embodiments, the present disclosure may include:

1. Create a dental mold on at least a portion of a patient's mandible or maxilla, depending on which side of the jaw needs an implant. The mold may include any available teeth that would allow attachment of a tracker that could be outside of the mouth. Such a tracker could be a traditional dynamic reference base (DRB) for infrared (IR) stereoscopy tracking, or in some embodiments a QR code or other recognizable image or object that can be identified and continuously tracked by the navigation system 1600. The location of the mold may be adjacent to the location of the proposed dental implant or other proposed procedure while spaced far enough away to still provide access to the area at which the implant or other dental surgery will be located. In some embodiments, the mold may include an element from which the location of the tracker can be determined. The element may be the tracker itself, a tracker support, a tracker attachment mechanism, or information, such as dots or dimples on the mold, from which the location of the tracker may be determined.

2. With the mold in place on the patient's jaw, obtain a CT or other imaging study of the patient prior to the procedure. The CT or other imaging includes the element or information from which the location of the tracker may be determined. For example, in some embodiments, the tracker may be attached to the mold when the CT or other imaging is performed. In other embodiments, the tracker support or tracker attachment mechanism may be included with the mold, but the tracker itself may be omitted, when the CT or other imaging is performed.

3. The surgical planning system 1700 can use the CT or other imaging to plan the location of the implant and to identify exactly where the tracker, e.g., the QR code or other tracking image or object will be located within the CT coordinate space. For example, a computer-generated 3D model of the patient's mandible or maxilla including the mold and tracker may be generated. A planner may select one or more particular tools, e.g., drills, drill bits, etc., and/or implants and determine locations of the surgical tools and/or implants relative to the 3D model. For example, 3D models of the surgical tools and/or implants may be combined with the 3D model of the mandible of maxilla to form new 3D models.

4. Having the tracker or a mold to which the tracker will be attached on the patient before the imaging may simplify the patient registration process, for example because the tracker location is already known. This is in contrast to registering the pelvis for hip surgery where the CT study is performed without a tracker affixed and then the location of the pelvis is determined during the surgery, such as by docking a registration and tracking tool to the pelvis or affixing a tracker then registering the location of the pelvis relative to the tracker subsequently.

5. With the tracker affixed to the patient in a known way, the surgical planning system 1700 can utilize combinations of the 3D models to generate one or more static and/or dynamic holograms for display by the AR device 200. In some embodiments, at least some of these holograms may show the patient anatomy otherwise not visible to the dentist and be co-located with actual patient anatomy, e.g., that may be visible to the dentist and thus the AR device 200.

6. Exemplary holograms may include one or more holograms of the patient's mandible or maxilla without the implant and one or more holograms of the patient's mandible or maxilla with the surgical tools and/or the implant at the planned locations. By presenting such holograms using the AR device 200, the dentist can "see" exactly in 3D where the patient's bone is located to properly anchor an implant.

7. During the surgical procedure, the mold and tracker may be inserted in the patient's mouth. The AR device 200 as worn by the dentist may recognize the tracker and may present and anchor the one or more holograms in space relative to the tracker so that the holograms of the mandible or maxilla are co-located with the patient's physical mandible and maxilla and the holograms of the surgical tools and/or implant are presented at their planned locations.

8. The dentist may utilize the one or more holograms as guides in operating the surgical instruments and implanting the implant.

9. In some embodiments, the AR device 200 worn by the dentist may present the CT data volume for the patient's mandible or maxilla co-located with the patient's mandible or maxilla during the procedure. For example, the AR device 200 may generate one or more planar cuts, e.g., cut planes, through the CT data volume to produce a two dimensional (2D) CT image from the CT data. The AR device 200 may present this 2D CT image to the dentist. By co-locating the CT data volume with the patient, the 2D CT image, as displayed by the AR device 200, may appear to the dentist as overlaid on and co-located with the patient's anatomy. The cut plane may be set at a predetermined distance from the AR device 200.

10. It should be understood that the surgical planning system 1700 may generate other, e.g., more sophisticated, holograms such as one showing the exact trajectory of a planned drill hole, or the exact size and location of the implant itself. Furthermore, the navigation system 1600 and the surgical planning system 1700 may update the holograms, e.g., in real time from the perspective of the dentist, to show the effect of any tools that have been used up until that point in the procedure.

One advantage of such a methodology is that the entire planning and navigation process may be performed on the spot in a single session where the custom dental mold for the tracker is affixed to one or more of the patient's available teeth, the imaging can then take place, the planning and holograms can be quickly performed and generated, and the implant intervention can then take place. Another advantage is that the tracker/dental mold apparatus may be removed and replaced onto the patient that day or another day with the reapplication of the tracker going back to the same exact place that it was previously. Accordingly, any number of procedures may be performed on the same day or subsequent days using the same planning and registration or updated planning with the same registration. A third advantage is that this methodology and technology is inexpensive.

Figure 56:
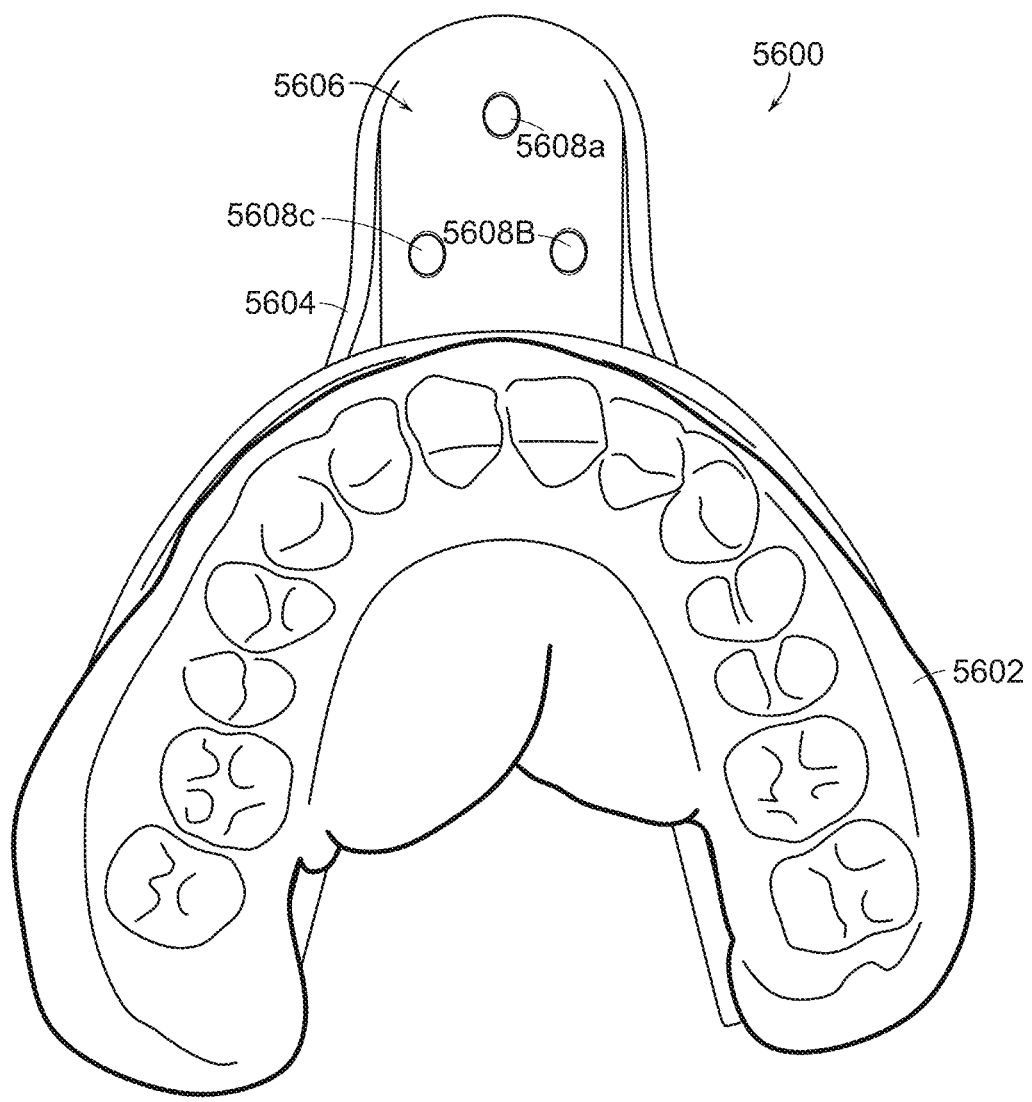
FIG. 56 is a top view of an example dental model in accordance with one or more embodiments.

FIG. 56 is a top view of an example dental model 5600 in accordance with one or more embodiments. The dental mold 5600 includes an impression 5602 of a patient's teeth. The dental mold 5600 also includes a projection 5604. Disposed on the projection 5604 is a pattern indicated at 5606. The pattern 5606 is formed from a plurality, e.g., three, markings 5608a-c. During the surgical procedure, the AR device 200 may recognize the pattern 5606 and may anchor one or more holograms relative to the pattern 5606.

Figure 53:
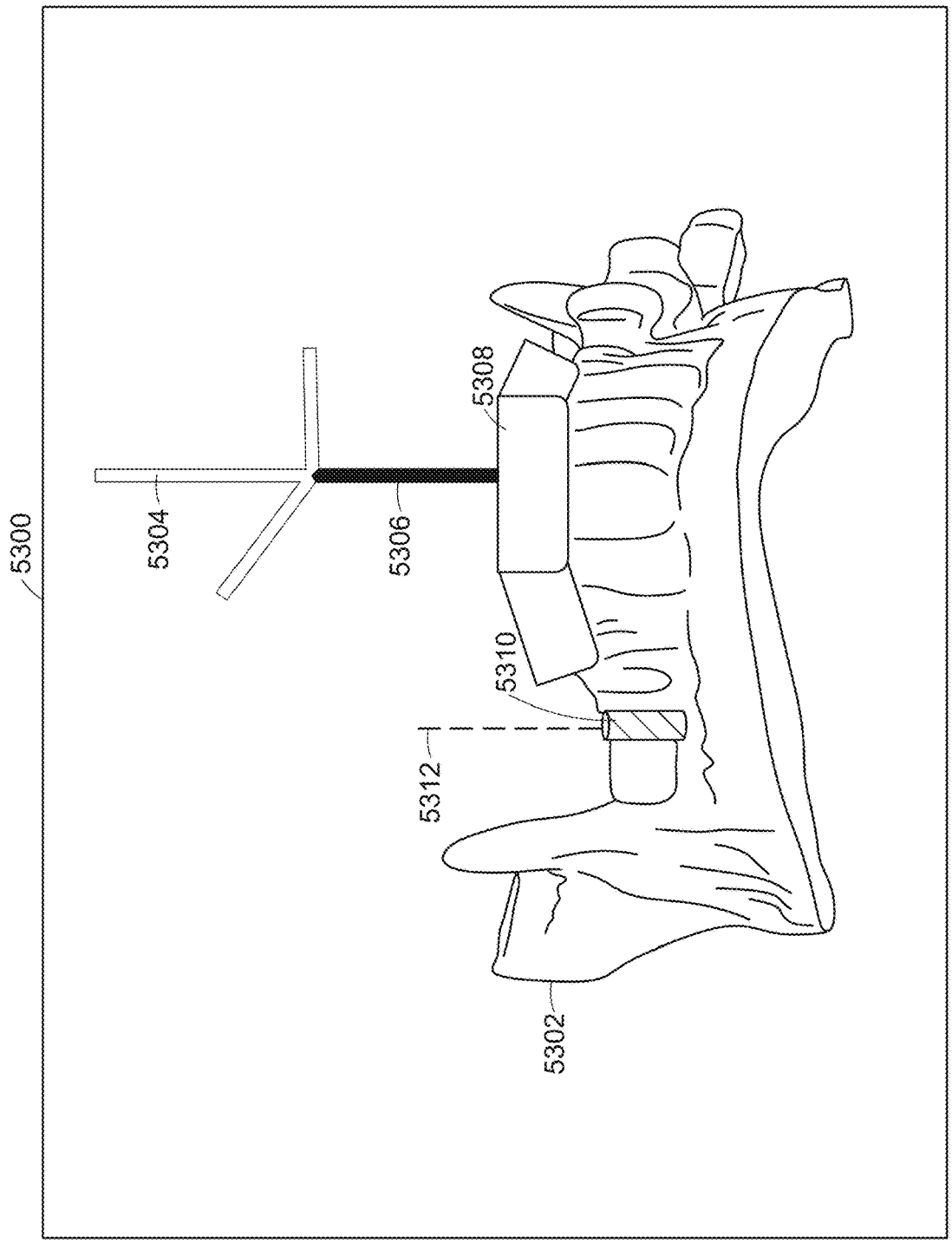
FIG. 53 is an illustration of a planning window in accordance with one or more embodiments.

FIG. 53 is an illustration of a planning window 5300 in accordance with one or more embodiments. The planning window 5300 includes a 3D model of a patient's mandible 5302 and a 3D model of a tracker 5304 attached to a 3D model of a tracker support 5306. The tracker support 5306 may be attached to a dental mold 5308 on the patient's mandible 5302. Locations of one or more surgical instruments and one or more implants may be planned to achieve one or more goals. For example, a model of an implant 5310 may be placed at the mandible 5302 at a planned location. Alternatively or additionally, a drill axis 5312 for drilling into the mandible 5302 to receive the implant may be planned at a preoperatively determined location. One or more holograms may be generated from the models created in the surgical plan and the holograms may be presented by the AR device 200 and anchored relative to the tracker 5304.

Figure 54:
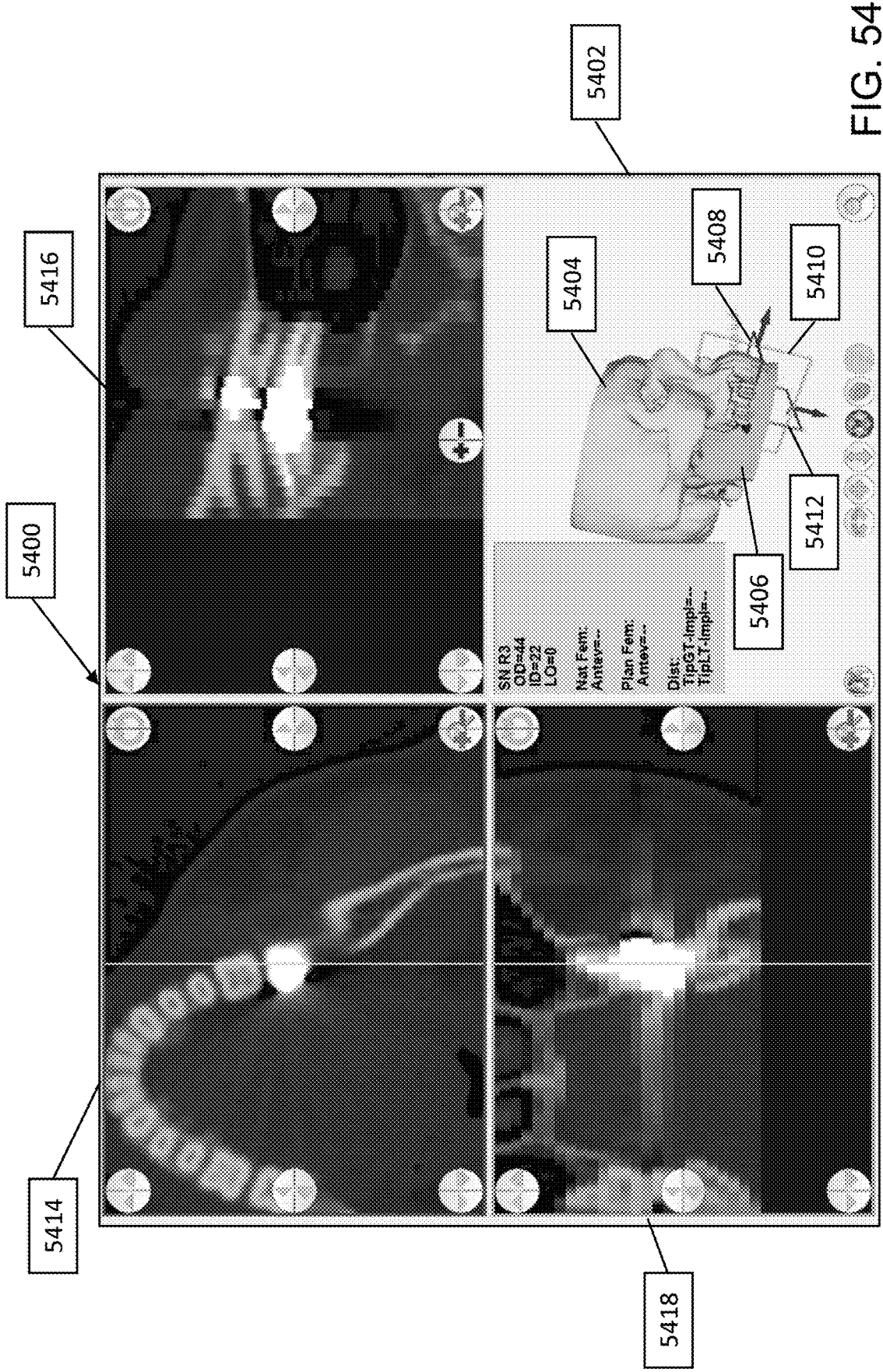
FIG. 54 is an illustration of cut planes that may be presented by an AR device during a surgical procedure in accordance with one or more embodiments.

FIG. 54 is an illustration 5400 of cut planes that may be presented by the AR device 200 during a surgical procedure in accordance with one or more embodiments. The illustration includes a first pane 5402 that shows a 3D surface model of the 5404 of at least a portion of a patient's jaw including the patient's mandible 5406. Superimposed on the 3D surface model 5404 are three boxes illustrating orthogonal cut planes. A red box 5408 signifies one image-generation plane, a yellow box 5410 signifies a second image-generation plane, and a green box 5412 signifies a third image-generation plane. The illustration 5400 includes additional panes presenting cut planes through CT volume data of the patient corresponding to the planes of the boxes 5408, 5410 and 5412, which may be presented by the AR device 200 in the exact location within the patient's jaw. For example, a pane 5414 illustrates a cut plane through the CT volume data for the red box 5408. A pane 5416 illustrates a cut plane through the CT volume data for the yellow box 5410. A pane 5418 illustrates a cut plane through the CT volume data for the green box 5412.

Neurosurgery/Ear Nose Throat (ENT) Surgery

Holographic guidance during neurosurgery and/or ENT surgery also may represent a significant and cost-effect advance in this field. As with the dental surgery embodiment, the holographic guidance may be based at least in part on one or more existing teeth. For example, a dental mold for example of a patient's upper teeth (as they are fixed relative to the patient's skull) may be made and a tracking object such as a QR code may be affixed to the dental mold. Imaging may then take place, during which the tracking object (e.g., QR code) may be identified on the images, and then the rest of the procedure may be planned. This embodiment may use the upper teeth and a prior-to-imaging application of a tracker that can then be included in the preop plan so that registration may be instant, automatic, and accurate.

It should be understood that additional and/or alternative registration techniques may be used. To improve the registration accuracy, the "virtual template" registration method may be combined with other methods. For the femur, triangulation of the center of rotation of the hip can be calculated by moving the hip around with a stereoscopic camera tracking the tracker attached to the femur. Combining this with the virtual template registration could further refine the accuracy of registration. Combining digitization with the virtual template registration could further refine the accuracy of registration.

The foregoing description of embodiments is intended to provide illustration and description, but is not intended to be exhaustive or to limit the disclosure to the precise form disclosed. Modifications and variations are possible in light of the above teachings or may be acquired from a practice of the disclosure. For example, while a series of acts has been described above with respect to the flow diagrams, the order of the acts may be modified in other implementations. In addition, the acts, operations, and steps may be performed by additional or other modules or entities, which may be combined or separated to form other modules or entities. Further, non-dependent acts may be performed in parallel.

Further, certain embodiments of the disclosure may be implemented as logic that performs one or more functions. This logic may be hardware-based, software-based, or a combination of hardware-based and software-based. Some or all of the logic may be stored in one or more tangible non-transitory computer-readable storage media and may include computer-executable instructions that may be executed by a computer or data processing system. The computer-executable instructions may include instructions that implement one or more embodiments of the disclosure. The tangible non-transitory computer-readable storage media may be volatile or non-volatile and may include, for example, flash memories, dynamic memories, removable disks, and non-removable disks.

No element, act, or instruction used herein should be construed as critical or essential to the disclosure unless explicitly described as such. Also, as used herein, the article "a" is intended to include one or more items. Where only one item is intended, the term "one" or similar language is used. Further, the phrase "based on" is intended to mean "based, at least in part, on" unless explicitly stated otherwise.

The foregoing description has been directed to specific embodiments of the present disclosure. It will be apparent, however, that other variations and modifications may be made to the described embodiments, with the attainment of some or all of their advantages. Therefore, it is the object of the appended claims to cover all such variations and modifications as come within the true spirit and scope of the disclosure.

What is claimed is:

1. A system comprising:
a registration and tracking device configured to dock to a portion of a patient's pelvis in a predetermined and fixed location;
a computer-based surgical planning system configured to:
present a two-dimensional (2D) or a three-dimensional (3D) model of the portion of the patient's pelvis;

determine a location for a 3D model of the registration and tracking device as docked to the 2D or 3D model of the portion of the patient's pelvis;
establish a coordinate system for the registration and tracking device;
determine a location of one or more surgical tools relative to the coordinate system for the registration and tracking device;
generate one or more files from which a plurality of holograms may be produced of combinations of two or more of:
the 2D or 3D model of the portion of the patient's pelvis;
the registration and tracking device; and
the one or more surgical tools; and
an augmented reality (AR) head-mounted device (HMD), the AR HMD including:
at least one sensor configured to recognize at least a portion of the registration and tracking device;
one or more projectors configured to present the plurality of holograms; and
a navigation system that tracks the registration and tracking device and anchors the plurality of holograms in a space based on the coordinate system for the registration and tracking device.

2. The system of claim 1, wherein the computer-based surgical planning system is further configured to determine a location of at least one implant relative to the coordinate system for the registration and tracking device and the plurality of holograms further include the at least one implant.

3. The system of claim 1, wherein
the registration and tracking device includes a three dimensional (3D) shape having a surface and one or more markings is disposed on the surface of the 3D shape, and
the at least one sensor of the AR HMD recognizes the one or more markings on the surface of the 3D shape of the registration and tracking device.

4. The system of claim 3 wherein the one or more markings is one or more Quick Response (QR) codes or a checkerboard pattern.

5. The system of claim 1 wherein
the registration and tracking device includes a hub having a predetermined and fixed shape and three legs extending from the hub, the three legs configured to dock the registration and tracking device to the portion of the patient's pelvis, and
the at least one sensor of the AR HMD recognizes the hub of the registration and tracking device.

6. The system of claim 1 wherein the computer-based surgical planning system is further configured to:
determine a location of the one or more surgical tools relative to a coordinate system for the 2D or 3D model of the portion of the patient's pelvis; and
generate one or more transformation matrices between the coordinate system for the 2D or 3D model of the portion of the patient's pelvis and the coordinate system for the registration and tracking device, and
wherein the AR HMD utilizes the one or more transformation matrices to anchor the plurality of holograms in the space.

7. The system of claim 1 wherein the computer-based surgical planning system is further configured to determine a sequence of presentation for the plurality of holograms and the AR HMD presents the plurality of holograms in the sequence of presentation.

8. A computer-implemented method comprising:
presenting a two-dimensional (2D) or a three-dimensional (3D) model of a portion of a patient's pelvis;
determining a location of a registration and tracking device as docked to the 2D or 3D model of the portion of the patient's pelvis;
establishing a coordinate system for the registration and tracking device;
determining locations of one or more surgical tools and at least one implant relative to a coordinate system for the 2D or 3D model of the portion of the patient's pelvis;
generating files for presenting holograms of the one or more surgical tools and the at least one implant at the determined locations relative to the coordinate system for the 2D or 3D model of the portion of the patient's pelvis;
generating a transformation matrix between the coordinate system for the 2D or 3D model of the portion of the patient's pelvis and the coordinate system for the registration and tracking device; and
exporting the files to an augmented reality (AR) head-mounted device (HMD).

9. A computer-implemented method comprising:
recognizing a registration and tracking device as docked to a portion of a patient's pelvis, the recognizing including tracking a location of the registration and tracking device;
receiving files for presenting holograms of one or more surgical tools and at least one implant at determined locations relative to a coordinate system for the patient's pelvis;
receiving a transformation matrix determining orientations and positions of the holograms relative to a coordinate system for the registration and tracking device; and
utilizing the transformation matrix to present the holograms anchored at the determined locations.

10. The computer-implemented method of claim 9 wherein
the registration and tracking device includes a hub having a predetermined and fixed shape and three legs extending from the hub, the three legs configured to dock the registration and tracking device to the portion of the patient's pelvis, and
the recognizing the registration and tracking device includes recognizing the hub of the registration and tracking device.

11. The computer-implemented method of claim 9 wherein
the registration and tracking device includes a three dimensional (3D) shape having a surface and one or more markings is disposed on the surface of the 3D shape, and
the recognizing the registration and tracking device includes recognizing the one or more markings on the surface of the 3D shape of the registration and tracking device.

12. The computer-implemented method of claim 11 wherein the one or more markings is one or more Quick Response (QR) codes or a checkerboard pattern.

13. A system comprising:
a computer-based surgical planning system configured to:
present a two-dimensional (2D) or a three-dimensional (3D) model of a patient's knee;
establish a coordinate system for the patient's knee;

determine a location of one or more cut planes to the patient's knee relative to the coordinate system for the patient's knee;

determine a location of at least one implant for the patient's knee relative to the coordinate system for the patient's knee;

generate one or more files from which a plurality of holograms may be produced of combinations of two or more of:
- the 2D or 3D model of the patient's knee;
- the one or more cut planes to the patient's knee; and
- the at least one implant for the patient's knee; and an augmented reality (AR) head-mounted device (HMD), the AR HMD including:
- at least one sensor configured to recognize at least a portion of the patient's knee, the recognize including tracking the at least a portion of the patient's knee;
- one or more projectors configured to present the plurality of holograms; and
- a navigation system that anchors the plurality of holograms in a space based on the coordinate system for the patient's knee.

14. The system of claim 13 wherein the at least a portion of the patient's knee recognized by the at least one sensor of the AR HMD is a portion of a femur as exposed during a surgical procedure or a portion of a tibia as exposed during the surgical procedure.

15. The system of claim 14 wherein the navigation system of the AR HMD registers the at least a portion of the patient's knee based on the recognize the at least a portion of the patient's knee and transfers registration of the at least a portion of the patient's knee to a tracker affixed to the patient's knee.

16. The system of claim 13 wherein the one or more cut planes include an anterior cut plane, an anterior bevel cut plane, a posterior cut plane, and a posterior bevel cut plane.

17. A system comprising:
a computer-based surgical planning system configured to:
- present a two-dimensional (2D) or a three-dimensional (3D) model of at least a portion of a patient's mandible and/or maxilla including a dental mold attached to one or more of the patient's teeth, the dental mold including an element that defines a predetermined location of a tracker;
- establish a coordinate system for the tracker;
- determine a location of at least one dental implant in the portion of the patient's mandible and/or maxilla relative to the coordinate system for the tracker;
- generate one or more files from which one or more holograms may be produced of:
  - the 2D or 3D model of the portion of the patient's mandible and/or maxilla; and
  - the at least one dental implant; and an augmented reality (AR) head-mounted device (HMD), the AR HMD including:
- at least one sensor configured to recognize the tracker attached to the dental mold attached to the one or more of the patient's teeth;
- one or more projectors configured to present the one or more holograms; and
- a navigation system that anchors the one or more holograms in a space based on the coordinate system for the tracker.

18. The system of claim 17 wherein the element that defines the predetermined location of the tracker is:
- the tracker;
- a support for the tracker;
- an attachment mechanism for the tracker; or
- information incorporated in the dental mold.

19. The system of claim 17 wherein the tracker is at least one of a dynamic reference base, one or more Quick Response codes, a recognizable image, or a recognizable object.

* * * * *